US008153650B2

(12) United States Patent
Dubois et al.

(10) Patent No.: US 8,153,650 B2
(45) Date of Patent: Apr. 10, 2012

(54) N-(AMINO-HETEROARYL)-1H-PYRROLO-PYRIDINE-2-CARBOXAMIDES DERIVATIVES PREPARATION THEREOF AND THEIR USE IN THERAPY

(75) Inventors: Laurent Dubois, Paris (FR); Yannick Evanno, Paris (FR); Catherine Gille, Paris (FR); David Machnik, Paris (FR); André Malanda, Paris (FR)

(73) Assignee: Sanofi-Aventis, Paris (FR)

( * ) Notice: Subject to any disclaimer, the term of this patent is extended or adjusted under 35 U.S.C. 154(b) by 435 days.

(21) Appl. No.: 12/489,672

(22) Filed: Jun. 23, 2009

(65) Prior Publication Data

US 2010/0041634 A1  Feb. 18, 2010

Related U.S. Application Data

(63) Continuation of application No. PCT/FR2007/002122, filed on Dec. 20, 2007.

(30) Foreign Application Priority Data

Dec. 26, 2006  (FR) ..................... 06 11353

(51) Int. Cl.
*A01N 43/42* (2006.01)
*A61K 31/44* (2006.01)
*C07D 221/02* (2006.01)

(52) U.S. Cl. ....................... 514/299; 546/112

(58) Field of Classification Search .................. 514/299; 546/112
See application file for complete search history.

(56) References Cited

U.S. PATENT DOCUMENTS

| 6,630,496 B1 | 10/2003 | Seehra et al. |
| 2005/0165049 A1 | 7/2005 | Hulme et al. |
| 2006/0040964 A1 | 2/2006 | Bakthavatchalam et al. |

FOREIGN PATENT DOCUMENTS

| EP | 1535922 | 6/2005 |
| WO | WO 02/48152 | 6/2002 |
| WO | WO 03/028719 | 4/2003 |
| WO | WO 03/068749 | 8/2003 |
| WO | WO 03/080610 | 10/2003 |
| WO | WO 2004/052869 | 6/2004 |
| WO | WO 2004/056768 | 7/2004 |
| WO | WO 2004/062665 | 7/2004 |
| WO | WO 2004/072069 | 8/2004 |
| WO | WO 2004/096784 | 11/2004 |
| WO | WO 2004/108133 | 12/2004 |
| WO | WO 2004/110986 | 12/2004 |
| WO | WO 2005/028452 | 3/2005 |
| WO | WO 2005/035526 | 4/2005 |
| WO | WO 2006/024776 | 3/2006 |
| WO | WO 2006/040522 | 4/2006 |
| WO | WO 2007010138 | 1/2007 |

OTHER PUBLICATIONS

Abramovitch, R. A., et. al., Microwave-Assisted Alkylations of Activatived Methylene Groups, Synthetic Communications, (1995), vol. 25, No. 1, pp. 1-8.

Antilla, J. C. et al, The Copper-Catalyzed N-Arylation of Indoles, J. Am. Chem. Soc., vol. 124, No. 39, 2002, pp. 11684-11688.

Barberis, C., et al., Cu(I)-Catalyzed Intramolecular Cyclization of Ene-Carbamates; Synthesis of Indoles and Pyrrolo[2,3-c]Pyridines, Tetrahedron Letters, vol. 46, (2005), pp. 8877-8880.

Brands, M., et. al., Novel, Selective Indole-Based ECE Inhibitors: Lead Optimization Via Solid-Phase and Classical Synthesis , Bioorganic & Medicinal Chemistry Letters, vol. 15, (2005), pp. 4201-4205.

Carling, R. W., et. al., 3-Phenyl-6-(2-Pyridyl)Methyloxy-1,2,4-Triazolo[3,4-a]Phthalazines and Analogues: High-Affinity y-Aminobutyric Acid-A Benzodiazepine Receptor Ligands with a2, a3, and a5-Subtype Binding Selectivity Over a1, J. Med. Chem. (2004), vol. 47, pp. 1807-1822.

Fresneda, P. M., et al., Synthetic Studies Towards the 2-Aminopyrimidine Alkaloids Variolins and Meridianins From Marine Origin, Tetrahedron Letters, vol. 41, (2000), pp. 4777-4780.

Grogran, C. H., et. al., w-Azabicyclic Butyrophenones, J. Med. Chem., (1967), vol. 10, No. 4. pp. 621-623.

Gunthorpe, M. J., et. al., Peripheral TRPV1 Receptors As Targets for Drug Development: New Molecules and Mechanisms , Current Pharmaceutical Design, (2008), vol. 14, pp. 32-41.

Hurst, D. T., et. al., The Synthesis of Some 2-(Substituted) 5-Nitropyrimidines, Heterocycles, vol. 6, No. 12, (1977), pp. 1999-2004.

Klapars, A., et. al., A General and Efficient Copper Catalyst for the Amidation of Aryl Halides and the N-Arylation of Nitrogen Heterocycles, J. Am Chem. Soc., (2001) pp. 7727-7729 vol. 123.

Kolasa, T., et. al., Synthesis of Indolylalkoxyiminoalkylcarboxylates as Leukotriene Biosynthesis Inhibitors, Bioorganic & Medicinal Chemistry, vol. 5, No. 3, pp. 507-514, (1997).

Lachance, N., et al., Rapid and Efficient Microwave-Assisted Synthesis of 4-, 5-, 6-, and 7-Azaindoles, Synthesis, (2005), vol. 15, pp. 2571-2577.

Lomberget, T., et. al., A Regioselective Route to 5- and 6-Azaindoles Synlett, (2005), vol. 13, pp. 2080-2082.

Menendez, L., et. al., Analgesic Effects of Capsazepine and Resiniferatoxin on Bone Cancer Pain in Mice, Neuroscience Letters, vol. 393, (2006), pp. 70-73.

(Continued)

Primary Examiner — Niloofar Rahmani
(74) Attorney, Agent, or Firm — Serena Farquharson-Torres; Scully, Scott, Murphy & Presser, P.C.

(57) ABSTRACT

The invention relates to compounds of the general formula (I):

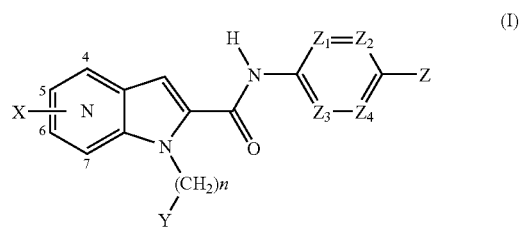

Wherein X, Y, Z, $Z_1$, $Z_2$, $Z_3$, $Z_4$ and n are as defined herein. The invention also relates to a method for making the same and to the use thereof in therapy.

21 Claims, No Drawings

OTHER PUBLICATIONS

Mitsunobu. O., et. al., The Use of Diethyl Azodicarboxylate and Triphenylphosphine in Synthesis and Transformation of Natural Products, Synthesis, (1981), pp. 1-28.

Nazare. M, et. al., A Flexible, Palladium-Catalyzed Indole and Azaindole Synthesis by Direct Annulation of Chloroanilines and Chloroaminopyridines With Ketones, Angew. Chem. Int. Ed., (2004), vol. 43, pp. 4526-4528.

Roy, P. J., et. al., The Hemetsberger-Knittel Synthesis of Substituted 5-, 6-, and 7-Azaindoles, Synthesis, (2005), vol. 16, pp. 2751-2757.

Russell, M. G. N., et. al., Discovery of Functionally Selective 7,8,9,10-Tetrahydro-7,10-Ethano-1,2,4-Triazolo[3,4-a]Phthalazines as GABAA Receptor Agonists at the a3 Subunit, J. Med. Chem., (2005), vol. 48, pp. 1367-1383.

Shen, Q, et. al., Highly Reactive, General, and Long-Lived Catalysts for Coupling Heteroaryl and Aryl Chlorides with Primary Nitrogen Nucleophiles, Angew. Chem. Int. Ed., (2005), vol. 44, pp. 1371-1375.

Szallasi, A., et. al., TRPV1: A Therapeutic Target for Novel Analgesic Drugs?, Trends in Molecular Medicine, vol. 12, No. 11, pp. 545-554, (2006).

Szallasi, A., et al., The Vanilloid Receptor TRPV1: 10 Years from Channel Cloning to Antagonist Proof-of-Concept, Nature Reviews, Drug Discovery, vol. 6, pp. 357-372, (2007).

Nagy, I., et. al., The Role of the Vanilloid (Capsaicin) Receptor (TRPV1) in Physiology and Pathology, European Journal of Pharmacology, vol. 500, No, 1-3, pp. 351-369, (2004).

N-(AMINO-HETEROARYL)-1H-PYRROLO-PYRIDINE-2-CARBOXAMIDES DERIVATIVES PREPARATION THEREOF AND THEIR USE IN THERAPY

CROSS REFERENCE TO RELATED APPLICATIONS

This application is a continuation of International application No. PCT/FR2007/002,122, filed Dec. 20, 2007, which is incorporated herein by reference in its entirety; which claims the benefit of priority of French Patent Application No. 06/11, 353, filed Dec. 26, 2006.

BACKGROUND OF THE INVENTION

Field of the Invention

The invention relates to compounds derived from N-(amino-heteroaryl)-1H-pyrrolopyridine-2-carboxamides, which display antagonist activity in vitro and in vivo for type TRPV1 (or VR1) receptors.

A first object of the invention relates to compounds corresponding to general formula (I) given below.

Another object of the invention relates to methods of preparation of the compounds of general formula (I).

Another object of the invention relates to the use of the compounds of general formula (I) notably in medicinal products or in pharmaceutical compositions.

SUMMARY OF THE INVENTION

The compounds of the invention correspond to general formula (I):

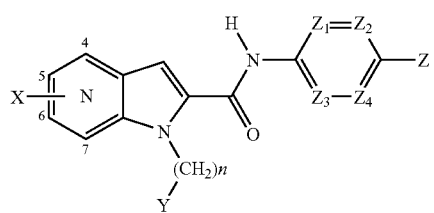

in which
the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group;
the pyrrolopyridine nucleus being optionally substituted in carbon position 4, 5, 6 and/or 7 with one or more substituents X, which may be identical to or different from one another, selected from a hydrogen or halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, —S(O)—$C_1$-$C_6$-alkyl, —S(O)$_2$—$C_1$-$C_6$-alkyl, SF$_5$, C(O)NR$_1$R$_2$, SO$_2$NR$_1$R$_2$, nitro, NR$_1$R$_2$, OCONR$_1$R$_2$, NR$_3$COR$_4$, NR$_3$CONR$_1$R$_2$, NR$_3$SO$_2$R$_5$, NR$_3$SO$_2$NR$_1$R$_2$, aryl-$C_1$-$C_6$-alkylene, heteroaryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
n is equal to 0, 1, 2 or 3;
Y represents an aryl or a heteroaryl,
the aryl or the heteroaryl being optionally substituted with one or more groups selected from a halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, thiol, —S(O)—$C_1$-$C_6$-alkyl, —S(O)$_2$—$C_1$-$C_6$-alkyl, C(O)NR$_1$R$_2$, SO$_2$NR$_1$R$_2$, SF$_5$, nitro, OCONR$_1$R$_2$, NR$_3$COR$_4$, NR$_3$CONR$_1$R$_2$, NR$_1$R$_2$, NR$_3$SO$_2$NR$_1$R$_2$, NR$_3$COR$_4$, NR$_3$SO$_2$R$_5$, aryl-$C_1$-$C_6$-alkylene or aryl group, the aryl and the aryl-$C_1$-$C_6$-alkylene being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;
$Z_1$, $Z_2$, $Z_3$, $Z_4$ represent, independently of one another, a nitrogen atom or a group C(R$_6$), at least one corresponding to a nitrogen atom and at least one corresponding to a group C(R$_6$); the nitrogen atom or one of the nitrogen atoms present in the ring, defined as position-1 nitrogen, being optionally substituted with R$_7$ when the carbon atom in position 2 or 4 relative to this reference nitrogen is substituted with an oxo or thio group;
Z represents
either a cyclic amine attached by the nitrogen atom, of formula:

in which
A represents a $C_1$-$C_7$-alkylene group optionally substituted with one or two groups R$_8$;
B represents a $C_1$-$C_7$-alkylene group optionally substituted with one or two groups R$_9$;
L represents a linkage, a sulfur, oxygen or nitrogen atom; the nitrogen atom being optionally substituted with a group R$_{10}$ or R$_{11}$;
the carbon atoms of the cyclic amine Z being optionally substituted with one or more groups R$_{12}$ which may be identical to or different from one another;
or an acyl amine, attached by the nitrogen atom, of formula NRaRb in which Ra and Rb represent, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-alkyl-C(O)—, HO—C(O)—$C_1$-$C_6$-alkylene, $C_1$-$C_6$-alkyl-O—C(O)—$C_1$-$C_6$-alkylene, aryl or heteroaryl group, and Ra and Rb can optionally be substituted with one or more groups Rc which may be identical to or different from one another;
Rc represents a halogen atom, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, cyano, C(O)NR$_1$R$_2$, NR$_1$R$_2$, SO$_2$NR$_1$R$_2$, NR$_3$COR$_4$, NR$_3$SO$_2$R$_5$, OC(O)NR$_1$R$_2$, NR$_3$COOR$_5$, NR$_3$CONR$_1$R$_2$, NR$_3$SO$_2$NR$_1$R$_2$, hydroxyl, thiol, oxo, thio, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group; or $R_1$ and $R_2$ together form, with the nitrogen atom by which they are carried, an azetidinyl, pyrrolidinyl, piperidinyl, azepinyl, morpholinyl, thiomorpholinyl, piperazinyl, homopiperazinyl group, said group being optionally substituted with a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_3$ and $R_4$ represent, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

or $R_3$ and $R_4$ together form a ($C_2$-$C_5$)alkylene group;

or $R_1$ and $R_3$ together form a ($C_2$-$C_5$)alkylene group;

$R_5$ represents a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

or $R_3$ and $R_5$ together form a ($C_2$-$C_5$)alkylene group;

$R_6$ represents a hydrogen or halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, hydroxyl, thiol, oxo, thio, aryl, aryl-$C_1$-$C_6$-alkylene, heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_7$ represents a hydrogen atom, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, aryl, aryl-$C_1$-$C_6$-alkylene or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_8$, $R_9$ and $R_{10}$ are defined such that:

two groups $R_8$ can together form a linkage or a $C_1$-$C_6$-alkylene group;

two groups $R_9$ can together form a linkage or a $C_1$-$C_6$-alkylene group;

$R_8$ and $R_9$ can together form a linkage or a $C_1$-$C_6$-alkylene group;

$R_8$ and $R_{10}$ can together form a linkage or a $C_1$-$C_6$-alkylene group;

$R_9$ and $R_{10}$ can together form a linkage or a $C_1$-$C_6$-alkylene group;

$R_{11}$ represents a hydrogen atom, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, hydroxyl, $C_1$-$C_6$-alkyl-CO—, COOR$_5$, C(O)NR$_1$R$_2$, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group;

$R_{12}$ represents a fluorine atom, a $C_1$-$C_6$-alkyl group optionally substituted with an $R_{13}$, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-cycloalk-1,1-diyl, $C_3$-$C_7$-heterocycloalk-1,1-diyl group optionally substituted on a nitrogen atom with an $R_{11}$, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, CO$_2$H, C(O)O—$C_1$-$C_6$-alkyl, C(O)NR$_1$R$_2$, NR$_1$R$_2$, NR$_3$COR$_4$, OC(O)NR$_1$R$_2$, NR$_3$COOR$_5$, NR$_3$CONR$_1$R$_2$, hydroxyl, thiol, oxo, thio, aryl-$C_1$-$C_6$-alkylene, aryl group, the aryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group;

$R_{13}$ represents a $C_1$-$C_6$-alkoxyl, $C_3$-$C_7$-cycloalkoxyl, $C_3$-$C_7$-cycloalkyl-$C_1$-$C_6$-alkylene-O—, C(O)NR$_1$R$_2$, NR$_1$R$_2$, NR$_3$COR$_4$, OC(O)NR$_1$R$_2$, NR$_3$COOR$_5$, hydroxyl group.

In the compounds of general formula (I), the nitrogen atom or atoms can be in oxidized form (N-oxide).

DETAILED DESCRIPTION OF THE INVENTION

Among the compounds of general formula (I) according to the invention, a first subgroup of compounds comprises compounds for which the pyrrolopyridine nucleus is a pyrrolo[3,2-b]pyridine group, a pyrrolo[2,3-c]pyridine group or a pyrrolo[2,3-b]pyridine group.

Among the compounds of general formula (I) according to the invention, a second subgroup of compounds comprises compounds for which, if n is equal to 0, then the substituent or substituents X, which may be identical to or different from one another, are selected from a hydrogen or halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, —S(O)—$C_1$-$C_6$-alkyl, —S(O)$_2$—$C_1$-$C_6$-alkyl, SF$_5$, C(O)NR$_1$R$_2$, SO$_2$NR$_1$R$_2$, nitro, NR$_1$R$_2$, OCONR$_1$R$_2$, NR$_3$COR$_4$, NR$_3$CONR$_1$R$_2$, NR$_3$SO$_2$R$_5$, NR$_3$SO$_2$NR$_1$R$_2$ group.

Among the compounds of general formula (I) according to the invention, a third subgroup of compounds comprises compounds for which, when n=0 or 1, Y is different from a bare phenyl.

Among the compounds of general formula (I) according to the invention, a fourth subgroup of compounds comprises compounds for which the substituent or substituents X, which may be identical to or different from one another, are selected from a hydrogen or halogen atom, more particularly a fluorine atom, or a $C_1$-$C_6$-fluoroalkyl group, more particularly trifluoromethyl.

Among the compounds of general formula (I) according to the invention, a fifth subgroup of compounds comprises compounds for which n is equal to 1.

Among the compounds of general formula (I) according to the invention, a sixth subgroup of compounds comprises compounds for which Y represents an aryl, more particularly a phenyl, or a heteroaryl, more particularly a pyridinyl, the aryl or the heteroaryl being optionally substituted with one or more, more particularly with one or two, groups selected from a halogen atom, more particularly a fluorine or chlorine atom, or a $C_1$-$C_6$-alkyl group, more particularly methyl, $C_1$-$C_6$-fluoroalkyl group, more particularly trifluoromethyl, $C_1$-$C_6$-alkoxyl group, more particularly methoxy, $C_1$-$C_6$-fluoroalkoxyl group, more particularly trifluoromethoxy.

Among the compounds of general formula (I) according to the invention, a seventh subgroup of compounds comprises compounds for which $Z_1$, $Z_2$, $Z_3$, $Z_4$ represent, independently of one another, a nitrogen atom or a group $C(R_6)$, at least one corresponding to a nitrogen atom and at least one corresponding to a group $C(R_6)$;

$R_6$ represents a hydrogen or halogen atom, more particularly a fluorine atom, or a $C_1$-$C_6$-alkyl group, more particularly a methyl, $C_1$-$C_6$-fluoroalkyl group, more particularly a trifluoromethyl or $C_1$-$C_6$-alkoxyl group, more particularly methoxy.

Among the compounds of general formula (I) according to the invention, an eighth subgroup of compounds comprises compounds for which Z represents either a cyclic amine attached by the nitrogen atom, of formula:

in which
A represents a $C_1$-$C_7$-alkylene group optionally substituted with one or two groups $R_8$;
B represents a $C_1$-$C_7$-alkylene group optionally substituted with one or two groups $R_9$;
L represents a linkage;
the carbon atoms of the cyclic amine Z being optionally substituted with one or more groups $R_{12}$ which may be identical to or different from one another; $R_{12}$ represents a fluorine atom, a $C_1$-$C_6$-alkyl, $C_1$-$C_6$-alkoxyl, $C_3$-$C_7$-cycloalkyl-$C_1$-$C_6$-alkylene-O—, $CO_2H$, $C(O)O$—$C_1$-$C_6$-alkyl or hydroxyl group;
$R_8$ and $R_9$ are defined such that:
two groups $R_8$ can together form a linkage or a $C_1$-$C_6$-alkylene group;
two groups $R_9$ can together form a linkage or a $C_1$-$C_6$-alkylene group;
$R_8$ and $R_9$ can together form a linkage or a $C_1$-$C_6$-alkylene group;
or an acyl amine, attached by the nitrogen atom, of formula NRaRb in which Ra and Rb represent, independently of one another, a hydrogen atom or a $C_1$-$C_6$-alkyl, $C_1$-$C_6$-alkyl-C(O)—, HO—C(O)—$C_1$-$C_6$-alkylene or $C_1$-$C_6$-alkyl-O—C(O)—$C_1$-$C_6$-alkylene group, and Ra and Rb can optionally be substituted with a group Rc where Rc represents a hydroxyl.

Among the compounds of general formula (I) according to the invention, a ninth subgroup of compounds comprises compounds for which Z represents
either a cyclic amine attached by the nitrogen atom, of formula:

in which
A represents a $C_1$-$C_7$-alkylene group optionally substituted with a group $R_8$;
B represents a $C_1$-$C_7$-alkylene group optionally substituted with a group $R_9$;
L represents a linkage;
the carbon atoms of the cyclic amine Z being optionally substituted with one or more groups $R_{12}$ which may be identical to or different from one another; $R_{12}$ represents a fluorine atom, a $C_1$-$C_6$-alkyl, $C_1$-$C_6$-alkoxyl, $C_3$-$C_7$-cycloalkyl-$C_1$-$C_6$-alkylene-O—, $CO_2H$, $C(O)O$—$C_1$-$C_6$-alkyl or hydroxyl group;
$R_8$ and $R_9$ are defined such that:
$R_8$ and $R_9$ can together form a linkage;
or an acyl amine, attached by the nitrogen atom, of formula NRaRb in which Ra and Rb represent, independently of one another, a hydrogen atom or a $C_1$-$C_6$-alkyl, $C_1$-$C_6$-alkyl-C(O)—, HO—C(O)—$C_1$-$C_6$-alkylene or $C_1$-$C_6$-alkyl-O—C(O)—$C_1$-$C_6$-alkylene group, and Ra and Rb can optionally be substituted with a group Rc where Rc represents a hydroxyl.

Among the compounds of general formula (I) according to the invention, a tenth subgroup of compounds comprises compounds for which Z represents
either a cyclic amine attached by the nitrogen atom and selected from the pyrrolidinyl, azetidinyl, azabicyclo[3.2.0]heptyl or azabicyclo[3.1.0]hexyl groups, the carbon atoms of the cyclic amine being optionally substituted with one or more groups $R_{12}$ which may be identical to or different from one another; $R_{12}$ represents a fluorine atom, a $C_1$-$C_6$-alkyl group, more particularly methyl, $C_1$-$C_6$-alkoxyl group, more particularly methoxy, $C_3$-$C_7$-cycloalkyl-$C_1$-$C_6$-alkylene-O— group, more particularly cyclopropylmethyloxy, $CO_2H$, $C(O)O$—$C_1$-$C_6$-alkyl, more particularly C(O)O-ter-butyl, or hydroxyl group;
or an acyl amine, attached by the nitrogen atom, of formula NRaRb in which Ra and Rb represent, independently of one another, a hydrogen atom or a $C_1$-$C_6$-alkyl group, more particularly methyl, propyl, isopropyl, $C_1$-$C_6$-alkyl-C(O)—, more particularly $CH_3$—C(O)—, HO—C(O)—$C_1$-$C_6$-alkylene, more particularly HO—C(O)—$(CH_2)_2$—, or $C_1$-$C_6$-alkyl-O—C(O)—$C_1$-$C_6$-alkylene, more particularly $CH_3CH_2$—COO—$(CH_2)_2$—, and Ra and Rb can optionally be substituted with a group Rc where Rc represents a hydroxyl.

Among the compounds of the invention, an eleventh subgroup of compounds comprises compounds of general formula (I) in which, simultaneously, the pyrrolopyridine nucleus and/or X and/or n and/or Y and/or $Z_1$, $Z_2$, $Z_3$, $Z_4$ and/or Z are as defined in the above groups.

Among the compounds of general formula (I) according to the invention, a twelfth subgroup of compounds comprises compounds for which the pyrrolopyridine nucleus is a pyrrolo[3,2-b]pyridine group, a pyrrolo[2,3-c]pyridine group or a pyrrolo[2,3-b]pyridine group;

the substituent or substituents X, which may be identical to or different from one another, are selected from a hydrogen or halogen atom, more particularly a fluorine atom, or a $C_1$-$C_6$-fluoroalkyl group, more particularly trifluoromethyl;

n is equal to 1;

Y represents an aryl, more particularly a phenyl, or a heteroaryl, more particularly a pyridinyl, the aryl or the heteroaryl being optionally substituted with one or more, more particularly with one or two, groups selected from a halogen atom, more particularly a fluorine or chlorine atom, or a $C_1$-$C_6$-alkyl group, more particularly methyl, $C_1$-$C_6$-fluoroalkyl, more particularly trifluoromethyl, $C_1$-$C_6$-alkoxyl, more particularly methoxy, $C_1$-$C_6$-fluoroalkoxyl, more particularly trifluoromethoxy;

$Z_1$, $Z_2$, $Z_3$, $Z_4$ represent, independently of one another, a nitrogen atom or a group $C(R_6)$, at least one corresponding to a nitrogen atom and at least one corresponding to a group $C(R_6)$;

$R_6$ represents a hydrogen or halogen atom, more particularly a fluorine atom, or a $C_1$-$C_6$-alkyl group, more particularly a methyl, $C_1$-$C_6$-fluoroalkyl, more particularly a trifluoromethyl or $C_1$-$C_6$-alkoxyl, more particularly methoxy;

Z represents either a cyclic amine attached by the nitrogen atom and selected from the pyrrolidinyl, azetidinyl, azabicyclo[3.2.0]heptyl or azabicyclo[3.1.0]hexyl groups, the carbon atoms of the cyclic amine being optionally substituted with one or more groups $R_{12}$ which may be identical to or different from one another; $R_{12}$ represents a fluorine atom, a $C_1$-$C_6$-alkyl group, more particularly methyl, $C_1$-$C_6$-alkoxyl, more particularly methoxy, $C_3$-$C_7$-cycloalkyl-$C_1$-$C_6$-alkylene-O—, more particularly cyclopropylmethyloxy, $CO_2H$, $C(O)O$—$C_1$-$C_6$-alkyl, more particularly $C(O)$O-ter-butyl, or hydroxyl;

or an acyl amine, attached by the nitrogen atom, of formula NRaRb in which Ra and Rb represent, independently of one another, a hydrogen atom or a $C_1$-$C_6$-alkyl group, more particularly methyl, propyl, isopropyl, $C_1$-$C_6$-alkyl-C(O)—, more particularly $CH_3$—$C(O)$—, HO—$C(O)$—$C_1$-$C_6$-alkylene, more particularly HO—$C(O)$—$(CH_2)_2$—, or $C_1$-$C_6$-alkyl-O—$C(O)$—$C_1$-$C_6$-alkylene, more particularly $CH_3CH_2$—COO—$(CH_2)_2$—, and Ra and Rb can optionally be substituted with a group Rc where Rc represents a hydroxyl.

Among the compounds of general formula (I), a subfamily of compounds is represented by general formula (Ia):

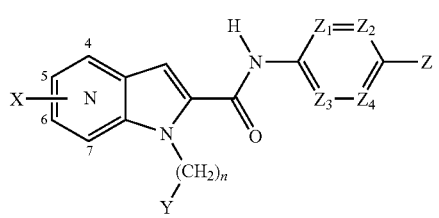

(Ia)

in which the pyrrolopyridine nucleus is a pyrrolo[3,2-b]pyridine group, a pyrrolo[3,2-c]pyridine group, a pyrrolo[2,3-c]pyridine group or a pyrrolo[2,3-b]pyridine group;

the pyrrolopyridine nucleus being optionally substituted in carbon position 4, 5, 6 and/or 7 with one or more substituents X, which may be identical to or different from one another, selected from a hydrogen or halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, —S(O)—$C_1$-$C_6$-alkyl, —$S(O)_2$—$C_1$-$C_6$-alkyl, $SF_5$, $C(O)NR_1R_2$, $SO_2NR_1R_2$, nitro, $NR_1R_2$, $OCONR_1R_2$, $NR_3COR_4$, $NR_3CONR_1R_2$, $NR_3SO_2R_5$, $NR_3SO_2NR_1R_2$, aryl-$C_1$-$C_6$-alkylene, heteroaryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

n is equal to 0, 1, 2 or 3;

Y represents an aryl or a heteroaryl, the aryl or the heteroaryl being optionally substituted with one or more groups selected from a halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, thiol, —S(O)—$C_1$-$C_6$-alkyl, —$S(O)_2$—$C_1$-$C_6$-alkyl, $C(O)NR_1R_2$, $SO_2NR_1R_2$, $SF_5$, nitro, $OCONR_1R_2$, $NR_3COR_4$, $NR_3CONR_1R_2$, $NR_1R_2$, $NR_3SO_2NR_1R_2$, $NR_3COR_4$, $NR_3SO_2R_5$, aryl-$C_1$-$C_6$-alkylene or aryl group, the aryl and the aryl-$C_1$-$C_6$-alkylene being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$Z_1$, $Z_2$, $Z_3$, $Z_4$ represent, independently of one another, a nitrogen atom or a group $C(R_6)$, at least one corresponding to a nitrogen atom and at least one corresponding to a group $C(R_6)$; the nitrogen atom or one of the nitrogen atoms present in the ring, defined as position-1 nitrogen, being optionally substituted with $R_7$ when the carbon atom in position 2 or 4 relative to this reference nitrogen is substituted with an oxo or thio group;

Z represents either a cyclic amine attached by the nitrogen atom, of formula:

in which

A represents a $C_1$-$C_7$-alkylene group optionally substituted with one or two groups $R_8$;

B represents a $C_1$-$C_7$-alkylene group optionally substituted with one or two groups $R_9$;

L represents a linkage, a sulfur, oxygen or nitrogen atom; the nitrogen atom being optionally substituted with a group $R_{10}$ or $R_{11}$;

the carbon atoms of the cyclic amine Z being optionally substituted with one or more groups $R_{12}$ which may be identical to or different from one another;

or an acyl amine, attached by the nitrogen atom, of formula NRaRb in which Ra and Rb represent, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkyl-$C_1$-$C_6$-alkylene-O—, $C_1$-$C_6$-fluoroalkoxyl, aryl or heteroaryl group, and Ra and Rb can optionally be substituted with one or more groups Rc which may be identical to or different from one another;

Rc represents a halogen atom, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, cyano, C(O)NR$_1$R$_2$, NR$_1$R$_2$, SO$_2$NR$_1$R$_2$, NR$_3$COR$_4$, NR$_3$SO$_2$R$_5$, OC(O)NR$_1$R$_2$, NR$_3$COOR$_5$, NR$_3$CONR$_1$R$_2$, NR$_3$SO$_2$NR$_1$R$_2$, hydroxyl, thiol, oxo, thio, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group; or $R_1$ and $R_2$ together form, with the nitrogen atom by which they are carried, an azetidinyl, pyrrolidinyl, piperidinyl, azepinyl, morpholinyl, thiomorpholinyl, piperazinyl, homopiperazinyl group, said group being optionally substituted with a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_3$ and $R_4$ represent, independently of one another, a hydrogen atom or a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

or $R_3$ and $R_4$ together form a ($C_2$-$C_5$)alkylene group;

or $R_1$ and $R_3$ together form a ($C_2$-$C_5$)alkylene group;

$R_5$ represents a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

or $R_3$ and $R_5$ together form a ($C_2$-$C_5$)alkylene group;

$R_6$ represents a hydrogen or halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, hydroxyl, thiol, oxo, thio, aryl, aryl-$C_1$-$C_6$-alkylene, heteroaryl group, the aryl and the heteroaryl being optionally substituted with one or more substituents selected from a halogen, a $C_1$-$C_6$-alkyl group, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_7$ represents a hydrogen atom, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, aryl, aryl-$C_1$-$C_6$-alkylene or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_8$, $R_9$ and $R_{10}$ are defined such that:

two groups $R_8$ can together form a linkage or a $C_1$-$C_6$-alkylene group;

two groups $R_9$ can together form a linkage or a $C_1$-$C_6$-alkylene group;

$R_8$ and $R_9$ can together form a linkage or a $C_1$-$C_6$-alkylene group;

$R_8$ and $R_{10}$ can together form a linkage or a $C_1$-$C_6$-alkylene group;

$R_9$ and $R_{10}$ can together form a linkage or a $C_1$-$C_6$-alkylene group;

$R_{11}$ represents a hydrogen atom, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, hydroxyl, $C_1$-$C_6$-alkyl-CO—, COOR$_5$, C(O)NR$_1$R$_2$, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group;

$R_{12}$ represents a fluorine atom, a $C_1$-$C_6$-alkyl group optionally substituted with an $R_{13}$, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-cycloalk-1,1-diyl, $C_3$-$C_7$-heterocycloalk-1,1-diyl group optionally substituted on a nitrogen atom with an $R_{11}$, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, CO$_2$H, C(O)O—$C_1$-$C_6$-alkyl, C(O)NR$_1$R$_2$, NR$_1$R$_2$, NR$_3$COR$_4$, OC(O)NR$_1$R$_2$, NR$_3$COOR$_5$, NR$_3$CONR$_1$R$_2$, hydroxyl, thiol, oxo, thio, aryl-$C_1$-$C_6$-alkylene, aryl group, the aryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group;

$R_{13}$ represents a $C_1$-$C_6$-alkoxyl, $C_3$-$C_7$-cycloalkoxyl, $C_3$-$C_7$-cycloalkyl-$C_1$-$C_6$-alkylene-O—, C(O)NR$_1$R$_2$, NR$_1$R$_2$, NR$_3$COR$_4$, OC(O)NR$_1$R$_2$, NR$_3$COOR$_5$, hydroxyl group.

In the compounds of general formula (Ia), the nitrogen atom or atoms can be in oxidized form (N-oxide).

Among the compounds of general formula (Ia), a first subgroup of compounds comprises compounds for which the pyrrolopyridine nucleus is a pyrrolo[3,2-b]pyridine group or a pyrrolo[2,3-b]pyridine group.

Among the compounds of general formula (Ia), a second subgroup of compounds comprises compounds for which, if n is equal to 0, then the substituent or substituents X, which may be identical to or different from one another, are selected from a hydrogen or halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, —S(O)—$C_1$-$C_6$-alkyl, —S(O)$_2$—$C_1$-$C_6$-alkyl, SF$_5$, C(O)NR$_1$R$_2$, SO$_2$NR$_1$R$_2$, nitro, NR$_1$R$_2$, OCONR$_1$R$_2$, NR$_3$COR$_4$, NR$_3$CONR$_1$R$_2$, NR$_3$SO$_2$R$_5$, NR$_3$SO$_2$NR$_1$R$_2$ group.

Among the compounds of general formula (Ia), a third subgroup of compounds comprises compounds for which the substituent or substituents X, which may be identical to or different from one another, are selected from a halogen atom, more particularly a fluorine atom, or a $C_1$-$C_6$-fluoroalkyl group, more particularly trifluoromethyl.

Among the compounds of general formula (Ia), a fourth subgroup of compounds comprises compounds for which n is equal to 1.

Among the compounds of general formula (Ia), a fifth subgroup of compounds comprises compounds for which Y represents an aryl, more particularly a phenyl, or a heteroaryl, more particularly a pyridinyl, the aryl or the heteroaryl being optionally substituted with one or more, more particularly by one, halogen atom(s), more particularly fluorine atom(s).

Among the compounds of general formula (Ia), a sixth subgroup of compounds comprises compounds for which $Z_1$, $Z_2$, $Z_3$, $Z_4$ represent, independently of one another, a nitrogen atom or a group C(R$_6$), at least one corresponding to a nitrogen atom and at least one corresponding to a group C(R$_6$); R$_6$ represents a hydrogen atom or a $C_1$-$C_6$-alkyl group, more particularly a methyl, or $C_1$-$C_6$-fluoroalkyl, more particularly a trifluoromethyl.

Among the compounds of general formula (Ia), a seventh subgroup of compounds comprises compounds for which Z represents either a cyclic amine attached by the nitrogen atom, of formula:

in which
A represents a $C_1$-$C_7$-alkylene group;
B represents a $C_1$-$C_7$-alkylene group;
L represents a linkage;
the carbon atoms of the cyclic amine Z being optionally substituted with one or more groups R$_{12}$ which may be identical to or different from one another; R$_{12}$ represents a fluorine atom, a $C_1$-$C_6$-alkyl, hydroxyl group;
or an acyl amine, attached by the nitrogen atom, of formula NRaRb in which Ra and Rb represent, independently of one another, a hydrogen atom or a $C_1$-$C_6$-alkyl group.

Among the compounds of general formula (Ia), an eighth subgroup of compounds comprises compounds for which Z represents either a pyrrolidinyl or azetidinyl group, attached by the nitrogen atom, the carbon atoms of the pyrrolidinyl group being optionally substituted with one or more groups R$_{12}$ which may be identical to or different from one another; R$_{12}$ represents a fluorine atom, a $C_1$-$C_6$-alkyl group, more particularly methyl, or hydroxyl group;
or an acyl amine, attached by the nitrogen atom, of formula NRaRb in which Ra and Rb represent, independently of one another, a hydrogen atom or a $C_1$-$C_6$-alkyl group, more particularly methyl, isopropyl.

Among the compounds of general formula (Ia), a ninth subgroup of compounds comprises compounds of general formula (Ia) in which, simultaneously, the pyrrolopyridine nucleus and/or X and/or n and/or Y and/or $Z_1$, $Z_2$, $Z_3$, $Z_4$ and/or Z are as defined in the aforementioned subgroups.

As non-limiting examples of substituted or unsubstituted amines Z, we may mention methylamine, ethylamine, 2-methoxyethylamine, 2-hydroxyethylamine, cyclopropylamine, hydroxylamine, 2-(N,N-dimethylamino)ethylamine, dimethylamine, isopropylamine, N-ethyl-methylamine, 2,5-dimethylpyrrolidine, 3-hydroxypyrrolidine, 3-ethoxypyrrolidine, 3,3-difluoropyrrolidine, 3,3-difluoroazetidine, 3-hydroxyazetidine, proline, aziridine, azetidine, pyrrolidine, piperidine, azepine, morpholine, thiomorpholine, piperazine, homopiperazine, azabicyclo[3.1.0]hexanes, azabicyclo[3.2.0]heptanes, azabicyclo[3.3.0]octanes, octahydrofuropyrroles, octahydropyrrolopyrroles, octahydroindole, octahydroisoindole, octahydropyrrolopyridines, decahydroquinoline, decahydroisoquinoline, decahydronaphthyridines, octahydropyridopyrazine, azabicylo[3.1.1]heptanes, diazabicylo[2.2.1]heptanes, azabicylo[3.2.1]octanes, diazabicylo[3.2.1]octanes, azabicylo[3.3.1]nonanes.

The following definitions are used in the sense of the present invention:
$C_t$-$C_z$ where t and z can take values from 1 to 7, a carbon chain that can have from t to z carbon atoms, for example $C_1$-$C_3$ a carbon chain that can have from 1 to 3 carbon atoms;
an alkyl: a linear or branched, saturated aliphatic group. We may mention, as examples, the methyl, ethyl, propyl, isopropyl, butyl, isobutyl, tert-butyl, pentyl groups, etc;
an alkylene: a saturated, linear or branched, divalent alkyl group, for example a $C_{1-3}$-alkylene group represents a divalent carbon chain with 1 to 3 carbon atoms, linear or branched, for example a methylene, ethylene, 1-methylethylene, propylene;
a cycloalkyl: a cyclic carbon group. We may mention, as examples, the cyclopropyl, cyclobutyl, cyclopentyl, cyclohexyl groups, etc;
a heterocycloalkyl: a cyclic group with 3 to 7 ring members containing 1 or 2 heteroatoms selected from O, S or N;
a cycloalk-1,1-diyl or a heterocycloalk-1,1-diyl: a group of the type

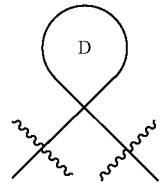

where D is a cycloalkyl or heterocycloalkyl group;
a fluoroalkyl: an alkyl group in which one or more hydrogen atoms have been substituted with a fluorine atom;
an alkoxyl: an —O-alkyl radical, where the alkyl group is as defined previously;
a cycloalkoxyl: an —O-cycloalkyl radical, where the cycloalkyl group is as defined previously;
a fluoroalkoxyl: an alkoxyl group in which one or more hydrogen atoms have been substituted with a fluorine atom;
a thioalkyl: an —S-alkyl radical, where the alkyl group is as defined previously;
an aryl: an aromatic cyclic group comprising between 6 and 10 carbon atoms. As examples of aryl groups, we may mention the phenyl or naphthyl groups;

a heteroaryl: a mono-, bi- or tricyclic aromatic group with 5 to 14 ring members containing from 1 to 8 heteroatoms selected from O, S or N.

As examples of monocyclic heteroaryl, we may mention the imidazolyl, pyrazolyl, thiazolyl, oxazolyl, isothiazolyl, isoxazolyl, furanyl, thiophenyl, oxadiazolyl, thiadiazolyl, triazolyl, tetrazolyl, pyridinyl, pyrazinyl, pyrimidinyl, pyridazinyl, triazinyl groups;

as examples of bicyclic heteroaryl, we may mention the indolyl, isoindolyl, benzofuranyl, benzothiophenyl, benzoxazolyl, benzimidazolyl, indazolyl, benzothiazolyl, isobenzofuranyl, isobenzothiazolyl, pyrrolo[2,3-c]pyridinyl, pyrrolo[2,3-b]pyridinyl, pyrrolo[3,2-b]pyridinyl, pyrrolo[3,2-c]pyridinyl, quinolinyl, isoquinolinyl, cinnolinyl, quinazolinyl or quinoxalinyl groups;

as examples of tricyclic heteroaryl, we may mention the pyrido[1,2-a]benzimidazolyl, thiazolo[1,2-a]benzimidazolyl, imidazo[1,2-a]benzimidazolyl, pyrimido[1,2-a]benzimidazolyl or pyrazino[1,2-a]benzimidazolyl groups;

a halogen atom: a fluorine, a chlorine, a bromine or an iodine;

"oxo" denotes "=O";

"thio" denotes "=S".

The compounds of formula (I) can have one or more asymmetric carbon atoms. They can therefore be in the form of enantiomers or diastereoisomers. These enantiomers, diastereoisomers, as well as mixtures thereof, including the racemic mixtures, form part of the invention.

The compounds of formula (I) can be in the form of bases or of salts of addition to acids. Said salts of addition form part of the invention.

These salts are advantageously prepared with pharmaceutically acceptable acids, but the salts of other acids that can be used, for example for the purification or isolation of the compounds of formula (I), also form part of the invention.

The compounds of general formula (I) can be in the form of hydrates or of solvates, namely in the form of associations or of combinations with one or more molecules of water or with a solvent. Said hydrates and solvates also form part of the invention.

Among the compounds of general formula (I) according to the invention, we may notably mention the following compounds:

1. N-[(6-Methylamino)pyridin-3-yl]-5-trifluoromethyl-1-(3-fluorobenzyl)-1H-pyrrolo[2,3-b]pyridine-2-carboxamide
2. N-(6-N,N-Dimethylamino-5-methylpyridin-3-yl)-5-trifluoromethyl-1-(3-fluorobenzyl)-1H-pyrrolo[2,3-b]pyridine-2-carboxamide
3. N-(6-N,N-Dimethylamino-4-methylpyridin-3-yl)-5-trifluoromethyl-1-(3-fluorobenzyl)-1H-pyrrolo[2,3-b]pyridine-2-carboxamide
4. N-(6-N,N-Dimethylamino-5-trifluoromethyl-pyridin-3-yl)-5-trifluoromethyl-1-(3-fluorobenzyl)-1H-pyrrolo[2,3-b]pyridine-2-carboxamide
5. N-[6-(Pyrrolidin-1-yl)pyridin-3-yl]-5-fluoro-1-(3-fluorobenzyl)-1H-pyrrolo[2,3-b]pyridine-2-carboxamide
6. N-[6-(Pyrrolidin-1-yl)pyridin-3-yl]-5-trifluoromethyl-1-(3-fluorobenzyl)-1H-pyrrolo[2,3-b]pyridine-2-carboxamide
7. N-[5-(Pyrrolidin-1-yl)pyrazin-2-yl]-5-trifluoromethyl-1-(3-fluorobenzyl)-1H-pyrrolo[2,3-b]pyridine-2-carboxamide
8. N-[6-(Dimethylamino)pyridazin-3-yl]-5-trifluoromethyl-1-(3-fluorobenzyl)-1H-pyrrolo[2,3-b]pyridine-2-carboxamide
9. N-[6-(pyrrolidin-1-yl)pyridin-3-yl]-5-trifluoromethyl-1-[(4-pyridyl)methyl]-1H-pyrrolo[2,3-b]pyridine-2-carboxamide
10. N-[6-(Isopropylamino)pyridin-3-yl]-5-trifluoromethyl-1-(3-fluorobenzyl)-1H-pyrrolo[2,3-b]pyridine-2-carboxamide
11. N-[6-(3-hydroxypyrrolidin-1-yl)pyridin-3-yl]-5-trifluoromethyl-1-(3-fluorobenzyl)-1H-pyrrolo[2,3-b]pyridine-2-carboxamide
12. N-[6-(3,3-difluoropyrrolidin-1-yl)pyridin-3-yl]-5-trifluoromethyl-1-(3-fluorobenzyl)-1H-pyrrolo[2,3-b]pyridine-2-carboxamide
13. N-[6-(dimethylamino)pyridin-3-yl]-5-trifluoromethyl-1-(3-fluorobenzyl)-1H-pyrrolo[2,3-b]pyridine-2-carboxamide
14. N-[6-(cis-2,5-dimethylpyrrolidin-1-yl)pyridin-3-yl]-5-trifluoromethyl-1-(3-fluorobenzyl)-1H-pyrrolo[2,3-b]pyridine-2-carboxamide
15 N-[6-(azetidin-1-yl)pyridin-3-yl]-5-trifluoromethyl-1-(3-fluorobenzyl)-1H-pyrrolo[2,3-b]pyridine-2-carboxamide
16 N-[6-(Pyrrolidin-1-yl)pyridin-3-yl]-5-trifluoromethyl-1-(3-fluorobenzyl)-1H-pyrrolo[3,2-b]pyridine-2-carboxamide
17 N-[6-(2-(S)-carboxypyrrolidin-1-yl)pyridin-3-yl]-5-trifluoromethyl-1-(3-fluorobenzyl)-1H-pyrrolo[2,3-b]pyridine-2-carboxamide
18 N-[6-(2-(S)-tertbutyloxycarbonylpyrrolidin-1-yl)pyridin-3-yl]-5-trifluoromethyl-1-(3-fluorobenzyl)-1H-pyrrolo[2,3-b]pyridine-2-carboxamide
19 N-[6-(3,3-difluoroazetidin-1-yl)pyridin-3-yl]-5-trifluoromethyl-1-(3-fluorobenzyl)-1H-pyrrolo[2,3-b]pyridine-2-carboxamide
20 N-[6-(3-hydroxyazetidin-1-yl)pyridin-3-yl]-5-trifluoromethyl-1-(3-fluorobenzyl)-1H-pyrrolo[2,3-b]pyridine-2-carboxamide
21 N-[4-methyl-6-dimethylaminopyridin-3-yl]-5-trifluoromethyl-1-(3-fluorobenzyl)-1H-pyrrolo[2,3-b]pyridine-2-carboxamide
22 N-[4-methyl-6-(pyrrolidin-1-yl)pyridin-3-yl]-6-trifluoromethyl-1-(3-fluorobenzyl)-1H-pyrrolo[2,3-b]pyridine-2-carboxamide
23 N-[6-(3-methoxypyrrolidin-1-yl)pyridin-3-yl]-5-trifluoromethyl-1-(3-fluorobenzyl)-1H-pyrrolo[2,3-b]pyridine-2-carboxamide
24 N-[4-methyl-6-dimethylaminopyridin-3-yl]-5-trifluoromethyl-1-[(pyridin-4-yl)methyl]-1H-pyrrolo[2,3-b]pyridine-2-carboxamide
25 N-[4-methyl-6-(pyrrolidin-1-yl)pyridin-3-yl]-5-trifluoromethyl-1-(3-fluorobenzyl)-1H-pyrrolo[2,3-b]pyridine-2-carboxamide
26 N-[4-methyl-6-(pyrrolidin-1-yl)pyridin-3-yl]-6-trifluoromethyl-1-[(pyridin-4-yl)methyl]-1H-pyrrolo[2,3-b]pyridine-2-carboxamide
27 N-[4-methyl-6-(pyrrolidin-1-yl)pyridin-3-yl]-5-trifluoromethyl-1-[(pyridin-4-yl)methyl]-1H-pyrrolo[2,3-b]pyridine-2-carboxamide
28 N-[4-methyl-6-(methylamino)pyridin-3-yl]-5-trifluoromethyl-1-[(pyridin-4-yl)methyl]-1H-pyrrolo[2,3-b]pyridine-2-carboxamide
29 N-[4-methoxy-6-(pyrrolidin-1-yl)pyridin-3-yl]-5-trifluoromethyl-1-[(pyridin-4-yl)methyl]-1H-pyrrolo[2,3-b]pyridine-2-carboxamide
30 N-[6-(azetidin-1-yl)pyridin-3-yl]-5-trifluoromethyl-1-[(pyridin-4-yl)methyl]-1H-pyrrolo[2,3-b]pyridine-2-carboxamide
31 N-[6-(acetylamino)pyridin-3-yl]-5-trifluoromethyl-1-(3-fluorobenzyl)-1H-pyrrolo[2,3-b]pyridine-2-carboxamide 32  N-[6-aminopyridin-3-yl]-5-trifluoromethyl-1-(3-fluorobenzyl)-1H-pyrrolo[2,3-b]pyridine-2-carboxamide
33  N-[6-(pyrrolidin-1-yl)pyridin-3-yl]-6-trifluoromethyl-1-(3-fluorobenzyl)-1H-pyrrolo[2,3-b]pyridine-2-carboxamide
34  N-[6-(pyrrolidin-1-yl)-4-(trifluoromethyl)pyridin-3-yl]-5-trifluoromethyl-1-(3-fluorobenzyl)-1H-pyrrolo[2,3-b]pyridine-2-carboxamide
35  N-[5-fluoro-6-(dimethylamino)pyridin-3-yl]-5-trifluoromethyl-1-(3-fluorobenzyl)-1H-pyrrolo[2,3-b]pyridine-2-carboxamide
36  N-[2-(dimethylamino)pyrimidin-5-yl]-5-trifluoromethyl-1-(3-fluorobenzyl)-1H-pyrrolo[2,3-b]pyridine-2-carboxamide
37  N-[6-(3-azabicyclo[3.2.0]hept-3-yl)pyridin-3-yl]-5-trifluoromethyl-1-(3-fluorobenzyl)-1H-pyrrolo[2,3-b]pyridine-2-carboxamide
38  N-[6-(3-azabicyclo[3.1.0]hex-3-yl)pyridin-3-yl]-5-trifluoromethyl-1-(3-fluorobenzyl)-1H-pyrrolo[2,3-b]pyridine-2-carboxamide
39  N-[6-(3-azabicyclo[3.1.0]hex-3-yl)pyridin-3-yl]-5-fluoro-1-(3-fluorobenzyl)-1H-pyrrolo[2,3-b]pyridine-2-carboxamide
40  3-[[5-[[[1-(3-fluorobenzyl)-5-trifluoromethyl-1H-pyrrolo[2,3-b]pyridin-2-yl]carbonyl]amino]pyridin-2-yl]amino]propionic acid
41  N-[6-(3-hydroxypropylamino)pyridin-3-yl]-5-trifluoromethyl-1-(3-fluorobenzyl)-1H-pyrrolo[2,3-b]pyridine-2-carboxamide
42  N-[6-(azetidin-1-yl)pyridin-3-yl]-5-trifluoromethyl-1-benzyl-1H-pyrrolo[2,3-b]pyridine-2-carboxamide
43  N-[6-(azetidin-1-yl)pyridin-3-yl]-5-trifluoromethyl-1-(2-fluorobenzyl)-1H-pyrrolo[2,3-b]pyridine-2-carboxamide
44  N-[6-(azetidin-1-yl)pyridin-3-yl]-5-trifluoromethyl-1-(4-fluorobenzyl)-1H-pyrrolo[2,3-b]pyridine-2-carboxamide
45  N-[6-(azetidin-1-yl)pyridin-3-yl]-5-trifluoromethyl-1-(3-trifluoromethyl)benzyl-1H-pyrrolo[2,3-b]pyridine-2-carboxamide
46  N-[6-(azetidin-1-yl)pyridin-3-yl]-5-trifluoromethyl-1-(4-methyl benzyl)-1H-pyrrolo[2,3-b]pyridine-2-carboxamide
47  N-[6-(azetidin-1-yl)pyridin-3-yl]-5-trifluoromethyl-1-(3-methylbenzyl)-1H-pyrrolo[2,3-b]pyridine-2-carboxamide
48  N-[6-(azetidin-1-yl)pyridin-3-yl]-5-trifluoromethyl-1-(3-methoxybenzyl)-1H-pyrrolo[2,3-b]pyridine-2-carboxamide
49  N-[6-(azetidin-1-yl)pyridin-3-yl]-5-trifluoromethyl-1-(3-chlorobenzyl)-1H-pyrrolo[2,3-b]pyridine-2-carboxamide
50  N-[6-(azetidin-1-yl)pyridin-3-yl]-5-trifluoromethyl-1-(3-trifluoromethyloxy)benzyl-1H-pyrrolo[2,3-b]pyridine-2-carboxamide
51  N-[6-(azetidin-1-yl)pyridin-3-yl]-5-trifluoromethyl-1-(4-methoxybenzyl)-1H-pyrrolo[2,3-b]pyridine-2-carboxamide
52  N-[6-(azetidin-1-yl)pyridin-3-yl]-5-trifluoromethyl-1-[(3-chloro-5-(trifluoromethyl)]benzyl-1H-pyrrolo[2,3-b]pyridine-2-carboxamide
53  N-[6-(azetidin-1-yl)pyridin-3-yl]-5-fluoro-1-benzyl-1H-pyrrolo[2,3-b]pyridine-2-carboxamide
54  N-[6-(azetidin-1-yl)pyridin-3-yl]-5-fluoro-1-(2-fluorobenzyl)-1H-pyrrolo[2,3-b]pyridine-2-carboxamide
55  N-[6-(azetidin-1-yl)pyridin-3-yl]-5-fluoro-1-(4-fluorobenzyl)-1H-pyrrolo[2,3-b]pyridine-2-carboxamide
56  N-[6-(azetidin-1-yl)pyridin-3-yl]-5-fluoro-1-(3-trifluoromethyl)benzyl-1H-pyrrolo[2,3-b]pyridine-2-carboxamide
57  N-[6-(azetidin-1-yl)pyridin-3-yl]-5-fluoro-1-(4-methylbenzyl)-1H-pyrrolo[2,3-b]pyridine-2-carboxamide
58  N-[6-(azetidin-1-yl)pyridin-3-yl]-5-fluoro-1-(3-methylbenzyl)-1H-pyrrolo[2,3-b]pyridine-2-carboxamide
59  N-[6-(azetidin-1-yl)pyridin-3-yl]-5-fluoro-1-(3-methoxybenzyl)-1H-pyrrolo[2,3-b]pyridine-2-carboxamide
60  N-[6-(azetidin-1-yl)pyridin-3-yl]-5-fluoro-1-(3-chlorobenzyl)-1H-pyrrolo[2,3-b]pyridine-2-carboxamide
61  N-[6-(azetidin-1-yl)pyridin-3-yl]-5-fluoro-1-(3-trifluoromethyloxy)benzyl-1H-pyrrolo[2,3-b]pyridine-2-carboxamide
62  N-[6-(azetidin-1-yl)pyridin-3-yl]-5-fluoro-1-(4-methoxybenzyl)-1H-pyrrolo[2,3-b]pyridine-2-carboxamide
63  N-[6-(azetidin-1-yl)pyridin-3-yl]-5-fluoro-1-[(3-chloro-5-(trifluoromethyl)]benzyl-1H-pyrrolo[2,3-b]pyridine-2-carboxamide
64  N-[6-(azetidin-1-yl)pyridin-3-yl]-6-trifluoromethyl-1-benzyl-1H-pyrrolo[2,3-b]pyridine-2-carboxamide
65  N-[6-(azetidin-1-yl)pyridin-3-yl]-6-trifluoromethyl-1-(2-fluorobenzyl)-1H-pyrrolo[2,3-b]pyridine-2-carboxamide
66  N-[6-(azetidin-1-yl)pyridin-3-yl]-6-trifluoromethyl-1-(4-fluorobenzyl)-1H-pyrrolo[2,3-b]pyridine-2-carboxamide
67  N-[6-(azetidin-1-yl)pyridin-3-yl]-6-trifluoromethyl-1-(3-trifluoromethyl)benzyl-1H-pyrrolo[2,3-b]pyridine-2-carboxamide
68  N-[6-(azetidin-1-yl)pyridin-3-yl]-6-trifluoromethyl-1-(4-methylbenzyl)-1H-pyrrolo[2,3-b]pyridine-2-carboxamide
69  N-[6-(azetidin-1-yl)pyridin-3-yl]-6-trifluoromethyl-1-(3-methylbenzyl)-1H-pyrrolo[2,3-b]pyridine-2-carboxamide
70  N-[6-(azetidin-1-yl)pyridin-3-yl]-6-trifluoromethyl-1-(3-methoxybenzyl)-1H-pyrrolo[2,3-b]pyridine-2-carboxamide
71  N-[6-(azetidin-1-yl)pyridin-3-yl]-6-trifluoromethyl-1-(3-chlorobenzyl)-1H-pyrrolo[2,3-b]pyridine-2-carboxamide
72  N-[6-(azetidin-1-yl)pyridin-3-yl]-6-trifluoromethyl-1-(3-trifluoromethyloxy)benzyl-1H-pyrrolo[2,3-b]pyridine-2-carboxamide
73  N-[6-(azetidin-1-yl)pyridin-3-yl]-6-trifluoromethyl-1-(4-methoxybenzyl)-1H-pyrrolo[2,3-b]pyridine-2-carboxamide
74  N-[6-(azetidin-1-yl)pyridin-3-yl]-6-trifluoromethyl-1-[(3-chloro-5-(trifluoromethyl)]benzyl-1H-pyrrolo[2,3-b]pyridine-2-carboxamide
75  N-[6-(azetidin-1-yl)pyridin-3-yl]-1-benzyl-1H-pyrrolo[2,3-b]pyridine-2-carboxamide
76  N-[6-(azetidin-1-yl)pyridin-3-yl]-1-(2-fluorobenzyl)-1H-pyrrolo[2,3-b]pyridine-2-carboxamide
77  N-[6-(azetidin-1-yl)pyridin-3-yl]-(4-fluorobenzyl)-1H-pyrrolo[2,3-b]pyridine-2-carboxamide
78  N-[6-(azetidin-1-yl)pyridin-3-yl]-1-(3-trifluoromethyl)benzyl-1H-pyrrolo[2,3-b]pyridine-2-carboxamide
79  N-[6-(azetidin-1-yl)pyridin-3-yl]-1-(4-methyl benzyl)-1H-pyrrolo[2,3-b]pyridine-2-carboxamide
80  N-[6-(azetidin-1-yl)pyridin-3-yl]-1-(3-methylbenzyl)-1H-pyrrolo[2,3-b]pyridine-2-carboxamide
81  N-[6-(azetidin-1-yl)pyridin-3-yl]-1-(3-methoxybenzyl)-1H-pyrrolo[2,3-b]pyridine-2-carboxamide
82  N-[6-(azetidin-1-yl)pyridin-3-yl]-1-(3-chlorobenzyl)-1H-pyrrolo[2,3-b]pyridine-2-carboxamide
83  N-[6-(azetidin-1-yl)pyridin-3-yl]-1-(3-trifluoromethyloxy)benzyl-1H-pyrrolo[2,3-b]pyridine-2-carboxamide
84  N-[6-(azetidin-1-yl)pyridin-3-yl]-1-(4-methoxybenzyl)-1H-pyrrolo[2,3-b]pyridine-2-carboxamide
85  N-[6-(azetidin-1-yl)pyridin-3-yl]-1-[(3-chloro-5-(trifluoromethyl)]benzyl-1H-pyrrolo[2,3-b]pyridine-2-carboxamide 86  N-[6-(3-hydroxyazetidin-1-yl)pyridin-3-yl]-5-trifluoromethyl-1-(2-fluorobenzyl)-1H-pyrrolo[2,3-b]pyridine-2-carboxamide
87  N-[6-(3-hydroxyazetidin-1-yl)pyridin-3-yl]-5-trifluoromethyl-1-(4-fluorobenzyl)-1H-pyrrolo[2,3-b]pyridine-2-carboxamide
88  N-[6-(3-hydroxyazetidin-1-yl)pyridin-3-yl]-5-trifluoromethyl-1-(3-trifluoromethyl)benzyl-1H-pyrrolo[2,3-b]pyridine-2-carboxamide
89  N-[6-(3-hydroxyazetidin-1-yl)pyridin-3-yl]-5-trifluoromethyl-1-(4-methylbenzyl)-1H-pyrrolo[2,3-b]pyridine-2-carboxamide
90  N-[6-(3-hydroxyazetidin-1-yl)pyridin-3-yl]-5-trifluoromethyl-1-(3-methylbenzyl)-1H-pyrrolo[2,3-b]pyridine-2-carboxamide
91  N-[6-(3-hydroxyazetidin-1-yl)pyridin-3-yl]-5-trifluoromethyl-1-(3-methoxybenzyl)-1H-pyrrolo[2,3-b]pyridine-2-carboxamide
92  N-[6-(3-hydroxyazetidin-1-yl)pyridin-3-yl]-5-trifluoromethyl-1-(3-chlorobenzyl)-1H-pyrrolo[2,3-b]pyridine-2-carboxamide
93  N-[6-(3-hydroxyazetidin-1-yl)pyridin-3-yl]-5-trifluoromethyl-1-(3-trifluoromethyloxy)benzyl-1H-pyrrolo[2,3-b]pyridine-2-carboxamide
94  N-[6-(3-hydroxyazetidin-1-yl)pyridin-3-yl]-5-trifluoromethyl-1-(4-methoxybenzyl)-1H-pyrrolo[2,3-b]pyridine-2-carboxamide
95  N-[6-(3-hydroxyazetidin-1-yl)pyridin-3-yl]-5-trifluoromethyl-1-[(3-chloro-5-(trifluoromethyl)]benzyl-1H-pyrrolo[2,3-b]pyridine-2-carboxamide
96  N-[6-(3-hydroxyazetidin-1-yl)pyridin-3-yl]-6-trifluoromethyl-1-benzyl-1H-pyrrolo[2,3-b]pyridine-2-carboxamide
97  N-[6-(3-hydroxyazetidin-1-yl)pyridin-3-yl]-6-trifluoromethyl-1-(2-fluorobenzyl)-1H-pyrrolo[2,3-b]pyridine-2-carboxamide
98  N-[6-(3-hydroxyazetidin-1-yl)pyridin-3-yl]-6-trifluoromethyl-1-(4-fluorobenzyl)-1H-pyrrolo[2,3-b]pyridine-2-carboxamide
99  N-[6-(3-hydroxyazetidin-1-yl)pyridin-3-yl]-6-trifluoromethyl-1-(3-trifluoromethyl)benzyl-1H-pyrrolo[2,3-b]pyridine-2-carboxamide
100  N-[6-(3-hydroxyazetidin-1-yl)pyridin-3-yl]-6-trifluoromethyl-1-(4-methylbenzyl)-1H-pyrrolo[2,3-b]pyridine-2-carboxamide
101  N-[6-(3-hydroxyazetidin-1-yl)pyridin-3-yl]-6-trifluoromethyl-1-(3-methylbenzyl)-1H-pyrrolo[2,3-b]pyridine-2-carboxamide
102  N-[6-(3-hydroxyazetidin-1-yl)pyridin-3-yl]-6-trifluoromethyl-1-(3-methoxybenzyl)-1H-pyrrolo[2,3-b]pyridine-2-carboxamide
103  N-[6-(3-hydroxyazetidin-1-yl)pyridin-3-yl]-6-trifluoromethyl-1-(3-chlorobenzyl)-1H-pyrrolo[2,3-b]pyridine-2-carboxamide
104  N-[6-(3-hydroxyazetidin-1-yl)pyridin-3-yl]-6-trifluoromethyl-1-(3-trifluoromethyloxy)benzyl-1H-pyrrolo[2,3-b]pyridine-2-carboxamide
105  N-[6-(3-hydroxyazetidin-1-yl)pyridin-3-yl]-6-trifluoromethyl-1-(4-methoxybenzyl)-1H-pyrrolo[2,3-b]pyridine-2-carboxamide
106  N-[6-(3-hydroxyazetidin-1-yl)pyridin-3-yl]-6-trifluoromethyl-1-[(3-chloro-5-(trifluoromethyl)]benzyl-1H-pyrrolo[2,3-b]pyridine-2-carboxamide
107  N-[6-(3-hydroxyazetidin-1-yl)pyridin-3-yl]-5-fluoro-1-benzyl-1H-pyrrolo[2,3-b]pyridine-2-carboxamide
108  N-[6-(3-hydroxyazetidin-1-yl)pyridin-3-yl]-5-fluoro-1-(2-fluorobenzyl)-1H-pyrrolo[2,3-b]pyridine-2-carboxamide
109  N-[6-(3-hydroxyazetidin-1-yl)pyridin-3-yl]-5-fluoro-1-(4-fluorobenzyl)-1H-pyrrolo[2,3-b]pyridine-2-carboxamide
110  N-[6-(3-hydroxyazetidin-1-yl)pyridin-3-yl]-5-fluoro-1-(3-trifluoromethyl)benzyl-1H-pyrrolo[2,3-b]pyridine-2-carboxamide
111  N-[6-(3-hydroxyazetidin-1-yl)pyridin-3-yl]-5-fluoro-1-(4-methylbenzyl)-1H-pyrrolo[2,3-b]pyridine-2-carboxamide
112  N-[6-(3-hydroxyazetidin-1-yl)pyridin-3-yl]-5-fluoro-1-(3-methylbenzyl)-1H-pyrrolo[2,3-b]pyridine-2-carboxamide
113  N-[6-(3-hydroxyazetidin-1-yl)pyridin-3-yl]-5-fluoro-1-(3-methoxybenzyl)-1H-pyrrolo[2,3-b]pyridine-2-carboxamide
114  N-[6-(3-hydroxyazetidin-1-yl)pyridin-3-yl]-5-fluoro-1-(3-chlorobenzyl)-1H-pyrrolo[2,3-b]pyridine-2-carboxamide
115  N-[6-(3-hydroxyazetidin-1-yl)pyridin-3-yl]-5-fluoro-1-(3-trifluoromethyloxy)benzyl-1H-pyrrolo[2,3-b]pyridine-2-carboxamide
116  N-[6-(3-hydroxyazetidin-1-yl)pyridin-3-yl]-5-fluoro-1-(4-methoxybenzyl)-1H-pyrrolo[2,3-b]pyridine-2-carboxamide
117  N-[6-(3-hydroxyazetidin-1-yl)pyridin-3-yl]-5-fluoro-1-[(3-chloro-5-(trifluoromethyl)]benzyl-1H-pyrrolo[2,3-b]pyridine-2-carboxamide
118  N-[6-(3-hydroxyazetidin-1-yl)pyridin-3-yl]-1-benzyl-1H-pyrrolo[2,3-b]pyridine-2-carboxamide
119  N-[6-(3-hydroxyazetidin-1-yl)pyridin-3-yl]-1-(2-fluorobenzyl)-1H-pyrrolo[2,3-b]pyridine-2-carboxamide
120  N-[6-(3-hydroxyazetidin-1-yl)pyridin-3-yl]-(4-fluorobenzyl)-1H-pyrrolo[2,3-b]pyridine-2-carboxamide
121  N-[6-(3-hydroxyazetidin-1-yl)pyridin-3-yl]-1-(3-trifluoromethyl)benzyl-1H-pyrrolo[2,3-b]pyridine-2-carboxamide
122  N-[6-(3-hydroxyazetidin-1-yl)pyridin-3-yl]-1-(4-methylbenzyl)-1H-pyrrolo[2,3-b]pyridine-2-carboxamide
123  N-[6-(3-hydroxyazetidin-1-yl)pyridin-3-yl]-1-(3-methyl benzyl)-1H-pyrrolo[2,3-b]pyridine-2-carboxamide
124  N-[6-(3-hydroxyazetidin-1-yl)pyridin-3-yl]-1-(3-methoxybenzyl)-1H-pyrrolo[2,3-b]pyridine-2-carboxamide
125  N-[6-(3-hydroxyazetidin-1-yl)pyridin-3-yl]-1-(3-chlorobenzyl)-1H-pyrrolo[2,3-b]pyridine-2-carboxamide
126  N-[6-(3-hydroxyazetidin-1-yl)pyridin-3-yl]-1-(3-trifluoromethyloxy)benzyl-1H-pyrrolo[2,3-b]pyridine-2-carboxamide
127  N-[6-(3-hydroxyazetidin-1-yl)pyridin-3-yl]-1-(4-methoxybenzyl)-1H-pyrrolo[2,3-b]pyridine-2-carboxamide
128  N-[6-(3-hydroxyazetidin-1-yl)pyridin-3-yl]-1-[(3-chloro-5-(trifluoromethyl)]benzyl-1H-pyrrolo[2,3-b]pyridine-2-carboxamide
129  N-[6-(azetidin-1-yl)pyridin-3-yl]-5-trifluoromethyl-1-benzyl-1H-pyrrolo[3,2-b]pyridine-2-carboxamide
130  N-[6-(azetidin-1-yl)pyridin-3-yl]-5-trifluoromethyl-1-(2-fluorobenzyl)-1H-pyrrolo[3,2-b]pyridine-2-carboxamide
131  N-[6-(azetidin-1-yl)pyridin-3-yl]-5-trifluoromethyl-1-(4-fluorobenzyl)-1H-pyrrolo[3,2-b]pyridine-2-carboxamide
132  N-[6-(azetidin-1-yl)pyridin-3-yl]-5-trifluoromethyl-1-(3-trifluoromethyl)benzyl-1H-pyrrolo[3,2-b]pyridine-2-carboxamide 133 N-[6-(azetidin-1-yl)pyridin-3-yl]-5-trifluoromethyl-1-(4-methylbenzyl)-1H-pyrrolo[3,2-b]pyridine-2-carboxamide
134 N-[6-(azetidin-1-yl)pyridin-3-yl]-5-trifluoromethyl-1-(3-methylbenzyl)-1H-pyrrolo[3,2-b]pyridine-2-carboxamide
135 N-[6-(azetidin-1-yl)pyridin-3-yl]-5-trifluoromethyl-1-(3-methoxybenzyl)-1H-pyrrolo[3,2-b]pyridine-2-carboxamide
136 N-[6-(azetidin-1-yl)pyridin-3-yl]-5-trifluoromethyl-1-(3-chlorobenzyl)-1H-pyrrolo[3,2-b]pyridine-2-carboxamide
137 N-[6-(azetidin-1-yl)pyridin-3-yl]-5-trifluoromethyl-1-(3-trifluoromethyloxy)benzyl-1H-pyrrolo[3,2-b]pyridine-2-carboxamide
138 N-[6-(azetidin-1-yl)pyridin-3-yl]-5-trifluoromethyl-1-(4-methoxybenzyl)-1H-pyrrolo[3,2-b]pyridine-2-carboxamide
139 N-[6-(azetidin-1-yl)pyridin-3-yl]-5-trifluoromethyl-1-[(3-chloro-5-(trifluoromethyl)]benzyl-1H-pyrrolo[3,2-b]pyridine-2-carboxamide
140 N-[6-(3-hydroxyazetidin-1-yl)pyridin-3-yl]-5-trifluoromethyl-1-benzyl-1H-pyrrolo[3,2-b]pyridine-2-carboxamide
141 N-[6-(3-hydroxyazetidin-1-yl)pyridin-3-yl]-5-trifluoromethyl-1-(2-fluorobenzyl)-1H-pyrrolo[3,2-b]pyridine-2-carboxamide
142 N-[6-(3-hydroxyazetidin-1-yl)pyridin-3-yl]-5-trifluoromethyl-1-(4-fluorobenzyl)-1H-pyrrolo[3,2-b]pyridine-2-carboxamide
143 N-[6-(3-hydroxyazetidin-1-yl)pyridin-3-yl]-5-trifluoromethyl-1-(3-trifluoromethyl)benzyl-1H-pyrrolo[3,2-b]pyridine-2-carboxamide
144 N-[6-(3-hydroxyazetidin-1-yl)pyridin-3-yl]-5-trifluoromethyl-1-(4-methyl benzyl)-1H-pyrrolo[3,2-b]pyridine-2-carboxamide
145 N-[6-(3-hydroxyazetidin-1-yl)pyridin-3-yl]-5-trifluoromethyl-1-(3-methylbenzyl)-1H-pyrrolo[3,2-b]pyridine-2-carboxamide
146 N-[6-(3-hydroxyazetidin-1-yl)pyridin-3-yl]-5-trifluoromethyl-1-(3-methoxybenzyl)-1H-pyrrolo[3,2-b]pyridine-2-carboxamide
147 N-[6-(3-hydroxyazetidin-1-yl)pyridin-3-yl]-5-trifluoromethyl-1-(3-chlorobenzyl)-1H-pyrrolo[3,2-b]pyridine-2-carboxamide
148 N-[6-(3-hydroxyazetidin-1-yl)pyridin-3-yl]-5-trifluoromethyl-1-(3-trifluoromethyloxy)benzyl-1H-pyrrolo[3,2-b]pyridine-2-carboxamide
149 N-[6-(azetidin-1-yl)pyridin-3-yl]-5-trifluoromethyl-1-(4-methoxybenzyl)-1H-pyrrolo[3,2-b]pyridine-2-carboxamide
150 N-[6-(3-hydroxyazetidin-1-yl)pyridin-3-yl]-5-trifluoromethyl-1-[(3-chloro-5-(trifluoromethyl)]benzyl-1H-pyrrolo[3,2-b]pyridine-2-carboxamide
151 N-[6-(azetidin-1-yl)pyridin-3-yl]-1-benzyl-1H-pyrrolo[2,3-c]pyridine-2-carboxamide
152 N-[6-(azetidin-1-yl)pyridin-3-yl]-1-(2-fluorobenzyl)-1H-pyrrolo[2,3-c]pyridine-2-carboxamide
153 N-[6-(azetidin-1-yl)pyridin-3-yl]-(4-fluorobenzyl)-1H-pyrrolo[2,3-c]pyridine-2-carboxamide
154 N-[6-(azetidin-1-yl)pyridin-3-yl]-1-(3-trifluoromethyl)benzyl-1H-pyrrolo[2,3-c]pyridine-2-carboxamide
155 N-[6-(azetidin-1-yl)pyridin-3-yl]-1-(4-methylbenzyl)-1H-pyrrolo[2,3-c]pyridine-2-carboxamide
156 N-[6-(azetidin-1-yl)pyridin-3-yl]-1-(3-methylbenzyl)-1H-pyrrolo[2,3-c]pyridine-2-carboxamide
157 N-[6-(azetidin-1-yl)pyridin-3-yl]-1-(3-methoxybenzyl)-1H-pyrrolo[2,3-c]pyridine-2-carboxamide
158 N-[6-(azetidin-1-yl)pyridin-3-yl]-1-(3-chlorobenzyl)-1H-pyrrolo[2,3-c]pyridine-2-carboxamide
159 N-[6-(azetidin-1-yl)pyridin-3-yl]-1-(3-trifluoromethyloxy)benzyl-1H-pyrrolo[2,3-c]pyridine-2-carboxamide
160 N-[6-(azetidin-1-yl)pyridin-3-yl]-1-[(3-chloro-5-(trifluoromethyl)]benzyl-1H-pyrrolo[2,3-c]pyridine-2-carboxamide
161 N-[6-(3-hydroxyazetidin-1-yl)pyridin-3-yl]-1-benzyl-1H-pyrrolo[2,3-c]pyridine-2-carboxamide
162 N-[6-(3-hydroxyazetidin-1-yl)pyridin-3-yl]-1-(2-fluorobenzyl)-1H-pyrrolo[2,3-c]pyridine-2-carboxamide
163 N-[6-(3-hydroxyazetidin-1-yl)pyridin-3-yl]-(4-fluorobenzyl)-1H-pyrrolo[2,3-c]pyridine-2-carboxamide
164 N-[6-(3-hydroxyazetidin-1-yl)pyridin-3-yl]-1-(3-trifluoromethyl)benzyl-1H-pyrrolo[2,3-c]pyridine-2-carboxamide
165 N-[6-(3-hydroxyazetidin-1-yl)pyridin-3-yl]-1-(4-methylbenzyl)-1H-pyrrolo[2,3-c]pyridine-2-carboxamide
166 N-[6-(3-hydroxyazetidin-1-yl)pyridin-3-yl]-1-(3-methylbenzyl)-1H-pyrrolo[2,3-c]pyridine-2-carboxamide
167 N-[6-(3-hydroxyazetidin-1-yl)pyridin-3-yl]-1-(3-methoxybenzyl)-1H-pyrrolo[2,3-c]pyridine-2-carboxamide
168 N-[6-(3-hydroxyazetidin-1-yl)pyridin-3-yl]-1-(3-chlorobenzyl)-1H-pyrrolo[2,3-c]pyridine-2-carboxamide
169 N-[6-(3-hydroxyazetidin-1-yl)pyridin-3-yl]-1-(3-trifluoromethyloxy)benzyl-1H-pyrrolo[2,3-c]pyridine-2-carboxamide
170 N-[6-(3-hydroxyazetidin-1-yl)pyridin-3-yl]-1-[(3-chloro-5-(trifluoromethyl)]benzyl-1H-pyrrolo[2,3-c]pyridine-2-carboxamide
171 3-[[5-[[[1-(3-fluorobenzyl)-5-trifluoromethyl-1H-pyrrolo[2,3-b]pyridin-2-yl]carbonyl]amino]pyridin-2-yl]amino]ethyl propionate
172 N-[6-(3-methoxyazetidin-1-yl)pyridin-3-yl]-5-trifluoromethyl-1-(3-fluorobenzyl)-1H-pyrrolo[2,3-b]pyridine-2-carboxamide
173 N-[6-[3-(cyclopropyl methyloxy)azetidin-1-yl]pyridin-3-yl]-5-trifluoromethyl-1-(3-fluorobenzyl)-1H-pyrrolo[2,3-b]pyridine-2-carboxamide Among the compounds of general formula (I) according to the invention, we may also mention the following compounds:
1. N-[(6-Methylamino)pyridin-3-yl]-5-trifluoromethyl-1-(3-fluorobenzyl)-1H-pyrrolo[2,3-b]pyridine-2-carboxamide
2. N-(6-N,N-dimethylamino-5-methylpyridin-3-yl)-5-trifluoromethyl-1-(3-fluorobenzyl)-1H-pyrrolo[2,3-b]pyridine-2-carboxamide
3. N-(6-N,N-dimethylamino-4-methylpyridin-3-yl)-5-trifluoromethyl-1-(3-fluorobenzyl)-1H-pyrrolo[2,3-b]pyridine-2-carboxamide
4. N-(6-N,N-dimethylamino-5-trifluoromethyl-pyridin-3-yl)-5-trifluoromethyl-1-(3-fluorobenzyl)-1H-pyrrolo[2,3-b]pyridine-2-carboxamide
5. N-[6-(Pyrrolidin-1-yl)pyridin-3-yl]-5-fluoro-1-(3-fluorobenzyl)-1H-pyrrolo[2,3-b]pyridine-2-carboxamide
6. N-[6-(Pyrrolidin-1-yl)pyridin-3-yl]-5-trifluoromethyl-1-(3-fluorobenzyl)-1H-pyrrolo[2,3-b]pyridine-2-carboxamide
7. N-[5-(Pyrrolidin-1-yl)pyrazin-2-yl]-5-trifluoromethyl-1-(3-fluorobenzyl)-1H-pyrrolo[2,3-b]pyridine-2-carboxamide
8. N-[6-(Dimethylamino)pyridazin-3-yl]-5-trifluoromethyl-1-(3-fluorobenzyl)-1H-pyrrolo[2,3-b]pyridine-2-carboxamide 9. N-[6-(pyrrolidin-1-yl)pyridin-3-yl]-5-trifluoromethyl-1-[(4-pyridyl)methyl]-1H-pyrrolo[2,3-b]pyridine-2-carboxamide
10. N-[6-(Isopropylamino)pyridin-3-yl]-5-trifluoromethyl-1-(3-fluorobenzyl)-1H-pyrrolo[2,3-b]pyridine-2-carboxamide
11. N-[6-(3-hydroxypyrrolidin-1-yl)pyridin-3-yl]-5-trifluoromethyl-1-(3-fluorobenzyl)-1H-pyrrolo[2,3-b]pyridine-2-carboxamide
12. N-[6-(3,3-difluoropyrrolidin-1-yl)pyridin-3-yl]-5-trifluoromethyl-1-(3-fluorobenzyl)-1H-pyrrolo[2,3-b]pyridine-2-carboxamide
13. N-[6-(dimethylamino)pyridin-3-yl]-5-trifluoromethyl-1-(3-fluorobenzyl)-1H-pyrrolo[2,3-b]pyridine-2-carboxamide
14. N-[6-(cis-2,5-dimethylpyrrolidin-1-yl)pyridin-3-yl]-5-trifluoromethyl-1-(3-fluorobenzyl)-1H-pyrrolo[2,3-b]pyridine-2-carboxamide
15. N-[6-(azetidin-1-yl)pyridin-3-yl]-5-trifluoromethyl-1-(3-fluorobenzyl)-1H-pyrrolo[2,3-b]pyridine-2-carboxamide
16. N-[6-(Pyrrolidin-1-yl)pyridin-3-yl]-5-trifluoromethyl-1-(3-fluorobenzyl)-1H-pyrrolo[3,2-b]pyridine-2-carboxamide
17. N-[6-(2-(S)-carboxypyrrolidin-1-yl)pyridin-3-yl]-5-trifluoromethyl-1-(3-fluorobenzyl)-1H-pyrrolo[2,3-b]pyridine-2-carboxamide
18. N-[6-(2-(S)-tertbutyloxycarbonylpyrrolidin-1-yl)pyridin-3-yl]-5-trifluoromethyl-1-(3-fluorobenzyl)-1H-pyrrolo[2,3-b]pyridine-2-carboxamide
19. N-[6-(3,3-difluoroazetidin-1-yl)pyridin-3-yl]-5-trifluoromethyl-1-(3-fluorobenzyl)-1H-pyrrolo[2,3-b]pyridine-2-carboxamide
20. N-[6-(3-hydroxyazetidin-1-yl)pyridin-3-yl]-5-trifluoromethyl-1-(3-fluorobenzyl)-1H-pyrrolo[2,3-b]pyridine-2-carboxamide
21. N-[4-methyl-6-dimethylaminopyridin-3-yl]-5-trifluoromethyl-1-(3-fluorobenzyl)-1H-pyrrolo[2,3-b]pyridine-2-carboxamide
22. N-[4-methyl-6-(pyrrolidin-1-yl)pyridin-3-yl]-6-trifluoromethyl-1-(3-fluorobenzyl)-1H-pyrrolo[2,3-b]pyridine-2-carboxamide
23. N-[6-(3-methoxypyrrolidin-1-yl)pyridin-3-yl]-5-trifluoromethyl-1-(3-fluorobenzyl)-1H-pyrrolo[2,3-b]pyridine-2-carboxamide
24. N-[4-methyl-6-dimethylaminopyridin-3-yl]-5-trifluoromethyl-1-[(pyridin-4-yl)methyl]-1H-pyrrolo[2,3-b]pyridine-2-carboxamide
25. N-[4-methyl-6-(pyrrolidin-1-yl)pyridin-3-yl]-5-trifluoromethyl-1-(3-fluorobenzyl)-1H-pyrrolo[2,3-b]pyridine-2-carboxamide
26. N-[4-methyl-6-(pyrrolidin-1-yl)pyridin-3-yl]-6-trifluoromethyl-1-[(pyridin-4-yl)methyl]-1H-pyrrolo[2,3-b]pyridine-2-carboxamide
27. N-[4-methyl-6-(pyrrolidin-1-yl)pyridin-3-yl]-5-trifluoromethyl-1-[(pyridin-4-yl)methyl]-1H-pyrrolo[2,3-b]pyridine-2-carboxamide
28. N-[4-methyl-6-(methylamino)pyridin-3-yl]-5-trifluoromethyl-1-[(pyridin-4-yl)methyl]-1H-pyrrolo[2,3-b]pyridine-2-carboxamide
29. N-[4-methoxy-6-(pyrrolidin-1-yl)pyridin-3-yl]-5-trifluoromethyl-1-[(pyridin-4-yl)methyl]-1H-pyrrolo[2,3-b]pyridine-2-carboxamide
30. N-[6-(azetidin-1-yl)pyridin-3-yl]-5-trifluoromethyl-1-[(pyridin-4-yl)methyl]-1H-pyrrolo[2,3-b]pyridine-2-carboxamide
31. N-[6-(acetylamino)pyridin-3-yl]-5-trifluoromethyl-1-(3-fluorobenzyl)-1H-pyrrolo[2,3-b]pyridine-2-carboxamide
32. N-[6-aminopyridin-3-yl]-5-trifluoromethyl-1-(3-fluorobenzyl)-1H-pyrrolo[2,3-b]pyridine-2-carboxamide
33. N-[6-(pyrrolidin-1-yl)pyridin-3-yl]-6-trifluoromethyl-1-(3-fluorobenzyl)-1H-pyrrolo[2,3-b]pyridine-2-carboxamide
34. N-[6-(pyrrolidin-1-yl)-4-(trifluoromethyl)pyridin-3-yl]-5-trifluoromethyl-1-(3-fluorobenzyl)-1H-pyrrolo[2,3-b]pyridine-2-carboxamide
35. N-[5-fluoro-6-(dimethylamino)pyridin-3-yl]-5-trifluoromethyl-1-(3-fluorobenzyl)-1H-pyrrolo[2,3-b]pyridine-2-carboxamide
36. N-[2-(dimethylamino)pyrimidin-5-yl]-5-trifluoromethyl-1-(3-fluorobenzyl)-1H-pyrrolo[2,3-b]pyridine-2-carboxamide
37. N-[6-(3-azabicyclo[3.2.0]hept-3-yl)pyridin-3-yl]-5-trifluoromethyl-1-(3-fluorobenzyl)-1H-pyrrolo[2,3-b]pyridine-2-carboxamide
38. N-[6-(3-azabicyclo[3.1.0]hex-3-yl)pyridin-3-yl]-5-trifluoromethyl-1-(3-fluorobenzyl)-1H-pyrrolo[2,3-b]pyridine-2-carboxamide
39. N-[6-(3-azabicyclo[3.1.0]hex-3-yl)pyridin-3-yl]-5-fluoro-1-(3-fluorobenzyl)-1H-pyrrolo[2,3-b]pyridine-2-carboxamide
40. 3-[[5-[[[1-(3-fluorobenzyl)-5-trifluoromethyl-1H-pyrrolo[2,3-b]pyridin-2-yl]carbonyl]amino]pyridin-2-yl]amino]propionic acid
41. N-[6-(3-hydroxypropylamino)pyridin-3-yl]-5-trifluoromethyl-1-(3-fluorobenzyl)-1H-pyrrolo[2,3-b]pyridine-2-carboxamide
43. N-[6-(azetidin-1-yl)pyridin-3-yl]-5-trifluoromethyl-1-(2-fluorobenzyl)-1H-pyrrolo[2,3-b]pyridine-2-carboxamide
44. N-[6-(azetidin-1-yl)pyridin-3-yl]-5-trifluoromethyl-1-(4-fluorobenzyl)-1H-pyrrolo[2,3-b]pyridine-2-carboxamide
45. N-[6-(azetidin-1-yl)pyridin-3-yl]-5-trifluoromethyl-1-(3-trifluoromethyl)benzyl-1H-pyrrolo[2,3-b]pyridine-2-carboxamide
46. N-[6-(azetidin-1-yl)pyridin-3-yl]-5-trifluoromethyl-1-(4-methylbenzyl)-1H-pyrrolo[2,3-b]pyridine-2-carboxamide
48. N-[6-(azetidin-1-yl)pyridin-3-yl]-5-trifluoromethyl-1-(3-methoxybenzyl)-1H-pyrrolo[2,3-b]pyridine-2-carboxamide
49. N-[6-(azetidin-1-yl)pyridin-3-yl]-5-trifluoromethyl-1-(3-chlorobenzyl)-1H-pyrrolo[2,3-b]pyridine-2-carboxamide
50. N-[6-(azetidin-1-yl)pyridin-3-yl]-5-trifluoromethyl-1-(3-trifluoromethyloxy)benzyl-1H-pyrrolo[2,3-b]pyridine-2-carboxamide
51. N-[6-(azetidin-1-yl)pyridin-3-yl]-5-trifluoromethyl-1-(4-methoxybenzyl)-1H-pyrrolo[2,3-b]pyridine-2-carboxamide
62. N-[6-(azetidin-1-yl)pyridin-3-yl]-5-fluoro-1-(4-methoxybenzyl)-1H-pyrrolo[2,3-b]pyridine-2-carboxamide
67. N-[6-(azetidin-1-yl)pyridin-3-yl]-6-trifluoromethyl-1-(3-trifluoromethyl)benzyl-1H-pyrrolo[2,3-b]pyridine-2-carboxamide
68. N-[6-(azetidin-1-yl)pyridin-3-yl]-6-trifluoromethyl-1-(4-methylbenzyl)-1H-pyrrolo[2,3-b]pyridine-2-carboxamide
71. N-[6-(azetidin-1-yl)pyridin-3-yl]-6-trifluoromethyl-1-(3-chlorobenzyl)-1H-pyrrolo[2,3-b]pyridine-2-carboxamide 75. N-[6-(azetidin-1-yl)pyridin-3-yl]-1-benzyl-1H-pyrrolo[2,3-b]pyridine-2-carboxamide
78. N-[6-(azetidin-1-yl)pyridin-3-yl]-1-(3-trifluoromethyl)benzyl-1H-pyrrolo[2,3-b]pyridine-2-carboxamide
81. N-[6-(azetidin-1-yl)pyridin-3-yl]-1-(3-methoxybenzyl)-1H-pyrrolo[2,3-b]pyridine-2-carboxamide
84. N-[6-(azetidin-1-yl)pyridin-3-yl]-1-(4-methoxybenzyl)-1H-pyrrolo[2,3-b]pyridine-2-carboxamide
115. N-[6-(3-hydroxyazetidin-1-yl)pyridin-3-yl]-5-fluoro-1-(3-trifluoromethyloxy)benzyl-1H-pyrrolo[2,3-b]pyridine-2-carboxamide
116. N-[6-(3-hydroxyazetidin-1-yl)pyridin-3-yl]-5-fluoro-1-(4-methoxybenzyl)-1H-pyrrolo[2,3-b]pyridine-2-carboxamide
117. N-[6-(3-hydroxyazetidin-1-yl)pyridin-3-yl]-5-fluoro-1-[(3-chloro-5-(trifluoromethyl)]benzyl-1H-pyrrolo[2,3-b]pyridine-2-carboxamide
124. N-[6-(3-hydroxyazetidin-1-yl)pyridin-3-yl]-1-(3-methoxybenzyl)-1H-pyrrolo[2,3-b]pyridine-2-carboxamide
125. N-[6-(3-hydroxyazetidin-1-yl)pyridin-3-yl]-1-(3-chlorobenzyl)-1H-pyrrolo[2,3-b]pyridine-2-carboxamide
129. N-[6-(azetidin-1-yl)pyridin-3-yl]-5-trifluoromethyl-1-benzyl-1H-pyrrolo[3,2-b]pyridine-2-carboxamide
130. N-[6-(azetidin-1-yl)pyridin-3-yl]-5-trifluoromethyl-1-(2-fluorobenzyl)-1H-pyrrolo[3,2-b]pyridine-2-carboxamide
131. N-[6-(azetidin-1-yl)pyridin-3-yl]-5-trifluoromethyl-1-(4-fluorobenzyl)-1H-pyrrolo[3,2-b]pyridine-2-carboxamide
134. N-[6-(azetidin-1-yl)pyridin-3-yl]-5-trifluoromethyl-1-(3-methylbenzyl)-1H-pyrrolo[3,2-b]pyridine-2-carboxamide
135. N-[6-(azetidin-1-yl)pyridin-3-yl]-5-trifluoromethyl-1-(3-methoxybenzyl)-1H-pyrrolo[3,2-b]pyridine-2-carboxamide
138. N-[6-(azetidin-1-yl)pyridin-3-yl]-5-trifluoromethyl-1-(4-methoxybenzyl)-1H-pyrrolo[3,2-b]pyridine-2-carboxamide
164. N-[6-(3-hydroxyazetidin-1-yl)pyridin-3-yl]-1-(3-trifluoromethyl)benzyl-1H-pyrrolo[2,3-c]pyridine-2-carboxamide
165. N-[6-(3-hydroxyazetidin-1-yl)pyridin-3-yl]-1-(4-methylbenzyl)-1H-pyrrolo[2,3-c]pyridine-2-carboxamide Hereinafter, by "leaving group", we mean a group that can easily be cleaved from a molecule by rupture of a heterolytic bond, with departure of an electron pair. This group can thus be replaced easily by another group during a substitution reaction, for example. Said leaving groups are, for example, the halogens or an activated hydroxyl group such as a methanesulfonate, benzenesulfonate, p-toluenesulfonate, triflate, acetate, etc. Examples of leaving groups as well as references for their preparation are given in "Advances in Organic Chemistry", J. March, 5$^{th}$ Edition, Wiley Interscience, 2001.

In accordance with the invention, the compounds of general formula (I) can be prepared according to the method shown below in Scheme 1.

According to Scheme 1, the compounds of general formula (IV) can be obtained by reaction of a compound of general formula (II) in which X is as defined in general formula (I) and B represents a $C_1$-$C_6$-alkoxyl group, with a compound of general formula (III), in which Y and n are as defined in general formula (I) and GP represents a leaving group or GP represents a hydroxyl group.

In Scheme 1, the compounds of general formula (II), when their method of preparation is not described, are commercially available, described in the literature or prepared by analogy with numerous methods described in the literature (P. Roy et al. *Synthesis* 2005, 16, 2751-2757; N. Lahance et al. *Synthesis* 2005, 15, 2571-2577; C. Barberis et al. *Tetrahedron Lett* 2005, 46(51), 8877-8880; T. Lomberget *Synlett* 2005, 13, 2080-2082; 1909; M. Nazare et al. *Angew Chem Int Ed* 2004, 43(34), 4526-4528; P. M. Fresneda et al. *Tetrahedron Lett* 2000, 41 (24), 4777-4780).

When the compound of general formula (III) is defined such that n is equal to 1, 2 or 3 and GP represents a leaving group such as a chlorine, bromine or iodine atom, the reaction can be carried out in the presence of a base such as sodium hydride or potassium carbonate, in a polar solvent such as dimethylformamide, dimethylsulfoxide or acetone (n=1: Kolasa T., *Bioorg. Med. Chem.* 1997, 5 (3) 507, n=2: Abramovitch R., *Synth. Commun.*, 1995, 25(1), 1).

When the compound of general formula (III) is defined such that n is equal to 1, 2 or 3 and GP represents a hydroxyl group, the compounds of general formula (IV) can be obtained by reaction of the compound of general formula (II) with a compound of general formula (III) in the presence of a phosphine such as, for example, triphenylphosphine and a reagent such as, for example, diethyl azodicarboxylate in solution in a solvent such as dichloromethane or tetrahydrofuran (O. Mitsunobu, *Synthesis,* 1981, 1-28). Similarly, the compounds of general formula (IV) can be obtained by reaction of the compound of general formula (II) with a compound of general formula (III) in the presence of a phosphine supported on a resin and a reagent such as, for example, diisopropyl azodicarboxylate in solution in a solvent such as dichloromethane or tetrahydrofuran.

Scheme 1

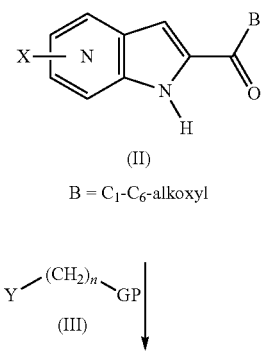

(II)

B = $C_1$-$C_6$-alkoxyl

Y—(CH$_2$)$_n$—GP (III)

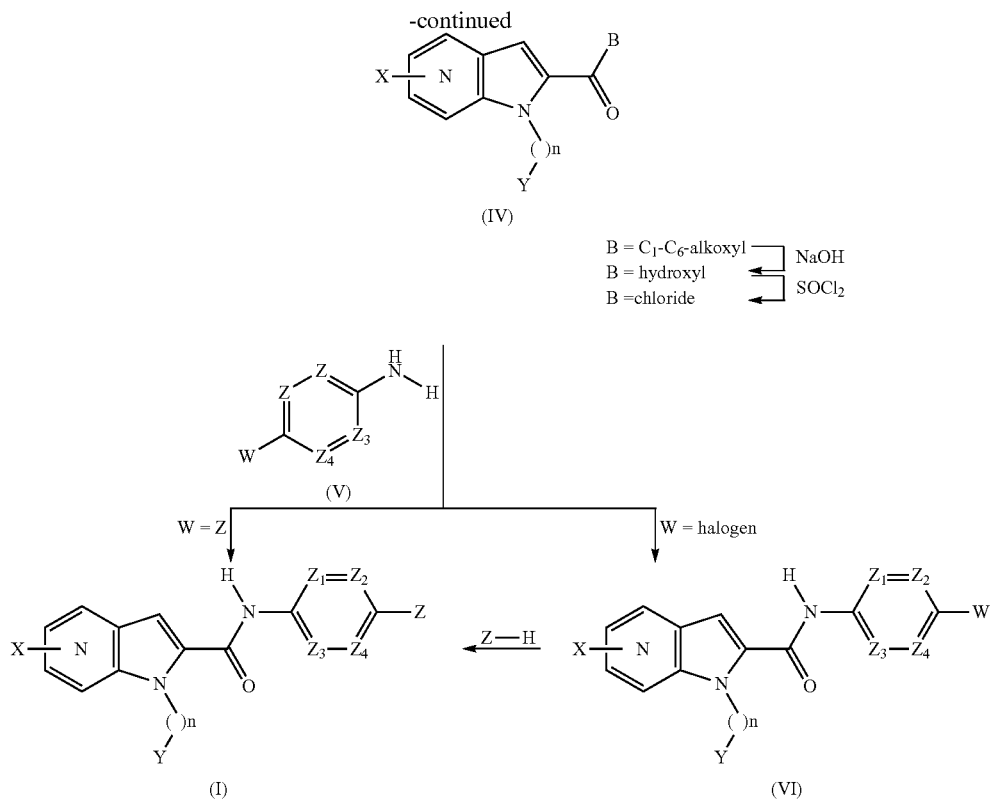

When the compound of general formula (III) is defined such that n is equal to 0 and GP represents a leaving group such as a chlorine, bromine or iodine atom, the reaction can be carried out by application and adaptation of the methods described by S. L. Buchwald et al. (*J. Am. Chem. Soc.,* 2001, 123, 7727 and 2002, 124, 11684), preferably under an inert atmosphere in a basic medium, for example in the presence of potassium triphosphate, in the presence of a copper salt such as copper iodide, optionally in the presence of an additive such as N,N'-dimethylcyclohexane-1,2-diamine, the whole in an organic solvent such as toluene.

The compound of general formula (IV), for which B represents a $C_1$-$C_6$-alkoxy group, can be converted to a compound of general formula (IV), where B represents a hydroxyl group, by the action of a base such as sodium hydroxide or potassium hydroxide in solution in a solvent such as ethanol. The compound of general formula (IV), where B represents a hydroxyl group, can then be converted to a compound of general formula (IV), where B represents a chlorine atom, by the action of a chlorinating agent such as thionyl chloride in a solvent such as dichloromethane.

The compound of general formula (VI) can then be obtained, for example, by reaction of a compound of general formula (IV) where B is a chlorine atom, as obtained above, with an amine of general formula (V), in which $Z_1$, $Z_2$, $Z_3$, $Z_4$ are as defined in general formula (I) and W corresponds to a halogen such as a chlorine atom, in a solvent such as dichloroethane, toluene or tetrahydrofuran.

The compound of general formula (VI) can also be obtained by reaction of a compound of general formula (IV) where B is a hydroxyl group, as obtained above, with an amine of general formula (V), in which $Z_1$, $Z_2$, $Z_3$, $Z_4$ are as defined in general formula (I) and W corresponds to a halogen atom such as a chlorine atom, in the presence of a coupling agent such as diethyl cyanophosphonate or N-(3-dimethylaminopropyl)-N'-ethylcarbodiimide, optionally in the presence of a base such as triethylamine, in a solvent such as dimethylformamide.

The compound of general formula (I) can be obtained, for example, by reaction of a compound of general formula (IV) where B is a chlorine atom, as obtained above, with an amine of general formula (V), in which W=Z and Z, $Z_1$, $Z_2$, $Z_3$, $Z_4$ are as defined in general formula (I), in a solvent such as dichloroethane, toluene or tetrahydrofuran.

The compound of general formula (I) can also be obtained by reaction of a compound of general formula (IV) where B is a hydroxyl group, as obtained above, with an amine of general formula (V), in which W=Z and Z, $Z_1$, $Z_2$, $Z_3$, $Z_4$ are as defined in general formula (I), in the presence of a coupling agent such as diethylcyanophosphonate or N-(3-dimethylaminopropyl)-N'-ethylcarbodiimide, and optionally in the presence of a base such as triethylamine, in a solvent such as dimethylformamide.

The compound of general formula (I) can also be obtained by reaction of a compound of general formula (VI) in the presence of an amine of formula Z-H, in which Z is as defined in general formula (I), without solvent or in a solvent such as N-methylpyrrolidone, or alternatively by application and adaptation of the methods described by S. L. Buchwald et al. (*J. Am. Chem. Soc.,* 2001, 123, 7727 and 2002, 124, 11684), preferably under an inert atmosphere in a basic medium, for example in the presence of potassium triphosphate, in the presence of a copper salt such as copper iodide, optionally in the presence of an additive such as N,N'-dimethylcyclohexane-1,2-diamine, the whole in an organic solvent such as toluene, or alternatively by application and adaptation of the methods described by Hartwig et al. (*Angewandte Chemie,* 2005, 44, 1371-1375), for example in the presence of a base and catalytic amounts of a palladium-based catalyst, such as palladium diacetate, and a phosphine.

The compounds of general formulae (I), (II) and (IV), in which X represents a cyano or an aryl group, can be obtained by a coupling reaction, catalyzed by a metal such as palladium, carried out on the corresponding compounds of general formulae (I), (II) and (IV), in which X represents a leaving group, for example a bromine, according to methods that are described in the literature or that are known by a person skilled in the art.

The compounds of general formulae (I), (II) and (IV), in which X represents a group $C(O)NR_1R_2$, can be obtained from the corresponding compounds of general formulae (I), (II) and (IV), in which X represents a cyano group, according to methods that are described in the literature or are known by a person skilled in the art.

The compounds of general formulae (I), (II), (IV) and (VI) in which X represents a —S(O)-alkyl or —S(O)$_2$-alkyl group can be obtained by oxidation of the corresponding compounds of general formulae (I), (II), (IV) and (VI), in which X represents a $C_1$-$C_6$-thioalkyl group, according to methods that are described in the literature or that are known by a person skilled in the art.

The compounds of general formulae (I), (II), (IV) and (VI) in which X represents a group $NR_1R_2$, $NR_3COR_4$ or $NR_3SO_2R_5$, can be obtained from the corresponding compounds of general formulae (I), (II), (IV) and (VI), in which X represents a nitro group, for example by reduction, then acylation or sulfonylation, according to methods that are described in the literature or that are known by a person skilled in the art.

The compounds of general formulae (I), (II) and (IV), in which X represents a group $NR_1R_2$, $NR_3COR_4$ or $NR_3SO_2R_5$, can be obtained from the corresponding compounds of general formulae (I), (II) and (IV), in which X represents for example a bromine atom, by a coupling reaction respectively with an amine, an amide or a sulfonamide in the presence of a base, a phosphine and a palladium-based catalyst, according to methods that are described in the literature or that are known by a person skilled in the art.

The compounds of general formulae (I), (II) and (IV), in which X represents a group $SO_2NR_1R_2$, can be obtained by a method similar to that described in *Pharmazie* 1990, 45, 346, or according to methods that are described in the literature or that are known by a person skilled in the art.

The compounds of general formula (I) in which Z represents an acyclic amine NRaRb corresponding to a group $NH_2$ can be obtained, according to conditions known by a person skilled in the art and described in the literature (Greene, Wuts, *Protective groups in organic synthesis*, Wiley-Interscience) from precursors of general formula (I) where NRaRb=NH-GP, GP corresponding to a protecting group such as an acetyl or terbutoxycarbonyl group.

The compounds of general formula (I) having a group $CO_2H$ can be obtained, according to conditions known by a person skilled in the art and described in the literature (Greene, Wuts, *Protective groups in organic synthesis*, Wiley-Interscience) from precursors of general formula (I) having a group $CO_2GP$, GP corresponding to a protecting group of carboxylic acid such as a methyl or tertbutyl group.

The compounds of general formula (I) having a group $CH_2OH$ can be obtained, according to conditions known by a person skilled in the art, from compounds of general formula (I) having a group $CO_2$alkyl, for example, by reaction in the presence of a reducing agent such as sodium borohydride in a solvent such as tetrahydrofuran.

The compounds of general formula (III) are commercially available, described in the literature (Carling R. W. et al. *J. Med. Chem.* 2004 (47), 1807-1822 or Russel M. G. N. et al. *J. Med. Chem.* 2005 (48), 1367-1383) or can be obtained using methods known by a person skilled in the art.

The compounds of general formula (V) and the other reactants, when their method of preparation is not described, are commercially available or are described in the literature (WO2005028452, WO2002048152, WO2006040522, WO2004052869, WO2004062665, WO2005035526, WO2004110986, *Heterocycles* 1977, 6(12), 1999-2004, for example).

The invention, according to another of its aspects, also relates to the compounds of formulae (Va), (Vb), (Vc), (Vd), (Ve), (Vf), (Vg) and (Vh). These compounds can be used as synthetic intermediates for the preparation of the compounds of formula (I).

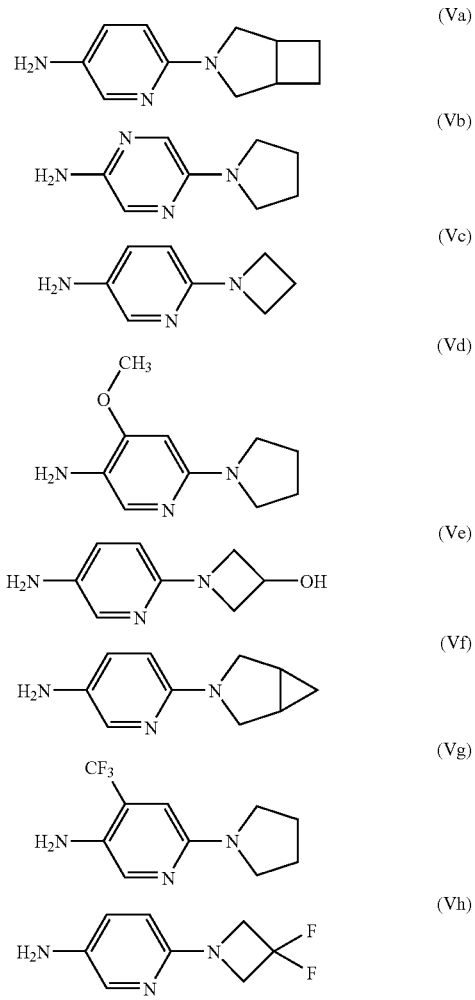

The amines of formulae (Va), (Vb), (Vc), (Vd), (Ve), (Vf), (Vg) and (Vh) can be prepared, for example, according to the method described in example 12.1, by aromatic nucleophilic substitution of a 6-halopyridine precursor, optionally substituted (Vd: by a 4-methoxy group, Vg: by a 4-trifluoromethyl group), with an amine, such as pyrrolidine, for example in a solvent such as ethanol.

The amine (Vb) can be prepared for example according to the method described in Example 7 by heating a solution of commercial 2-amino-5-bromopyrazine in pyrrolidine. Access to the amines Va-h may also necessitate the reduction of a nitro group, for example by catalytic hydrogenation in the presence of a catalyst such as palladium on charcoal, or by all other methods known by a person skilled in the art, for reduction of a nitro group to amine. Access to the amines Va-h may also necessitate, as in the case of the amine (Vg) described in Example 17, the introduction of an amine group by rearrangement of a carboxylic acid group according to the Curtius rearrangement or by all other methods known by a person skilled in the art.

The amines of formulae (Va), (Vb), (Vc), (Vd), (Ve), (Vf), (Vg) and (Vh) have been prepared as a base or a salt of addition to an acid.

Table 1 presents the $^1$H NMR data for these amines.

TABLE 1

| No. | $^1$H NMR, δ (ppm): |
| --- | --- |
| Va | In DMSO D$_6$, δ (ppm): 7.62 (d, 1H); 6.95 (d, 1H); 6.49 (d, 1H); 4.42 (broadened peak, 2H); 3.52 (d, 2H); 2.98 (m, 4H); 2.21 (m, 2H); 1.72 (m, 2H). |
| Vb | In DMSO D$_6$, δ (ppm): 7.5 (d, 1H); 7.32 (d, 1H); 5.15 (s, 2H); 3.25 (m, 4H); 1.88 (m, 4H). |
| Vc | In DMSO D$_6$, δ (ppm): 7.57 (d, 1H); 6.92 (dxd, 1H); 6.2 (d, 1H); 4.46 (broadened peak, 2H); 3.78 (m, 4H); 2.25 (quint., 2H). |
| Vd | In DMSO D$_6$, δ (ppm): 7.16 (s, 1H); 6.61 (s, 1H); 4.52 (broadened peak, 2H); 3.71 (s, 3H); 3.29 (m, 4H); 1.81 (m, 4H). |
| Ve | In DMSO D$_6$, δ (ppm): 7.58 (s, 1H); 6.91 (d, 1H); 6.22 (d, 1H); 5.48 (broadened peak, 1H); 4.48 (broadened peak, 3H); 3.98 (m, 2H); 3.49 (m, 2H); |
| Vf | In DMSO D$_6$, δ (ppm): 7.55 (s, 1H); 6.99 (d, 1H); 6.25 (d, 1H); 4.32 (broadened peak, 2H); 3.51 (d, 2H); 3.11 (m, 2H); 1.6 (m, 1H); 0.66 (m, 1H); 0.2 (m, 1H). |
| Vg (HCl 1:1) | In DMSO D$_6$, δ (ppm): 7.92 (s, 1H); 7.49 (broadened peak, 2H); 7.1 (s, 1H); 3.52 (m, 4H); 2 (m, 4H). |
| Vh | In DMSO D$_6$, δ (ppm): 7.6 (s, 1H); 6.96 (dxd, 1H); 6.4 (d, 1H); 4.67 (s, 2H); 4.2 (t, 4H). |

The following examples describe the preparation of some compounds according to the invention. These examples are not limiting and merely illustrate the present invention. The numbers of the example compounds refer to those given in Table 1. Elemental microanalyses, LC-MS analyses (liquid chromatography coupled to mass spectrometry) IR spectra or NMR spectra confirm the structures of the compounds obtained.

EXAMPLE 1

Compound No. 1 in Table 2

N-[(6-Methylamino)pyridin-3-yl]-5-trifluoromethyl-1-(3-fluorobenzyl)-1H-pyrrolo[2,3-b]pyridine-2-carboxamide

1.1. 5-Trifluoromethyl-1H-pyrrolo[2,3-b]pyridine-2-ethyl carboxylate

Put 0.3 g (1.3 mmol) of 5-trifluoromethyl-1H-pyrrolo[2,3-b]pyridine-2-carboxylic acid (*Angew Chem Int Ed* 2004, 43(34), 4526-4528) and 50 mL of ethanol in a 100-mL flask equipped with a magnetic stirrer. Add, to this solution, 0.5 mL of concentrated sulfuric acid. The reaction mixture is then refluxed for 18 hours. The cooled solution is concentrated to dryness at reduced pressure. The residue is taken up in dichloromethane (100 mL), the organic phase is washed successively with a normal aqueous solution of sodium hydroxide (30 mL), with water (20 mL) and then with a saturated aqueous solution of sodium chloride. It is dried over sodium sulfate and then concentrated at reduced pressure. 0.29 g (1.12 mmol) of the expected product is isolated in the form of a yellow powder.

$^1$H NMR (DMSO D$_6$), δ (ppm): 12.95 (s, NH); 8.8 (d, 1H); 8.6 (d, 1H); 7.3 (s, 1H); 4.4 (q, 2H); 1.35 (t, 3H).

1.2 5-Trifluoromethyl-1-[(3-fluorophenyl)methyl]-1H-pyrrolo[2,3-b]pyridine-2-ethyl carboxylate To a solution of 0.3 g (1.16 mmol) of product obtained in Stage 1.1, in 20 mL of dry tetrahydrofuran, held under an inert atmosphere, add successively, while stirring, 0.23 g (1.74 mmol) of 3-fluorobenzyl alcohol and then 0.46 g (1.74 mmol) of triphenylphosphine. Then add, dropwise, 0.31 g (1.74 mmol) of diethyl azodicarboxylate. The reaction mixture is then stirred for 20 h at room temperature and is then concentrated at reduced pressure. The resultant oil is purified by chromatography on a column of silica gel, eluting with a mixture of heptane and ethyl acetate. 0.34 g (0.93 mmol) of the expected product is isolated.

$^1$H NMR (DMSO D$_6$), δ (ppm): 8.9 (d, 1H); 8.7 (d, 1H); 7.5 (s, 1H); 7.4-6.95 (m, 2H); 6.85 (m, 2H); 5.9 (s, 2H); 4.3 (q, 2H), 1.3 (t, 3H).

1.3 5-Trifluoromethyl-1-[(3-fluorophenyl)methyl]-1H-pyrrolo[2,3-b]pyridine-2-carboxylic acid A solution of 3.15 g (8.6 mmol) of 5-trifluoromethyl-1-[(3-fluorophenyl)methyl]-1H-pyrrolo[2,3-b]pyridine-2-ethyl carboxylate obtained in Stage 1.2 in 100 mL of ethanol and of 26 mL of 2N sodium hydroxide is stirred for four hours under reflux. After this time, the reaction mixture is concentrated at reduced pressure, and then is taken up in 40 mL of water. The reaction mixture is acidified to pH 3 by successive additions of 1N hydrochloric acid. The precipitate is collected by filtration, washed with water and then dried at reduced pressure. Thus, 2.9 g of the expected product is isolated in the form of a white powder, which is used as it is in the next stage.

$^1$H NMR (DMSO D$_6$), δ (ppm): 13.5 (broadened peak, 1H); 8.81 (d, 1H); 8.63 (d, 1H); 7.47 (s, 1H); 7.3 (m, 1H); 7.1-6.8 (m, 3H); 5.94 (s, 2H).

1.4 N-[(6-Methylamino)pyridin-3-yl]-5-trifluoromethyl-1-(3-fluorobenzyl)-1H-pyrrolo[2,3-b]pyridine-2-carboxamide (Compound No. 1 in Table 2)

109 mg (0.89 mmol) of 2-(methylamino)-5-aminopyridine (*J. Med. Chem.* 1994 (37) 18-25) is added to a solution, stirred at 20° C., of 0.2 g (0.59 mmol) of the compound prepared in Stage 1.3, 113 mg (0.59 mmol) of N-(3-dimethylaminopropyl)-N'-ethylcarbodiimide hydrochloride (EDAC) and 79 mg (0.59 mmol) of 1-hydroxy-benzotriazole (HOBT) in 50 mL of DMF. The reaction mixture is stirred for 14 hours at 20° C. and is then poured into 50 mL of water. The mixture is then extracted with 3×30 mL of ethyl acetate. The combined organic phases are washed twice with 20 mL of water, dried over sodium sulfate and then concentrated at reduced pressure. The product obtained is purified by chromatography on a silica column, eluting with a mixture of dichloromethane and methanol. Thus, 54 mg of the expected product is isolated.

m.p.=252-254° C.

¹H NMR (DMSO D₆), δ (ppm): 10.35 (s, 1H); 8.79 (d, 1H); 8.7 (d, 1H); 8.21 (d, 1H); 7.65 (dxd, 1H); 7.49 (s, 1H); 7.27 (m, 1H); 7.1-6.85 (m, 3H); 6.4 (m, 2H); 5.93 (s, 2H); 2.77 (d, 3H).

EXAMPLE 2

Compound No. 2 in Table 2

N-(6-N,N-Dimethylamino-5-methyl-pyridin-3-yl)-5-trifluoromethyl-1-(3-fluorobenzyl)-1H-pyrrolo[2,3-b]pyridine-2-carboxamide hydrochloride (1:1)

2.1 6-N,N-Dimethylamino-5-methyl-3-nitropyridine 0.95 g (5.5 mmol) of 6-chloro-5-methyl-3-nitropyridine, 5 mL (39.8 mmol) of an aqueous solution of dimethylamine at 40% and 2 mL of ethanol are put in a Schlenk tube, equipped with a magnetized bar. The tube is closed and the reaction mixture is stirred at 120° C. for 15 hours. After this time, the tube is cooled, the reaction mixture is concentrated at reduced pressure, and is then taken up in 50 mL of water. The resultant mixture is extracted twice with 30 mL of dichloromethane. The combined organic phases are washed with 50 mL of a saturated aqueous solution of sodium chloride, dried over sodium sulfate and concentrated at reduced pressure. We thus obtain 0.95 g of the expected product in the form of a yellow solid, which will be used as it is in the rest of the synthesis.

¹H NMR (CDCl₃), δ (ppm): 8.84 (d, 1H); 7.98 (d, 1H); 3.1 (s, 6H); 2.3 (s, 3H).

2.2 6-N,N-Dimethylamino-5-methyl-3-aminopyridine

A suspension of 0.94 g (5.2 mmol) of the product obtained in Stage 2.1, 0.5 mL (10.4 mmol) of hydrazine monohydrate and 0.4 g of Raney Nickel in 40 mL of ethanol is stirred for three hours at 20° C. The insoluble matter is removed by filtration on a Celite pad, and the filtrate is concentrated at reduced pressure. We thus obtain 0.8 g of the expected product, which will be used as it is in the rest of the synthesis.

¹H NMR (CDCl₃), δ (ppm): 7.61 (d, 1H); 6.78 (d, 1H); 3.4-3.1 (broadened peak, 2H); 2.65 (s, 6H); 2.19 (s, 3H).

2.3 N-(6-N,N-Dimethylamino-5-methyl-pyridin-3-yl)-5-trifluoromethyl-1-(3-fluorobenzyl)-1H-pyrrolo[2,3-b]pyridine-2-carboxamide hydrochloride (1:1) (compound No. 2 in Table 2)

Compound No. 2 was prepared by a method similar to that described in Stage 1.4, by reacting 0.17 g (1.11 mmol) of the amine obtained in Stage 2.2 with 0.25 g (0.74 mmol) of the acid obtained in Stage 1.3. The product obtained is taken up in 5 mL of 0.1N hydrochloric acid in isopropanol and 5 mL of dichloromethane. The solution is concentrated at reduced pressure, thus isolating 0.23 g of the expected product in the form of hydrochloride.

m.p.=252-257° C.; Hydrochloride (1:1)

¹H NMR (DMSO D₆), δ (ppm): 10.88 (s, 1H); 8.8 (s, 1H); 8.71 (s, 1H); 8.42 (d, 1H); 8.02 (d, 1H); 7.63 (s, 1H); 7.28 (m, 1H); 7.1-6.85 (m, 3H); 5.93 (s, 2H); 2.97 (s, 6H); 2.32 (s, 3H).

EXAMPLE 3

Compound No. 3 in Table 2

N-(6-N,N-Dimethylamino-4-methyl-pyridin-3-yl)-5-trifluoromethyl-1-(3-fluorobenzyl)-1H-pyrrolo[2,3-b]pyridine-2-carboxamide hydrochloride (1:1)

Compound No. 3 was prepared by a method similar to that described in Stage 1.4, by reacting 0.17 g (1.11 mmol) of 6-N,N-dimethylamino-4-methyl-3-aminopyridine (WO2004062665) with 0.25 g (0.74 mmol) of the acid obtained in Stage 1.3. The product obtained is taken up in 3.8 mL of 0.1N hydrochloric acid in isopropanol and 2 mL of dichloromethane. After 15 hours at 20° C., the precipitate is collected by filtration and rinsed with 50 mL of ethyl ether, and is then dried at reduced pressure. 0.15 g of the expected product is thus isolated in the form of hydrochloride.

m.p.=242-247° C.; Hydrochloride (1:1)

¹H NMR (DMSO D₆), δ (ppm): 10.31 (s, 1H); 8.8 (s, 1H); 8.73 (s, 1H); 7.91 (s, 1H); 7.6 (s, 1H); 7.3 (m, 1H); 7.1-6.8 (m, 4H); 5.91 (s, 2H); 3.16 (s, 6H); 2.18 (s, 3H).

EXAMPLE 4

Compound No. 4 in Table 2

N-(6-N,N-Dimethylamino-5-trifluoromethyl-pyridin-3-yl)-5-trifluoromethyl-1-(3-fluorobenzyl)-1H-pyrrolo[2,3-b]pyridine-2-carboxamide hydrochloride (1:1)

Compound No. 4 was prepared by a method similar to that described in Stage 1.4, by reacting 0.15 g (0.74 mmol) of 6-N,N-dimethylamino-5-trifluoromethyl-3-aminopyridine (WO2004110986) with 0.25 g (0.74 mmol) of the acid obtained in Stage 1.3. The product obtained is taken up in 3.8 mL of 0.1N hydrochloric acid in isopropanol and 2 mL of dichloromethane. The solution is concentrated at reduced pressure, thus isolating 0.28 g of the expected product in the form of hydrochloride.

m.p.=213-218° C.; Hydrochloride (1:1)

¹H NMR (DMSO D₆), δ (ppm): 10.81 (s, 1H); 8.75 (m, 3H); 8.31 (d, 1H); 7.61 (s, 1H); 7.3 (m, 1H); 7.1-6.85 (m, 3H); 5.94 (s, 2H); 2.88 (s, 6H).

EXAMPLE 5

Compound No. 5 in Table 2

N-[6-(Pyrrolidin-1-yl)pyridin-3-yl]-5-fluoro-1-(3-fluorobenzyl)-1H-pyrrolo[2,3-b]pyridine-2-carboxamide 5.1 2-Amino-3-iodo-5-fluoropyridine 5 g (44.6 mmol) of 2-amino-5-fluoropyridine, 13.9 g (44.6 mmol) of silver sulfate and 400 mL of ethanol are put in a 500-mL two-necked flask equipped with a magnetic stirrer. Then 11.31 g (44.6 mmol) of iodine powder is added, in small portions. It is stirred at room temperature for 24 hours. The insoluble matter is removed by filtration and is washed with ethanol, and the filtrate is concentrated at reduced pressure. The residue thus obtained is taken up in a mixture of ethyl acetate (200 mL) and sodium carbonate solution (200 mL). After separation, the organic phase is washed successively with a 25% aqueous solution of sodium thiosulfate then with a saturated aqueous solution of sodium chloride, then it is dried over sodium sulfate and concentrated at reduced pressure. The resultant solid is purified by chromatography on a silica column, eluting with a mixture of n-heptane and ethyl acetate. We obtain 2.67 g (11.22 mmol) of the expected product.

¹H NMR (DMSO D₆), δ (ppm): 7.95 (s, 1H); 7.85 (s, 1H); 5.9 (s, NH₂).

5.2 5-Fluoro-1H-pyrrolo[2,3-b]pyridine-2-carboxylic acid 0.5 g (2.10 mmol) of 2-amino-3-iodo-5-fluoropyridine obtained in Stage 5.1, 0.55 g (6.3 mmol) of pyruvic acid, 0.71 g (6.3 mmol) of 1,4-diazabicyclo[2.2.2]octane (DABCO) and 15 mL of anhydrous dimethylformamide are introduced into a 25-mL sealed tube, equipped with a magnetic stirrer and bubbled with argon. After some minutes, 0.05 g (0.22 mmol) of palladium acetate is added. The reaction mixture is stirred and bubbled with argon for 20 minutes, then it is quickly sealed and heated to 100° C. for 2.5 h. The cooled solution is concentrated at reduced pressure. The residue is then taken up in ethyl acetate (100 mL) and water (75 mL). The organic phase is washed with water then extracted with 2×50 mL of aqueous solution of 2N sodium hydroxide. The basic aqueous phases are combined, cooled to 0° C. then acidified by adding hydrochloric acid (pH 3). The mixture is extracted with ethyl acetate (4×50 mL), the combined organic phases are dried over sodium sulfate and then concentrated at reduced pressure. We obtain 0.158 g (0.88 mmol) of the expected product in the form of a yellow powder.

$^1$H NMR (DMSO D$_6$), δ (ppm): 13.2 (s, 1H); 12.4 (s, 1H); 8.4 (d, 1H); 7.95 (dd, 1H); 7.1 (d, 1H).

5.3 5-Fluoro-1H-pyrrolo[2,3-b]pyridine-2-ethyl carboxylate 0.2 g (1.11 mmol) of acid obtained in Stage 5.2 and 10 mL of ethanol are put in a 100-mL flask equipped with a magnetic stirrer. 1 mL of concentrated sulfuric acid is added to the reaction mixture, which is then refluxed for 18 hours. The cooled solution is concentrated to dryness at reduced pressure. The residue is taken up in ethyl acetate (50 mL) and washed successively with normal aqueous solution of sodium hydroxide (2×10 mL), with water (10 mL) and then with a saturated aqueous solution of sodium chloride. The organic phase is dried over sodium sulfate and then concentrated at reduced pressure. 0.21 g of the expected product is isolated.

$^1$H NMR (DMSO D$_6$), δ (ppm): 12.6 (s, NH); 8.4 (d, 1H); 8.0 (dd, 1H); 7.1 (d, 1H); 4.35 (q, 2H); 1.35 (t, 3H).

5.4 5-Fluoro-1-[(3-fluorophenyl)methyl]-1H-pyrrolo[2,3-b]pyridine-2-ethyl carboxylate 0.18 g (1.44 mmol) of 3-fluorobenzyl alcohol then 0.39 g (1.44 mmol) of triphenylphosphine are added successively, while stirring, to a solution of 0.2 g (0.96 mmol) of product obtained in Stage 5.3, in 15 mL of dry tetrahydrofuran, under an inert atmosphere. Then 0.26 g (1.44 mmol) of diethyl azodicarboxylate is added dropwise at 0° C. The reaction mixture is stirred for 20 h at room temperature and is then concentrated at reduced pressure. The resultant oil is purified by chromatography on a column of silica gel, eluting with a mixture of dichloromethane and methanol. 0.26 g (0.82 mmol) of the expected product is isolated.

5.5 5-Fluoro-1-[(3-fluorophenyl)methyl]-1H-pyrrolo[2,3-b]pyridine-2-carboxylic acid A mixture of 1.3 g (4.11 mmol) of 5-fluoro-1-[(3-fluorophenyl)methyl]-1H-pyrrolo[2,3-b]pyridine-2-ethyl carboxylate, obtained in Stage 5.4, in 40 mL of ethanol and of 0.7 g (12.33 mmol) of potassium hydroxide in 2 mL of water is heated for two hours under reflux. After this time, the mixture is concentrated to dryness and taken up in 100 mL of water. The pH of the resultant solution is acidified with additions of concentrated hydrochloric acid solution. The precipitate is collected by filtration, rinsed with water and then it is dried at reduced pressure. In this way we isolate 1.2 g of a beige solid, which will be used in the rest of the synthesis without further purification.

m.p.=197-198° C.

5.6 N-[6-(Pyrrolidin-1-yl)pyridin-3-yl]-5-fluoro-1-(3-fluorobenzyl)-1H-pyrrolo[2,3-b]pyridine-2-carboxamide (compound No. 5 in Table 2)

A solution of 0.4 g (1.39 mmol) of the acid obtained in Stage 5.5 and of 0.25 g (1.53 mmol) of 1,1'-carbonyldiimidazole in 22 mL of dry tetrahydrofuran is stirred for 3 h at 50° C. After this time, a solution of 0.426 g (1.8 mmol) of 3-amino-6-(pyrrolidin-1-yl)pyridine hydrochloride (WO200248152) and 0.3 mL (2.16 mmol) of triethylamine in 6 mL of tetrahydrofuran is added. The reaction mixture is stirred for 15 hours at 30° C. then poured into 100 mL of water. The resultant mixture is extracted with 3×50 mL of ethyl acetate. The organic phases are combined, washed with 50 mL of water, dried over sodium sulfate and then concentrated at reduced pressure. The solid obtained is triturated in 1.5 mL of methanol, then collected by filtration and dried. We thus obtain 0.18 g of a white solid.

m.p.=239-240° C.

N-[6-(Pyrrolidin-1-yl)pyridin-3-yl]-5-fluoro-1-(3-fluorobenzyl)-1H-pyrrolo[2,3-b]pyridine-2-carboxamide hydrochloride (2:3)

The compound obtained is taken up in 3.5 mL of a solution of 0.1N hydrochloric acid in isopropanol. The resultant solid is filtered, then dried at reduced pressure. In this way we isolate 0.12 g of the expected product in the form of hydrochloride.

m.p.=241-242° C.; Hydrochloride (2:3)

$^1$H NMR (DMSO D$_6$), δ (ppm): 10.79 (s, 1H); 8.49 (m, 2H); 8.15 (m, 2H); 7.52 (s, 1H); 7.29 (m, 1H); 7.12-6.8 (m, 4H); 5.9 (s, 2H); 3.51 (m, 4H); 1.98 (m, 4H).

EXAMPLE 6

Compound No. 6 in Table 2

N-[6-(Pyrrolidin-1-yl)pyridin-3-yl]-5-trifluoromethyl-1-(3-fluorobenzyl)-1H-pyrrolo[2,3-b]pyridine-2-carboxamide

6.1 N-(6-Chloropyridin-3-yl)-5-trifluoromethyl-1-(3-fluorobenzyl)-1H-pyrrolo[2,3-b]pyridine-2-carboxamide According to a method similar to that described in Stage 1.4, by reacting 0.85 g (6.65 mmol) of 6-chloro-3-aminopyridine with 1.5 g (4.43 mmol) of the acid obtained in Stage 1.3, we obtain 1.23 g of the expected product in the form of a white powder.

m.p.=212-213° C.

$^1$H NMR (DMSO D$_6$), δ (ppm): 10.9 (s, 1H); 8.75 (m, 3H); 8.19 (dxd, 1H); 7.61 (s, 1H); 7.5 (d, 1H); 7.29 (m, 1H); 7.1-6.8 (m, 3H); 5.96 (s, 2H).

6.2 N-[6-(Pyrrolidin-1-yl)pyridin-3-yl]-5-trifluoromethyl-1-(3-fluorobenzyl)-1H-pyrrolo[2,3-b]pyridine-2-carboxamide (compound No. 6 in Table 2)

A solution of 0.1 g (0.22 mmol) of the product obtained in Stage 6.1, 0.19 mL (0.158 mmol) of pyrrolidine and 0.5 mL of N-methylpyrrolidinone, placed in a sealed tube, is heated in a microwave oven for 20 min at 200° C. and 300 W. 100 mL of water is added to the reaction mixture and it is then extracted three times with 50 mL of ethyl acetate. The organic phases are combined, washed three times with 20 mL of water, dried over sodium sulfate and then concentrated at reduced pressure. The product obtained is then purified by chromatography on a silica column, eluting with a mixture of dichloromethane and methanol, then recrystallized from a mixture of ethyl acetate and heptane. We obtain 60 mg of the expected product in the form of white crystals.

m.p.: 234-236° C.

$^1$H NMR (DMSO D$_6$), δ (ppm): 10.32 (s, 1H); 8.75 (m, 1H); 8.66 (m, 1H); 8.29 (d, 1H); 7.74 (dxd, 1H); 7.5 (s, 1H); 7.29 (m, 1H); 7.1-6.8 (m, 3H); 6.4 (d, 1H); 5.91 (s, 2H); 3.32 (m, 4H); 1.91 (m, 4H).

EXAMPLE 7

Compound No. 7 in Table 2

N-[5-(Pyrrolidin-1-yl)pyrazin-2-yl]-5-trifluoromethyl-1-(3-fluorobenzyl)-1H-pyrrolo[2,3-b]pyridine-2-carboxamide

7.1 2-Amino-5-(pyrrolidin-1-yl)pyrazine (Amine Vb)

A solution of 0.6 g (3.45 mmol) of 2-amino-5-bromopyrazine and of 3 mL (36 mmol) of pyrrolidine, placed in a sealed tube, is heated in a microwave oven for two hours at 180° C. and 200 W. 100 mL of water is added to the reaction mixture and it is extracted three times with 50 mL of ethyl acetate. The organic phases are combined, washed three times with 20 mL of water and then once with 20 mL of a saturated aqueous solution of sodium chloride, dried over sodium sulfate and then concentrated at reduced pressure. The product obtained is then purified by chromatography on a silica column, eluting with a mixture of dichloromethane and methanol. We obtain 0.21 g of the expected compound in the form of a brown solid.

$^1$H NMR (DMSO D$_6$), δ (ppm): 7.5 (d, 1H); 7.32 (d, 1H); 5.15 (s, 2H); 3.25 (m, 4H); 1.88 (m, 4H).

7.2 N-[5-(Pyrrolidin-1-yl)pyrazin-2-yl]-5-trifluoromethyl-1-(3-fluorobenzyl)-1H-pyrrolo[2,3-b]pyridine-2-carboxamide (compound No. 7 in Table 2)

Compound No. 7 was prepared by a method similar to that described in Stage 1.4 by reacting 0.126 g (0.77 mmol) of the amine obtained in Stage 7.1 with 0.2 g (0.59 mmol) of the acid obtained in Stage 1.3. We obtain 96 mg of the expected product in the form of a yellow solid.

m.p.=182-183° C.

$^1$H NMR (DMSO D$_6$), δ (ppm): 10.9 (s, 1H); 8.79 (m, 1H); 8.67 (m, 1H); 8.1 (m, 1H); 7.79 (s, 1H); 7.65 (s, 1H); 7.3 (m, 1H); 7.1-6.85 (m, 3H); 5.98 (s, 2H); 3.41 (m, 4H); 1.95 (m, 4H).

EXAMPLE 8

Compound No. 8 in Table 2

N-[6-(N,N-Dimethylamino)pyridazin-3-yl]-5-trifluoromethyl-1-(3-fluorobenzyl)-1H-pyrrolo[2,3-b]pyridine-2-carboxamide Compound No. 8 was prepared by a method similar to that described in Stage 1.4 by reacting 0.098 g (0.71 mmol) of 3-amino-6-(N,N-dimethylamino)pyridazine (US1977805419) with 0.2 g (0.59 mmol) of the acid obtained in Stage 1.3. We thus obtain 73 mg of the expected product in the form of a solid.

m.p.=224-226° C.

$^1$H NMR (DMSO D$_6$), δ (ppm): 11.3 (s, 1H); 8.8 (m, 1H); 8.71 (m, 1H); 7.89 (d, 1H); 7.72 (s, 1H); 7.35-6.8 (m, 5H); 5.94 (s, 2H); 3.05 (s, 6H).

EXAMPLE 9

Compound No. 9 in Table 2

N-[6-(Pyrrolidin-1-yl)pyridin-3-yl]-5-trifluoromethyl-1-[(4-pyridyl)methyl]-1H-pyrrolo[2,3-b]pyridine-2-carboxamide

9.1 5-Trifluoromethyl-1-[(4-pyridyl)methyl]-1H-pyrrolo[2,3-b]pyridine-2-ethyl carboxylate Add successively, while stirring, 0.63 g (5.81 mmol) of (pyridin-4-yl)methanol then 1.52 g (5.81 mmol) of triphenylphosphine to a solution of 1 g (3.87 mmol) of the product obtained in Stage 1.1, in 20 mL of dry tetrahydrofuran, under an inert atmosphere. Then add, dropwise, 1.01 g (5.81 mmol) of diethyl azodicarboxylate. The reaction mixture is then stirred for 20 h at room temperature and is then concentrated at reduced pressure. The resultant oil is purified by chromatography on a column of silica gel, eluting with a mixture of heptane and ethyl acetate. 1.23 g of the expected product is isolated in the form of a white solid.

$^1$H NMR (DMSO D$_6$), δ (ppm): 8.8 (d, 1H); 8.7 (d, 1H); 8.45 (d, 2H); 7.55 (s, 1H); 6.95 (d, 2H); 5.9 (s, 2H); 4.3 (q, 2H); 1.2 (t, 3H).

9.2 5-Trifluoromethyl-1-[(4-pyridyl)methyl]-1H-pyrrolo[2,3-b]pyridine-2-carboxylic acid A solution of 0.39 g (6.87 mmol) of potassium hydroxide in 2 mL of water is added to a solution, in 30 mL of ethanol, of 0.8 g (2.29 mmol) of 5-trifluoromethyl-1-[(4-pyridyl)methyl]-1H-pyrrolo[2,3-b]pyridine-2-ethyl carboxylate, obtained in Stage 9.1. The mixture is stirred for four hours under reflux. After this time the reaction mixture is concentrated at reduced pressure, and is then taken up in 40 mL of water. The reaction mixture is acidified to pH 5 by successive additions of concentrated hydrochloric acid. The precipitate is collected by filtration, washed with water and then dried at reduced pressure. In this way we isolate 0.54 g of the expected product, in the form of a white powder, which is used as it is in the next stage.

m.p.=302-303° C.

9.3 N-[6-(Pyrrolidin-1-yl)pyridin-3-yl]-]-5-trifluoromethyl-1-[(4-pyridyl)methyl]-1H-pyrrolo[2,3-b]pyridine-2-carboxamide (compound No. 9 in Table 2)

Compound No. 9 was prepared by a method similar to that described in Stage 5.6 by reacting 0.3 g (0.93 mmol) of the acid obtained in Stage 9.2 with 0.286 g (1.21 mmol) of 3-amino-6-(pyrrolidin-1-yl)pyridine hydrochloride (WO200248152), dissolved beforehand in a mixture of 0.2 mL of triethylamine and 5 mL of tetrahydrofuran. In this way we isolate 30 mg of the expected product in the form of a yellow solid.

m.p.=244-245° C.

$^1$H NMR (DMSO D$_6$), δ (ppm): 10.39 (s, 1H); 8.71 (dxd, 2H); 8.41 (dxd, 2H); 8.28 (d, 1H); 7.73 (dxd, 1H); 7.59 (s, 1H); 7 (d, 2H); 6.41 (d, 1H); 5.97 (s, 2H); 3.31 (m, 4H); 1.9 (m, 4H).

EXAMPLE 10

Compound No. 16 in Table 3

N-[6-(Pyrrolidin-1-yl)pyridin-3-yl]-5-trifluoromethyl-1-(3-fluorobenzyl)-1H-pyrrolo[3,2-b]pyridine-2-carboxamide 10.1 3-Amino-2-iodo-6-(trifluoromethyl)pyridine 1.56 g (6.17 mmol) of iodine is added, in several portions, to a mixture, stirred under argon at 20° C., of 1 g (6.17 mmol) of 3-amino-6-trifluoromethylpyridine and 1.25 g (6.17 mmol) of silver sulfate in 40 mL of ethanol. Stirring is maintained for 18 hours. The insoluble matter is removed by filtration and is washed with ethanol, the filtrate is concentrated at reduced pressure, and the residue is taken up in 100 mL of dichloromethane. The organic phase is washed successively with 20 mL of 5% aqueous solution of sodium hydroxide, 40 mL of water and 20 mL of saturated aqueous solution of sodium chloride, dried over sodium sulfate, concentrated at reduced pressure, and then purified by chromatography on a silica column (eluents: heptane-ethyl acetate). In this way we isolate 1.17 g of the expected product, which is used as it is in the rest of the synthesis.

10.2 (5-Trifluoromethyl)pyrrolo[3,2-b]pyridine-2-carboxylic acid 0.5 g (1.74 mmol) of 3-amino-2-iodo-6-(trifluoromethyl)pyridine, obtained in Stage 10.1, 0.45 g (5.21 mmol) of pyruvic acid, 0.51 mL (5.21 mmol) of 1,4-diazabicyclo[2.2.2]octane and 10 mL of dry dimethylformamide are introduced, under argon, into a sealed tube. The solution is degassed for some minutes, then 0.19 g (0.87 mmol) of palladium acetate is added, the tube is closed and it is refluxed at 130° C. for 4 hours. The cooled solution is then concentrated at reduced pressure and the residue is taken up in 100 mL of ethyl acetate. The organic phase is extracted successively with 2×50 mL of an aqueous solution of 2N sodium hydroxide. The basic aqueous phases are combined, cooled to 0° C., acidified with additions of hydrochloric acid and then extracted with 4×50 mL of ethyl acetate. These organic phases are combined, washed with 20 mL of a saturated aqueous solution of sodium chloride, dried over sodium sulfate and then concentrated at reduced pressure. We obtain 0.22 g of product, which is used as it is in the next stage.

10.3 5-(Trifluoromethyl)pyrrolo[3,2-b]pyridine-2-ethyl carboxylate 1 mL (18.71 mmol) of concentrated sulfuric acid is added to a solution of 0.2 g (0.87 mmol) of 5-trifluoromethyl-pyrrolo[3,2-b]pyridine-2-carboxylic acid, obtained in Stage 10.2, in 10 mL of ethanol. It is stirred under reflux for 20 hours then the solution is cooled, and concentrated at reduced pressure. The resultant residue is then taken up in 50 mL of dichloromethane then washed successively with 20 mL of a saturated aqueous solution of sodium bicarbonate, 40 mL of water and 20 mL of saturated aqueous solution of sodium chloride, dried over sodium sulfate and then concentrated at reduced pressure. We obtain 0.19 g of product, which is used as it is in the next stage.

10.4 1-(3-Fluorobenzyl)-5-(trifluoromethyl)pyrrolo[3,2-b]pyridine-2-ethyl carboxylate Add, successively, 0.13 mL (1.16 mmol) of 3-fluorobenzyl alcohol, 0.3 g (1.16 mmol) of triphenylphosphine then 0.2 g (1.16 mmol) of diethyl azodicarboxylate to a solution of 0.2 g (0.77 mL) of 5-(trifluoromethyl)pyrrolo[3,2-b]pyridine-2-ethyl carboxylate, obtained in Stage 10.3, in 120 mL of dry tetrahydrofuran, held at 0° C. under argon. The reaction mixture is stirred for 20 hours at 20° C. and is then concentrated at reduced pressure. The resultant residue is purified by chromatography on a silica column (eluents: heptane-ethyl acetate). In this way we isolate 0.21 g of the expected product in the form of a yellow oil.

10.5 1-(3-Fluorobenzyl)-5-trifluoromethyl-pyrrolo[3,2-b]pyridine-2-carboxylic acid The compound was prepared by a method similar to that described in Stage 9.2 by reacting 0.6 g (1.64 mmol) of the ester obtained in Stage 10.4 with 0.275 g (4.91 mmol) of potassium hydroxide. We obtain 0.47 g of the expected product in the form of a white solid.
m.p.=254-255° C.
LCMS: [MH]$^+$=339; purity 98%

10.6 N-[6-(Pyrrolidin-1-yl)pyridin-3-yl]-5-trifluoromethyl-1-(3-fluorobenzyl)-1H-pyrrolo[3,2-b]pyridine-2-carboxamide (compound No. 16 in Table 3)

Compound No. 10 was prepared by a method similar to that described in Stage 1.4 by reacting 0.25 g (0.74 mmol) of the acid obtained in Stage 10.5 with 0.2 g (0.89 mmol) of 3-amino-6-(pyrrolidin-1-yl)pyridine hydrochloride (WO200248152), dissolved beforehand in a mixture of 0.13 mL of triethylamine and 3 mL of dimethylformamide. In this way we isolate 40 mg of the expected product in the form of a yellow solid.
m.p.=219-220° C.
$^1$H NMR (DMSO D$_6$), δ (ppm): 10.4 (s, 1H); 8.3 (m, 2H); 7.74 (m, 2H); 7.56 (s, 1H); 7.3 (m, 1H); 7.1-6.82 (m, 3H); 6.41 (d, 1H); 5.91 (s, 2H); 3.37 (m, 4H); 1.91 (m, 4H).

EXAMPLE 11

Compound No. 10 in Table 2

N-[6-(Isopropylamino)pyridin-3-yl]-5-trifluoromethyl-1-(3-fluorobenzyl)-1H-pyrrolo[2,3-b]pyridine-2-carboxamide According to a method similar to that described in Stage 6.2, by reacting 0.15 g (0.33 mmol) of N-(6-chloropyridin-3-yl)-5-trifluoromethyl-1-(3-fluorobenzyl)-1H-pyrrolo[2,3-b]pyridine-2-carboxamide, obtained in Stage 6.1, with 0.29 mL (3.34 mmol) of isopropylamine, we obtain 50 mg of the expected product in the form of a light yellow powder.
m.p.=210-212° C.
$^1$H NMR (DMSO D$_6$), δ (ppm): 10.32 (s, 1H); 8.79 (d, 1H); 8.71 (d, 1H); 8.2 (m, 1H); 7.61 (dxd, 1H); 7.51 (s, 1H); 7.31 (m, 1H); 7.12-6.86 (m, 3H); 6.42 (d, 1H); 6.25 (d, 1H); 5.95 (s, 2H); 3.91 (sext., 1H); 1.12 (d, 6H).

EXAMPLE 12

Compound No. 15 in Table 2

N-[6-(Azetidin-1-yl)pyridin-3-yl]-5-trifluoromethyl-1-(3-fluorobenzyl)-1H-pyrrolo[2,3-b]pyridine-2-carboxamide hydrochloride (1:1)

12.1 2-(Azetidin-1-yl)-5-nitropyridine

Add, dropwise, 4.7 g (80.76 mmol) of azetidine to a suspension, stirred at 20° C., of 27.9 g (0.201 mole) of potassium carbonate and 11 g (67.3 mmol) of 2-chloro-5-nitropyridine in 100 mL of dimethylformamide. Stir the mixture for 5 minutes at 20° C., then for 6 hours at 70° C. After this time, the suspension is poured into a mixture of 300 mL of water and 300 mL of ethyl acetate. The aqueous phase is separated, then extracted with 200 mL of ethyl acetate. The organic phases are combined, washed three times with 250 mL of water, then dried over sodium sulfate and concentrated at reduced pressure. We thus obtain 11.7 g of the expected product in the form of a solid.

m.p.=132-134° C.

$^1$H NMR (CDCl$_3$), δ (ppm): 8.92 (d, 1H); 8.09 (dxd, 1H); 6.07 (d, 1H); 4.12 (m, 4H); 2.46 (quint., 2H).

12.2 3-Amino-6-(azetidin-1-yl)-pyridine (Amine Vc)

A suspension of 11.5 g (64.18 mmol) of 2-(azetidin-1-yl)-5-nitropyridine, prepared in the preceding stage, and 1 g of Pd/C at 10% in 400 mL of ethanol is stirred vigorously at 20° C. under 5 atm of hydrogen for 4 hours. After this time, the mixture is filtered on a Celite pad and then concentrated at reduced pressure. We thus obtain 9.3 g of the expected product, which is used as it is in the rest of the synthesis.

$^1$H NMR (DMSO D$_6$), δ (ppm): 7.57 (d, 1H); 6.92 (dxd, 1H); 6.2 (d, 1H); 4.46 (broadened peak, 2H); 3.78 (m, 4H); 2.25 (quint., 2H).

12.3 N-[6-(Azetidin-1-yl)pyridin-3-yl]-5-trifluoromethyl-1-(3-fluorobenzyl)-1H-pyrrolo[2,3-b]pyridine-2-carboxamide (Compound No. 15 in Table 2)

Add, dropwise, 4.26 g (24.83 mmol) of diethyl cyanophosphonate to a solution, stirred at 20° C. under a nitrogen atmosphere, of 7 g (20.69 mmol) of 5-trifluoromethyl-1-[(3-fluorophenyl)methyl]-1H-pyrrolo[2,3-b]pyridine-2-carboxylic acid as obtained in Stage 1.3 and 3.7 g (24.83 mmol) of 3-amino-6-(azetidin-1-yl)-pyridine prepared in the preceding stage in 140 mL of dimethylformamide. Then add, dropwise, 4.6 mL (45.53 mmol) of triethylamine, then stir the reaction mixture for 70 hours at 20° C. After this time, the mixture is concentrated at reduced pressure and then taken up in 700 mL of ethyl acetate and 300 mL of water. The aqueous phase is separated and then extracted with 200 mL of ethyl acetate. The organic phases are combined, washed three times with 200 mL of a saturated sodium bicarbonate solution, then dried over sodium sulfate and concentrated at reduced pressure. The product thus obtained is purified in a silica column, eluting with a mixture of dichloromethane and ethyl acetate, then recrystallized from a mixture of ethanol and methanol. In this way we isolate 5.7 g of the expected product in the form of white crystals.

m.p.=243-244° C.

12.4 N-[6-(Azetidin-1-yl)pyridin-3-yl]-5-trifluoromethyl-1-(3-fluorobenzyl)-1H-pyrrolo[2,3-b]pyridine-2-carboxamide hydrochloride (1:1) (Compound No. 15 in Table 2)

2.6 mL of a 2M solution of hydrochloric acid is added to a solution of 1.2 g of N-[6-(azetidin-1-yl)pyridin-3-yl]-5-trifluoromethyl-1-(3-fluorobenzyl)-1H-pyrrolo[2,3-b]pyridine-2-carboxamide, prepared in the preceding stage, in 50 mL of dichloromethane. The solution is concentrated to dryness and the resultant solid is recrystallized from ethanol. In this way we isolate 0.62 g of the expected salt.

m.p.=230-235° C.

$^1$H NMR (DMSO D$_6$), δ (ppm): 10.98 (s, 1H); 8.87 (s, 1H); 8.79 (s, 1H); 8.47 (s, 1H); 8.2 (dxd, 1H); 7.71 (s, 1H); 7.31 (m, 1H); 7.08 (m, 1H); 6.89 (m, 3H); 5.98 (s, 2H); 4.25 (m, 4H); 2.42 (quint., 2H).

EXAMPLE 13

Compound No. 19 in Table 2

N-[6-(3,3-Difluoroazetidin-1-yl)pyridin-3-yl]-5-trifluoromethyl-1-(3-fluorobenzyl)-1H-pyrrolo[2,3-b]pyridine-2-carboxamide

13.1 2-(3,3'-Difluoroazetidin-1-yl)-5-nitropyridine

A mixture of 0.367 g (2.84 mmol) of 3,3-difluoroazetidine hydrochloride, 0.3 g (1.89 mmol) of 2-chloro-5-nitropyridine and 0.41 mL (2.84 mmol) of triethylamine in 10 mL of dimethylformamide is heated overnight at 100° C. After this time, the suspension is poured into a mixture of 30 mL of water and 30 mL of ethyl acetate. The aqueous phase is separated, and then extracted with 20 mL of ethyl acetate. The organic phases are combined, washed three times with 25 mL of water, then dried over sodium sulfate and concentrated at reduced pressure. The resultant product is purified by chromatography on a silica column, eluting with dichloromethane. We thus obtain 0.34 g of the expected product in the form of a yellow solid.

$^1$H NMR (DMSO D$_6$), δ (ppm): 9 (d, 1H); 8.32 (dxd, 1H); 6.61 (d, 1H); 4.6 (m, 4H).

13.2 3-Amino-6-(3,3-difluoroazetidin-1-yl)pyridine (Amine Vh)

A suspension of 0.34 g (1.58 mmol) of 2-(3,3-difluoroazetidin-1-yl)-5-nitropyridine, prepared in the preceding stage, and 8 mg of Pd/C at 10% in 10 mL of ethanol is stirred vigorously at 20° C. under 5 atm of hydrogen for 4 hours. After this time, the mixture is filtered on a Celite pad, then concentrated at reduced pressure. The resultant product is purified by chromatography on a silica column, eluting with a mixture of dichloromethane and methanol. We thus obtain 0.188 g of the expected product in the form of a red powder, which is used as it is in the rest of the synthesis.

$^1$H NMR (DMSO D$_6$), δ (ppm): 7.6 (s, 1H); 6.96 (dxd, 1H); 6.4 (d, 1H); 4.67 (s, 2H); 4.2 (t, 4H).

13.3 N-[6-(3,3-Difluoroazetidin-1-yl)pyridin-3-yl]-5-trifluoromethyl-1-(3-fluorobenzyl)-1H-pyrrolo[2,3-b]pyridine-2-carboxamide (compound No. 19 in Table 2)

Compound No. 19 was prepared by a method similar to that described in Stage 1.4 by reacting 0.188 g (0.02 mmol) of 3-amino-6-(3,3-difluoroazetidin-1-yl)pyridine, prepared in the preceding stage, with 0.23 g (0.68 mmol) of the acid obtained in Stage 1.3. We thus obtain 140 mg of the expected product in the form of a solid.

m.p.=222-224° C.

¹H NMR (DMSO D₆), δ (ppm): 10.6 (s, 1H); 8.84 (s, 1H); 8.74 (s, 1H); 8.44 (s, 1H); 7.98 (d, 1H); 7.6 (s, 1H); 7.32 (m, 1H); 7.08 (txd, 1H); 6.92 (m, 2H); 6.64 (d, 1H); 6 (s, 2H); 4.39 (m, 4H).

EXAMPLE 14

Compound No. 20 in Table 2

N-[6-(3-Hydroxyazetidin-1-yl)pyridin-3-yl]-5-trifluoromethyl-1-(3-fluorobenzyl)-1H-pyrrolo[2,3-b]pyridine-2-carboxamide

14.1 2-(3-Hydroxyazetidin-1-yl)-5-nitropyridine

A mixture of 0.311 g (2.84 mmol) of 3-hydroxyazetidine hydrochloride, 0.3 g (1.89 mmol) of 2-chloro-5-nitropyridine and 0.41 mL (2.84 mmol) of triethylamine in 10 mL of dimethylformamide is heated overnight at 100° C. After this time, the suspension is poured into a mixture of 30 mL of water and 30 mL of ethyl acetate. The aqueous phase is separated, and then extracted with 20 mL of ethyl acetate. The organic phases are combined, washed three times with 25 mL of water, then dried over sodium sulfate and concentrated at reduced pressure. We thus obtain 0.34 g of the expected product in the form of a solid, which will be used as it is in the rest of the synthesis.

¹H NMR (DMSO D₆), δ (ppm): 8.95 (s, 1H); 8.21 (dxd, 1H); 6.41 (d, 1H); 5.85 (d, 1H); 4.62 (m, 1H); 4.37 (m, 2H); 3.9 (m, 2H).

14.2 3-Amino-6-(3-hydroxyazetidin-1-yl)pyridine (Amine Ve)

A suspension of 0.34 g (1.74 mmol) of 2-(3-hydroxyazetidin-1-yl)-5-nitropyridine, prepared in the preceding stage, and 9 mg of Pd/C at 10% in 10 mL of ethanol is stirred vigorously at 20° C. under 5 atm of hydrogen for 4 hours. After this time, the mixture is filtered on a Celite pad and then concentrated at reduced pressure. The resultant product is purified by chromatography on a silica column, eluting with a mixture of dichloromethane and methanol. We thus obtain 0.1 g of the expected product, which will be used as it is in the rest of the synthesis.

¹H NMR (DMSO D₆), δ (ppm): 7.58 (s, 1H); 6.91 (d, 1H); 6.22 (d, 1H); 5.48 (broadened peak, 1H); 4.48 (broadened peak, 3H); 3.98 (m, 2H); 3.49 (m, 2H).

14.3 N-[6-(3-Hydroxyazetidin-1-yl)pyridin-3-yl]-5-trifluoromethyl-1-(3-fluorobenzyl)-1H-pyrrolo[2,3-b]pyridine-2-carboxamide (compound No. 20 in Table 2)

Compound No. 20 was prepared by a method similar to that described in Stage 1.4 by reacting 99 mg (0.6 mmol) of 3-amino-6-(3-hydroxyazetidin-1-yl)-pyridine, prepared in the preceding stage, with 0.135 g (0.4 mmol) of the acid obtained in Stage 1.3. We thus obtain 103 mg of the expected product in the form of a solid.

m.p.=221-223° C.

¹H NMR (DMSO D₆), δ (ppm): 10.51 (s, 1H); 8.87 (s, 1H); 8.78 (s, 1H); 8.36 (s, 1H); 7.87 (d, 1H); 7.59 (s, 1H); 7.35 (m, 1H); 7.09 (m, 1H); 6.95 (m, 2H); 6.45 (d, 1H); 6 (s, 2H); 5.61 (s, 1H); 4.59 (m, 1H); 4.15 (m, 2H); 3.68 (m, 2H).

EXAMPLE 15

Compound No. 22 in Table 2

N-[4-Methyl-6-(pyrrolidin-1-yl)pyridin-3-yl]-6-trifluoromethyl-1-(3-fluorobenzyl)-1H-pyrrolo[2,3-b]pyridine-2-carboxamide

15.1 6-Trifluoromethyl-1-[(3-fluorophenyl)methyl]-1H-pyrrolo[2,3-b]pyridine-2-methyl carboxylate According to a method similar to that described in Stage 1.2, by reacting 1.5 g (6.14 mmol) of 6-trifluoromethyl-1H-pyrrolo[2,3-b]pyridine-2-methyl carboxylate and 1 mL (9.21 mmol) of 3-fluorobenzyl alcohol, we obtain 2.1 g of the expected compound.

¹H NMR (CDCl₃), δ (ppm): 8.3 (d, 1H); 7.69 (d, 1H); 7.48 (s, 1H); 7.4-7.19 (m, 2H); 7.08 (m, 2H); 6.11 (s, 2H); 4.05 (s, 3H).

15.2 6-Trifluoromethyl-1-[(3-fluorophenyl)methyl]-1H-pyrrolo[2,3-b]pyridine-2-carboxylic acid According to a method similar to that described in Stage 1.3, starting from 2.1 g (5.96 mmol) of 6-trifluoromethyl-1-[(3-fluorophenyl)methyl]-1H-pyrrolo[2,3-b]pyridine-2-methyl carboxylate, prepared in the preceding stage, we obtain 2 g of the expected compound.

¹H NMR (DMSO D₆), δ (ppm): 8.39 (d, 1H); 7.64 (d, 1H); 7.32 (m, 1H); 7.24 (s, 1H); 7.05 (m, 3H); 6.02 (s, 2H).

15.3 N-[4-Methyl-6-(pyrrolidin-1-yl)pyridin-3-yl]-6-trifluoromethyl-1-(3-fluorobenzyl)-1H-pyrrolo[2,3-b]pyridine-2-carboxamide (compound No. 22 in Table 2)

Compound No. 22 was prepared by a method similar to that described in Stage 1.4 by reacting 0.314 g (1.77 mmol) of 3-amino-4-methyl-6-(pyrrolidin-1-yl)pyridine (WO05/035526) with 0.5 g (0.1.48 mmol) of the acid obtained in the preceding stage. We thus obtain 0.24 g of the expected product in the form of a solid.

m.p.=202-203° C.

¹H NMR (DMSO D₆), δ (ppm): 10.09 (s, 1H); 8.5 (d, 1H); 7.87 (s, 1H); 7.72 (d, 1H); 7.5 (s, 1H); 7.32 (m, 1H); 7.08 (m, 1H); 6.95 (m, 2H); 6.38 (s, 1H); 5.94 (s, 2H); 3.39 (m, 4H); 2.06 (s, 3H); 1.95 (m, 4H).

EXAMPLE 16

Compound No. 33 in Table 2

N-[6-(Pyrrolidin-1-yl)pyridin-3-yl]-6-trifluoromethyl-1-(3-fluorobenzyl)-1H-pyrrolo[2,3-b]pyridine-2-carboxamide

16.1 N-[6-Chloropyridin-3-yl]-6-trifluoromethyl-1-(3-fluorobenzyl)-1H-pyrrolo[2,3-b]pyridine-2-carboxamide According to a method similar to that described in Stage 6.1, by reacting 0.5 g (1.48 mmol) of 6-trifluoromethyl-1-[(3-fluorophenyl)methyl]-1H-pyrrolo[2,3-b]pyridine-2-carboxylic acid, described in Stage 15.2 with 0.288 (2.22 mmol)

of 3-amino-6-chloropyridine, we obtain 0.33 g of the expected compound in the form of a white solid.

m.p.=202-203° C.

$^1$H NMR (DMSO D$_6$), δ (ppm): 10.95 (s, 1H); 8.75 (d, 1H); 8.58 (d, 1H); 8.22 (d, 1H); 7.76 (d, 1H); 7.61 (s, 1H); 7.53 (d, 1H); 7.32 (m, 1H); 7.05 (m, 1H); 6.98 (m, 2H); 5.94 (s, 2H).

16.2 N-[6-(Pyrrolidin-1-yl)pyridin-3-yl]-6-trifluoromethyl-1-(3-fluorobenzyl)-1H-pyrrolo[2,3-b]pyridine-2-carboxamide (Product No. 33 in Table 2)

According to a method similar to that described in Stage 6.2, by reacting 0.3 g (0.67 mmol) of N-[6-chloropyridin-3-yl]-6-trifluoromethyl-1-(3-fluorobenzyl)-1H-pyrrolo[2,3-b]pyridine-2-carboxamide, described in the preceding stage, with 0.56 mL (6.68 mmol) of pyrrolidine, we obtain 0.21 g of the expected compound.

m.p.=204-205° C.

$^1$H NMR (DMSO D$_6$), δ (ppm): 10.5 (s, 1H); 8.58 (d, 1H); 8.39 (d, 1H); 7.87 (dxd, 1H); 7.79 (d, 1H); 7.59 (s, 1H); 7.4 (m, 1H); 7.12 (m, 1H); 7.07 (m, 2H); 6.53 (d, 1H); 6.01 (s, 2H); 3.46 (m, 4H); 2 (m, 4H).

EXAMPLE 17

Compound No. 34 in Table 2

N-[6-(Pyrrolidin-1-yl)-4-trifluoromethylpyridin-3-yl]-5-trifluoromethyl-1-(3-fluorobenzyl)-1H-pyrrolo[2,3-b]pyridine-2-carboxamide

17.1 6-(Pyrrolidin-1-yl)-4-(trifluoromethyl)pyridine-3-methyl carboxylate

A mixture of 2.5 g (10.43 mmol) of 6-chloro-4-trifluoromethyl-methyl nicotinate, 2.88 g (20.87 mmol) of potassium carbonate and 2.61 mL (31.3 mmol) of pyrrolidine in 90 mL of dimethylformamide is heated at 100° C. for 3 hours. The reaction mixture is then concentrated at reduced pressure and is then taken up in 100 mL of water. The precipitate is collected by filtration and is washed with 150 mL of water. After drying at reduced pressure, 2.5 g of the expected compound is isolated.

$^1$H NMR (CDCl$_3$), δ (ppm): 2.11 (m, 4H); 3.61 (broadened peak, 4H); 3.93 (s, 3H); 6.69 (s, 1H); 8.89 (s, 1H).

17.2 6-(Pyrrolidin-1-yl)-4-(trifluoromethyl)pyridine-3-carboxylic acid

A mixture of 2.5 g (9.12 mmol) of 6-(pyrrolidin-1-yl)-4-(trifluoromethyl)pyridine-3-methyl carboxylate, obtained in the preceding stage, and 0.76 g (13.67 mmol) of potassium hydroxide in 50 mL of methanol and 2 mL of water is heated at 20° C. for 24 hours. The mixture is then concentrated at reduced pressure. Then 100 mL of water is added and the solution is washed with 100 mL of dichloromethane, then acidified to pH 4 with additions of concentrated hydrochloric acid. A precipitate is collected by filtration and is then washed with 50 mL of water. After drying at reduced pressure, 2.2 g of the expected compound is isolated.

$^1$H NMR (DMSO D$_6$), δ (ppm): 1.99 (s, 4H); 3.51 (broadened peak, 4H); 6.71 (s, 1H); 8.72 (s, 1H).

17.3 6-(Pyrrolidin-1-yl)-4-trifluoromethyl-3-(terbutoxycarbonylamino)pyridine A mixture of 2.2 g (8.45 mmol) of 6-(pyrrolidin-1-yl)-4-(trifluoromethyl)pyridine-3-carboxylic acid, obtained in the preceding stage, 2.37 mL (10.99 mmol) of diphenylphosphorylazide and 2.95 mL (21.14 mmol) of triethylamine in 25 mL of tert-butanol is heated at 90° C. for 5 hours. The reaction mixture is then concentrated at reduced pressure, taken up in 50 mL of water, then extracted 3 times with 50 mL of dichloromethane. The organic phases are combined, washed with 50 ml of water, dried over sodium sulfate and then concentrated at reduced pressure. The oil obtained is purified by chromatography on a silica column, eluting with a mixture of dichloromethane and methanol. In this way we isolate 1.05 g of the expected product.

$^1$H NMR (CDCl$_3$), δ (ppm): 1.53 (s, 9H); 2.09 (m, 4H); 3.51 (m, 4H); 6.2 (broadened peak, 1H); 6.52 (s, 1H); 8.39 (broadened peak, 1H).

17.4 6-(Pyrrolidin-1-yl)-4-trifluoromethyl-3-aminopyridine hydrochloride (Amine Vg)

A solution of 1 g (3.02 mmol) of 6-(pyrrolidin-1-yl)-4-trifluoromethyl-3-(terbutoxycarbonylamino)pyridine, prepared in the preceding stage, in 11 mL of 4N hydrochloric acid in dioxane, is stirred for 5 hours under reflux. Then 200 mL of ethyl ether is added to the cooled reaction mixture. 0.8 g of a precipitate is collected by filtration.

Melting point: 207-209° C.;

$^1$H NMR (DMSO D$_6$), δ (ppm): 2 (m, 4H); 3.52 (m, 4H); 7.1 (s, 1H); 7.49 (broadened peak, 2H); 7.92 (s, 1H).

17.5 N-[6-(Pyrrolidin-1-yl)-4-trifluoromethylpyridin-3-yl]-5-trifluoromethyl-1-(3-fluorobenzyl)-1H-pyrrolo[2,3-b]pyridine-2-carboxamide (compound No. 34 in the table).

Compound No. 34 was prepared by a method similar to that described in Stage 1.4 by reacting 0.411 g (1.54 mmol) of 6-(pyrrolidin-1-yl)-4-trifluoromethyl-3-aminopyridine hydrochloride, obtained in the preceding stage, with 0.4 g (0.18 mmol) of 5-trifluoromethyl-1-[(3-fluorophenyl)methyl]-1H-pyrrolo[2,3-b]pyridine-2-carboxylic acid obtained in Stage 1.3, the whole in the presence of 0.25 mL (1.77 mmol) of triethylamine, 0.175 g (1.3 mmol) of 1-hydroxybenzotriazole monohydrate and 0.25 g (1.3 mmol) of N-(3-dimethylaminopropyl)-N'-ethylcarbodiimide hydrochloride. We thus obtain 0.15 g of the expected product in the form of a solid.

m.p.=207-208° C.

$^1$H NMR (DMSO D$_6$), δ (ppm): 10.29 (s, 1H); 8.81 (s, 1H); 8.72 (s, 1H); 8.09 (s, 1H); 7.57 (s, 1H); 7.32 (m, 1H); 7.09 (m, 1H); 6.99 (d, 1H); 6.91 (d, 1H); 6.7 (s, 1H); 5.95 (s, 2H); 3.5 (m, 4H); 1.99 (m, 4H).

EXAMPLE 18

Compound No. 35 in Table 2

N-[5-Fluoro-6-(N,N-dimethylamino)pyridin-3-yl]-5-trifluoromethyl-1-(3-fluorobenzyl)-1H-pyrrolo[2,3-b]pyridine-2-carboxamide Compound No. 35 was prepared by a method similar to that described in Stage 1.4 by reacting 0.4 g (1.18 mmol) of 5-fluoro-6-(N,N-dimethylamino)-3-aminopyridine (WO2004/110986), with 0.4 g (0.18 mmol) of 5-trifluoromethyl-1-[(3-fluorophenyl)methyl]-1H-pyrrolo[2,3-b]pyridine-2-carboxylic acid obtained in Stage 1.3. We thus obtain 0.33 g of the expected product in the form of a solid.

m.p.=199-200° C.

¹H NMR (DMSO D₆), δ (ppm): 10.7 (s, 1H); 8.85 (s, 1H); 8.77 (s, 1H); 8.29 (s, 1H); 7.89 (d, 1H); 7.6 (s, 1H); 7.32 (m, 1H); 7.09 (m, 1H); 6.98 (m, 2H); 6 (s, 2H); 3.02 (s, 6H).

EXAMPLE 19

Compound No. 36 in Table 2

N-[2-(N,N-Dimethylamino)pyrimidin-5-yl]-5-trifluoromethyl-1-(3-fluorobenzyl)-1H-pyrrolo[2,3-b]pyridine-2-carboxamide 19.1 N-(2-Chloropyrimidin-5-yl)-5-trifluoromethyl-1-(3-fluorobenzyl)-1H-pyrrolo[2,3-b]pyridine-2-carboxamide According to a method similar to that described in Stage 1.4, starting from 1.08 g (3.2 mmol) of 5-trifluoromethyl-1-[(3-fluorophenyl)methyl]-1H-pyrrolo[2,3-b]pyridine-2-carboxylic acid, described in Stage 1.3, and 0.46 g (3.52 mmol) of 2-chloro-5-aminopyrimidine, we obtain 0.33 g of the expected product.

19.2 N-[2-(N,N-Dimethylamino)pyrimidin-5-yl]-5-trifluoromethyl-1-(3-fluorobenzyl)-1H-pyrrolo[2,3-b]pyridine-2-carboxamide (compound No. 36 in Table 2)

In a sealed tube, a mixture of 0.2 g (0.44 mmol) of N-(2-chloropyrimidin-5-yl)-5-trifluoromethyl-1-(3-fluorobenzyl)-1H-pyrrolo[2,3-b]pyridine-2-carboxamide, prepared in the preceding stage, and 1.3 mL (8.89 mmol) of an aqueous solution of dimethylamine at 40%, the whole in solution in 15 mL of ethanol, is heated at 110° C. for 20 h. After this time, the reaction mixture is allowed to return to room temperature, then a white precipitate is collected by filtration, washed with water and dried at reduced pressure to obtain 0.14 g of the expected product.
m.p.=236-238° C.
¹H NMR (DMSO D₆), δ (ppm): 10.51 (s, 1H); 8.82 (s, 1H); 8.75 (s, 1H); 8.6 (s, 2H); 7.56 (s, 1H); 7.32 (m, 1H); 7.08 (m, 1H); 6.96 (m, 2H); 5.98 (s, 2H); 3.11 (s, 6H).

EXAMPLE 20

Compound No. 37 in Table 2

N-[6-(3-Azabicyclo[3.2.0]hept-3-yl)pyridin-3-yl]-5-trifluoromethyl-1-(3-fluorobenzyl)-1H-pyrrolo[2,3-b]pyridine-2-carboxamide 20.1 2-(3-Azabicyclo[3.2.0]hept-3-yl)-5-nitropyridine A mixture of 0.1 g (0.63 mmol) of 2-chloro-5-nitropyridine, 0.1 g (0.75 mmol) of 3-aza-bicyclo[3.2.0]heptane (J. Med. Chem. 1967, 10(4), 621) and 0.26 mL (0.19 mmol) of triethylamine in 10 mL of dioxane, is heated at 65° C. for 4 h. The reaction mixture is then poured into 50 mL of ice water. The mixture is stirred until the ice has melted completely, then a yellow precipitate is collected by filtration and is dried at reduced pressure. In this way we isolate 0.121 g of the expected product in the form of a yellow powder.
¹H NMR (DMSO D₆), δ (ppm): 9 (d, 1H); 8.23 (dxd, 1H); 6.7 (d, 1H); 3.81 (broadened peak, 2H); 3.51 (m, 2H); 3.09 (m, 2H); 2.27 (m, 2H); 1.71 (m, 2H).

20.2 6-(3-Azabicyclo[3.2.0]hept-3-yl)-3-aminopyridine (Amine Va)

According to a procedure similar to that described in Stage 14.2, starting from 0.12 g (0.55 mmol) of 2-(3-azabicyclo[3.2.0]hept-3-yl)-5-nitropyridine, prepared in the preceding stage, and 0.17 g of palladium on charcoal at 10%, we obtain 0.096 g of the expected compound.
¹H NMR (DMSO D₆), δ (ppm): 7.62 (d, 1H); 6.95 (d, 1H); 6.49 (d, 1H); 4.42 (broadened peak, 2H); 3.52 (d, 2H); 2.98 (m, 4H); 2.21 (m, 2H); 1.72 (m, 2H).

20.3 N-[6-(3-Azabicyclo[3.2.0]hept-3-yl)pyridin-3-yl]-5-trifluoromethyl-1-(3-fluorobenzyl)-1H-pyrrolo[2,3-b]pyridine-2-carboxamide (compound No. 37 in Table 2)

According to a method similar to that described in Stage 12.3, starting from 0.12 g (0.35 mmol) of 5-trifluoromethyl-1-[(3-fluorophenyl)methyl]-1H-pyrrolo[2,3-b]pyridine-2-carboxylic acid, described in Stage 1.3, and 0.075 g (0.38 mmol) of 6-(3-azabicyclo[3.2.0]hept-3-yl)-3-aminopyridine, prepared in the preceding stage, we obtain 0.12 g of the expected product.
m.p.=172-174° C.
¹H NMR (DMSO D₆), δ (ppm): 10.45 (s, 1H); 8.81 (s, 1H); 8.71 (s, 1H); 8.36 (s, 1H); 7.81 (d, 1H); 7.52 (s, 1H); 7.31 (m, 1H); 7.08 (m, 1H); 6.92 (m, 2H); 6.62 (d, 1H); 5.98 (s, 2H); 3.67 (d, 2H); 3.2 (m, 2H); 3.02 (m, 2H); 2.23 (m, 2H); 1.72 (m, 2H).

EXAMPLE 21

Compound No. 38 in Table 2

N-[6-(3-Azabicyclo[3.1.0]hex-3-yl)pyridin-3-yl]-5-trifluoromethyl-1-(3-fluorobenzyl)-1H-pyrrolo[2,3-b]pyridine-2-carboxamide 21.1 2-(3-Azabicyclo[3.1.0]hex-3-yl)-5-nitropyridine A mixture of 0.5 g (3.15 mmol) of 2-chloro-5-nitropyridine, 0.452 g (3.78 mmol) of 3-aza-bicyclo[3.2.0]heptane (J. Med. Chem. 1967, 10(4), 621) and 1.32 mL (6.94 mmol) of triethylamine in 10 mL of dioxane, is heated at 65° C. for 4 h. The reaction mixture is then poured into 50 mL of ice water. The mixture is stirred until the ice has melted completely, then a yellow precipitate is collected by filtration and is dried at reduced pressure. In this way we isolate 0.63 g of the expected product in the form of a yellow powder.
¹H NMR (DMSO D₆), δ (ppm): 8.91 (d, 1H); 8.15 (dxd, 1H); 6.53 (d, 1H); 3.95-3.45 (m, 4H); 1.75 (m, 2H); 0.77 (m, 1H); 0.65 (m, 1H).

21.2 6-(3-Azabicyclo[3.1.0]hex-3-yl)-3-aminopyridine (amine Vf)

According to a procedure similar to that described in Stage 14.2, starting from 0.6 g (2.92 mmol) of 2-(3-azabicyclo[3.2.0]hex-3-yl)-5-nitropyridine, prepared in the preceding stage, and 0.9 g of palladium on charcoal at 10%, we obtain 0.49 g of the expected compound.
¹H NMR (DMSO D₆), δ (ppm): 7.55 (s, 1H); 6.99 (d, 1H); 6.25 (d, 1H); 4.32 (broadened peak, 2H); 3.51 (d, 2H); 3.11 (m, 2H); 1.6 (m, 2H); 0.66 (m, 1H); 0.2 (m, 1H).

21.3 N-[6-(3-Azabicyclo[3.1.0]hex-3-yl)pyridin-3-yl]-5-trifluoromethyl-1-(3-fluorobenzyl)-1H-pyrrolo[2,3-b]pyridine-2-carboxamide (compound No. 38 in Table 2)

According to a method similar to that described in Stage 12.3, starting from 0.5 g (1.48 mmol) of 5-trifluoromethyl-1-[(3-fluorophenyl)methyl]-1H-pyrrolo[2,3-b]pyridine-2-carboxylic acid, described in Stage 1.3, and 0.3 g (1.71 mmol) of 6-(3-azabicyclo[3.1.0]hex-3-yl)-3-aminopyridine, prepared in the preceding stage, we obtain 0.233 g of the expected product.

m.p.=212-214° C.

$^1$H NMR (DMSO D$_6$), δ (ppm): 10.42 (s, 1H); 8.81 (s, 1H); 8.72 (s, 1H); 8.31 (s, 1H); 7.79 (d, 1H); 7.52 (s, 1H); 7.31 (m, 1H); 7.08 (m, 1H); 6.93 (m, 2H); 6.48 (d, 1H); 5.97 (s, 2H); 3.63 (d, 2H); 3.31 (m, 2H); 1.69 (m, 2H); 0.74 (m, 1H); 0.2 (m, 1H).

EXAMPLE 22

Compound No. 39 in Table 2

N-[6-(3-Azabicyclo[3.1.0]hex-3-yl)-pyridin-3-yl]-5-fluoro-1-(3-fluorobenzyl)-1H-pyrrolo[2,3-b]pyridine-2-carboxamide

22.1 5-Fluoro-1-(3-fluorobenzyl)-1H-pyrrolo[2,3-b]pyridine-2-carboxylic acid A mixture of 6.9 g (20.58 mmol) of 5-fluoro-1-(3-fluorobenzyl)-1H-pyrrolo[2,3-b]pyridine-2-ethyl carboxylate (WO07/010,138) and 1.89 g (33.7 mmol) of potassium hydroxide in a mixture of 80 mL of ethanol and 10 mL of water is heated under reflux for 1.5 h. After this time, the reaction mixture is concentrated at reduced pressure, and is then taken up in 200 mL of water. The solution is acidified with additions of concentrated hydrochloric acid, and then extracted three times with 50 mL of dichloromethane. The organic phases are combined, dried over sodium sulfate and then concentrated at reduced pressure. The resultant product is triturated in 5 mL of dichloromethane. A precipitate is collected by filtration and is dried at reduced pressure. In this way we isolate 5.35 g of the expected product, which is used as it is in the rest of the synthesis.

22.2 N-[6-(3-Azabicyclo[3.1.0]hex-3-yl)-pyridin-3-yl]-5-fluoro-1-(3-fluorobenzyl)-1H-pyrrolo[2,3-b]pyridine-2-carboxamide (compound No. 39 in Table 2)

According to a method similar to that described in Stage 12.3, starting from 0.45 g (1.56 mmol) of 5-fluoro-1-[(3-fluorophenyl)methyl]-1H-pyrrolo[2,3-b]pyridine-2-carboxylic acid, described in the preceding stage, and 0.3 g (1.71 mmol) of 6-(3-azabicyclo[3.1.0]hex-3-yl)-3-aminopyridine, prepared in Stage 21.2, we obtain 0.47 g of the expected product.

m.p.=222-224° C.

$^1$H NMR (DMSO D$_6$), δ (ppm): 10.32 (s, 1H); 8.47 (s, 1H); 8.31 (s, 1H); 8.13 (d, 1H); 7.78 (d, 1H); 7.39 (s, 1H); 7.19 (m, 1H); 7.02 (m, 1H); 6.92 (m, 2H); 6.47 (d, 1H); 5.9 (s, 2H); 3.62 (d, 2H); 3.31 (m, 2H); 1.69 (m, 2H); 0.75 (m, 1H); 0.2 (m, 1H).

EXAMPLE 23

Compound No. 171 in Table 2

3-[[5-[[[1-(3-Fluorobenzyl)-5-trifluoromethyl-1H-pyrrolo[2,3-b]pyridin-2-yl]carbonyl]amino]pyridin-2-yl]amino]ethyl propionate

23.1 3-[(5-Aminopyridin-2-yl)amino]ethyl propionate

A suspension of 2.3 g (9.61 mmol) of 3-[(5-nitropyridin-2-yl)amino]ethyl propionate (JP07/051,121) and 0.5 g of Raney Nickel in 96 mL of acetic acid is stirred for 7 hours, at 20° C. under 5 atm of hydrogen. After this time, the reaction mixture is filtered on a Celite pad and then concentrated at reduced pressure. The product obtained is used as it is in the rest of the synthesis.

23.4 3-[[5-[[[1-(3-Fluorobenzyl)-5-trifluoromethyl-1H-pyrrolo[2,3-b]pyridin-2-yl]carbonyl]amino]pyridin-2-yl]amino]ethyl propionate According to a method similar to that described in Example 1.4, starting from 0.558 g (2.67 mmol) of 3-[(5-aminopyridin-2-yl)amino]ethyl propionate, obtained in the preceding stage, and 0.3 g (0.89 mmol) of 5-trifluoromethyl-1-[(3-fluorophenyl)methyl]-1H-pyrrolo[2,3-b]pyridine-2-carboxylic acid, obtained according to Stage 1.3, we obtain 0.26 g of the expected product.

LCMS: [MH]$^+$=530

$^1$H NMR (DMSO D$_6$), δ (ppm): 10.4 (s, 1H); 8.81 (s, 1H); 8.71 (s, 1H); 8.25 (s, 1H); 7.68 (d, 1H); 7.53 (s, 1H); 7.31 (m, 1H); 7.05 (m, 1H); 6.92 (m, 2H); 6.59 (m, 1H); 6.51 (d, 1H); 5.96 (s, 2H); 4.1 (q, 2H); 3.5 (m, 2H); 2.56 (m, 2H); 1.2 (t, 3H).

EXAMPLE 24

Compound No. 40 in Table 2

3-[[5-[[[1-(3-Fluorobenzyl)-5-trifluoromethyl-1H-pyrrolo[2,3-b]pyridin-2-yl]carbonyl]amino]pyridin-2-yl]amino]propionic acid A solution, in 10 mL of ethanol, of 0.26 g (0.49 mmol) of compound No. 171 prepared in Example 23 and 1 mL (1 mmol) of a molar solution of sodium hydroxide, is stirred at 20° C. for 20 h. After this time, the mixture is concentrated at reduced pressure, and is then taken up in 100 mL of water and 100 mL of ethyl acetate. The pH of the aqueous phase is acidified by successive additions of 1N hydrochloric acid solution. The organic phase is then separated, washed once with 100 mL of water, once with 50 mL of saturated sodium chloride solution, then dried over magnesium sulfate and concentrated at reduced pressure. In this way we isolate 0.21 g of the expected product.

m.p.=196-199° C.

$^1$H NMR (DMSO D$_6$), δ (ppm): 12.1 (broadened peak, 1H); 10.39 (s, 1H); 8.8 (s, 1H); 8.71 (s, 1H); 8.25 (s, 1H); 7.69 (d, 1H); 7.52 (s, 1H); 7.31 (m, 1H); 7.07 (m, 1H); 6.92 (m, 2H); 6.5 (m, 2H); 5.96 (s, 2H); 3.46 (m, 2H); 2.49 (m, 2H partially covered by the DMSO peak).

EXAMPLE 25

Compound No. 41 in Table 2

N-[6-(3-Hydroxypropylamino)pyridin-3-yl]-5-trifluoromethyl-1-(3-fluorobenzyl)-1H-pyrrolo[2,3-b]pyridine-2-carboxamide A mixture, in 7.5 mL of tetrahydrofuran, of 0.2 g (0.38 mmol) of compound No. 171, prepared in Stage 23, 0.14 g (3.78 mmol) of sodium borohydride and 0.15 mL (3.78 mmol) of methanol, is stirred for 48 h under reflux. After this time, the reaction mixture is poured into 200 mL of ice water. 1 mL of acetic acid is added, then the mixture is extracted twice with 100 mL of ethyl acetate. The organic phases are combined, then washed twice with 100 mL of water, once with 50 mL of saturated sodium chloride solution, then dried over magnesium sulfate and concentrated at reduced pressure. The residue obtained is purified by chromatography on a silica column, eluting with a mixture of dichloromethane and methanol. We thus obtain 67 mg of the expected compound.
m.p.=207-210° C.
$^1$H NMR (DMSO $D_6$), δ (ppm): 10.22 (s, 1H); 8.68 (s, 1H); 8.59 (s, 1H); 8.09 (s, 1H); 7.52 (d, 1H); 7.4 (s, 1H); 7.17 (m, 1H); 6.91 (m, 1H); 6.8 (m, 2H); 6.35 (d, 1H); 6.3 (m, 1H); 5.83 (s, 2H); 4.33 (t, 1H); 3.37 (m, 2H); 2.49 (m, 2H partially covered by the DMSO peak); 1.55 (m, 2H).

EXAMPLE 26

Compound No. 29 in Table 2

N-[4-Methoxy-6-(pyrrolidin-1-yl)-pyridin-3-yl]-5-trifluoromethyl-1-[(4-pyridinyl)methyl]-1H-pyrrolo[2,3-b]pyridine-2-carboxamide 26.1 4-Methoxy-5-nitro-2-(pyrrolidin-1-yl)pyridine The method described in Stage 12.1 is followed, starting from 5.4 g (28.64 mmol) of 2-chloro-4-methoxy-5-nitropyridine (WO2003/080610) and 4.53 g (63 mmol) of pyrrolidine. The product obtained is, in this case, purified by chromatography on a silica column, eluting with a mixture of heptane and ethyl acetate. In this way we isolate 3 g of the expected product.
$^1$H NMR (DMSO $D_6$), δ (ppm): 8.98 (s, 1H); 5.79 (s, 1H); 4.07 (s, 3H); 3.65 (m, 4H); 2.17 (m, 4H).

26.2 5-Amino-4-methoxy-2-(pyrrolidin-1-yl)pyridine (Amine Vd)

The method described in Stage 12.2 is followed, starting from 1.5 g (6.72 mmol) of 4-methoxy-5-nitro-2-(pyrrolidin-1-yl)-pyridine, obtained in Stage 6.1, and 0.15 g of palladium on charcoal at 10%. We thus obtain 1.25 g of the expected product.
$^1$H NMR (DMSO $D_6$), δ (ppm): 7.16 (s, 1H); 6.61 (s, 1H); 4.52 (broadened peak, 2H); 3.71 (s, 3H); 3.29 (m, 4H); 1.81 (m, 4H).

26.3 N-[4-Methoxy-6-(pyrrolidin-1-yl)pyridin-3-yl]-5-trifluoromethyl-1-[(4-pyridyl)methyl]-1H-pyrrolo[2,3-b]pyridine-2-carboxamide (Compound No. 29 in Table 2)

The method described in Example 12.3 is followed, starting from 5-amino-4-methoxy-2-(pyrrolidin-1-yl)pyridine, prepared in the preceding stage, and 5-trifluoromethyl-1-[(4-pyridyl)methyl]-1H-pyrrolo[2,3-b]pyridine-2-carboxylic acid prepared in Stage 9.2.
m.p.=222-224° C.
$^1$H NMR (DMSO $D_6$), δ (ppm): 9.86 (s, 1H); 8.79 (s, 1H); 8.71 (s, 1H); 8.45 (d, 2H); 7.85 (s, 1H); 7.59 (s, 1H); 7.02 (d, 2H); 6.01 (s, 1H); 5.95 (s, 1H); 4.38 (s, 3H); 3.39 (m, 4H); 1.93 (m, 4H)

EXAMPLE 27

Compound No. 124 in Table 2

N-[6-(3-Hydroxyazetidin-1-yl)-pyridin-3-yl]-1-(3-methoxybenzyl)-1H-pyrrolo[2,3-b]pyridine-2-carboxamide trifluoroacetate (1:1)

27.1 1-(3-Methoxybenzyl)-1H-pyrrolo[2,3-b]pyridine-2-ethyl carboxylate 0.089 mL (0.45 mmol) of diisopropyl azodicarboxylate is added dropwise under argon at 20° C., to a mixture of 260 mg (0.6 mmol) of supported triphenylphosphine (Argonaut PS-PPh$_3$, loading 2.3 mmol/g), 57 mg (0.3 mmol) of 1H-pyrrolo[2,3-b]pyridine-2-ethyl carboxylate (WO07/010,138) and 62 mg (0.45 mmol) of 3-methoxybenzyl alcohol in 2.5 mL of tetrahydrofuran. The reactor is then sealed and the mixture is stirred for 3 days at 20° C. After this time, the reaction mixture is filtered, the solid residue is washed with 5 mL of tetrahydrofuran and the filtrate is concentrated at reduced pressure to give the expected product, which is used as it is in the rest of the synthesis.

27.2 1-(3-Methoxybenzyl)-1H-pyrrolo[2,3-b]pyridine-2-carboxylic acid

A mixture of 1-(3-methoxybenzyl)-1H-pyrrolo[2,3-b]pyridine-2-ethyl carboxylate obtained in the preceding stage and 0.195 mL (0.39 mmol) of 2N sodium hydroxide in 5 mL of ethanol and 1 mL of water is heated in a sealed tube at 70° C. for 2 h. After this time, the reaction mixture is concentrated at reduced pressure, and is then taken up in 2 mL of dimethylformamide and 0.03 mL of trifluoroacetic acid. The solution is filtered, and is then chromatographed on a reverse-phase HPLC column. In this way we isolate 33.4 mg of the expected product.

27.3 N-[6-(3-Hydroxyazetidin-1-yl)pyridin-3-yl]-1-(3-methoxybenzyl)-1H-pyrrolo[2,3-b]pyridine-2-carboxamide trifluoroacetate (1:1) (compound No. 124 in Table 2)

According to a method similar to that described in Stage 12.3, starting from 0.0167 g (0.59 mmol) of 1-(3-methoxybenzyl)-1H-pyrrolo[2,3-b]pyridine-2-carboxylic acid, described in the preceding stage, and 0.0149 g (0.09 mmol) of 3-amino-6-(3-hydroxyazetidin-1-yl)pyridine, prepared in Stage 14.2, we obtain 0.013 g of the expected product.
LCMS: [MH]$^+$=430
$^1$H NMR (DMSO $D_6$), δ (ppm): 10.59 (s, 1H); 8.45 (d, 1H); 8.4 (s, 1H); 8.21 (d, 1H); 8.01 (d, 1H); 7.39 (s, 1H); 7.26 (m, 1H); 7.12 (dxd, 1H); 6.75 (m, 2H); 6.52 (m, 2H); 5.89 (s, 2H); 4.62 (m, 1H); 4.32 (m, 2H); 3.86 (m, 2H); 3.62 (s, 3H).

According to a method similar to that described in Example 27, 128 other compounds were prepared and characterized by their mass peak in LC-MS in Tables 2, 3 and 4. As examples, the $^1$H NMR spectra of some of these products are described below:

N-[6-(Azetidin-1-yl)-pyridin-3-yl]-1-(2-fluorobenzyl)-5-trifluoromethyl-1H-pyrrolo[2,3-b]pyridine-2-carboxamide trifluoroacetate (1:1) (compound No. 43 in Table 2)

LCMS: [MH]$^+$=470
$^1$H NMR (DMSO D$_6$), δ (ppm): 10.7 (s, 1H); 8.79 (d, 2H); 8.34 (s, 1H); 7.99 (d, 1H); 7.59 (s, 1H); 7.28 (m, 1H); 7.19 (m, 1H); 7.02 (t, 1H); 6.7 (m, 2H); 6 (s, 2H); 4.12 (m, 4H); 2.4 (m, 2H).

N-[6-(Azetidin-1-yl)pyridin-3-yl]-1-(4-fluorobenzyl)-5-trifluoromethyl-1H-pyrrolo[2,3-b]pyridine-2-carboxamide trifluoroacetate (1:1) (compound No. 44 in Table 2)

LCMS: [MH]$^+$=470
$^1$H NMR (DMSO D$_6$), δ (ppm): 10.7 (s, 1H); 8.82 (s, 1H); 8.76 (s, 1H); 8.49 (s, 1H); 8.02 (s, 1H); 7.58 (s, 1H); 7.19 (m, 2H); 7.09 (m, 2H); 6.75 (d, 1H); 5.93 (s, 2H); 4.12 (m, 4H); 2.41 (m, 2H).

N-[6-(Azetidin-1-yl)pyridin-3-yl]-1-(3-trifluoromethylbenzyl)-5-trifluoromethyl-1H-pyrrolo[2,3-b]pyridine-2-carboxamide trifluoroacetate (1:1) (compound No. 45 in Table 2)

LCMS: [MH]$^+$=520
$^1$H NMR (DMSO D$_6$), δ (ppm): 10.7 (s, 1H); 8.85 (s, 1H); 8.78 (s, 1H); 8.38 (s, 1H); 8 (broadened peak, 1H); 7.6 (m, 3H); 7.51 (m, 1H); 7.37 (m, 1H); 6.72 (broadened peak, 1H); 6.03 (s, 2H); 4.11 (m, 4H); 2.39 (m, 2H).

N-[6-(Azetidin-1-yl)pyridin-3-yl]-1-(4-methylbenzyl)-5-trifluoromethyl-1H-pyrrolo[2,3-b]pyridine-2-carboxamide trifluoroacetate (1:1) (compound No. 46 in Table 2)

LCMS: [MH]$^+$=466
$^1$H NMR (DMSO D$_6$), δ (ppm): 10.61 (s, 1H); 8.82 (s, 1H); 8.73 (s, 1H); 8.39 (s, 1H); 8 (broadened peak, 1H); 7.52 (s, 1H); 7.04 (m, 4H); 6.71 (broadened peak, 1H); 5.91 (s, 2H); 4.11 (m, 4H); 2.4 (m, 2H); 2.21 (s, 3H).

N-[6-(Azetidin-1-yl)pyridin-3-yl]-1-(3-methoxybenzyl)-5-trifluoromethyl-1H-pyrrolo[2,3-b]pyridine-2-carboxamide trifluoroacetate (1:1) (compound No. 48 in Table 2)

LCMS: [MH]$^+$=482
$^1$H NMR (DMSO D$_6$), δ (ppm): 10.7 (s, 1H); 8.81 (s, 1H); 8.75 (s, 1H); 8.39 (s, 1H); 8 (broadened peak, 1H); 7.55 (s, 1H); 7.17 (t, 1H); 6.79 (dxd, 1H); 6.75 (broadened peak, 1H); 6.67 (s, 1H); 6.63 (d, 1H); 5.94 (s, 2H); 4.11 (m, 4H); 3.65 (s, 3H); 2.41 (m, 2H).

N-[6-(Azetidin-1-yl)-pyridin-3-yl]-1-(3-chlorobenzyl)-5-trifluoromethyl-1H-pyrrolo[2,3-b]pyridine-2-carboxamide trifluoroacetate (1:1) (compound No. 49 in Table 2)

LCMS: [MH]$^+$=486
$^1$H NMR (DMSO D$_6$), δ (ppm): 10.71 (s, 1H); 8.84 (s, 1H); 8.78 (s, 1H); 8.39 (s, 1H); 8 (broadened peak, 1H); 7.6 (s, 1H); 7.3 (m, 2H); 7.2 (d, 1H); 7.08 (m, 1H); 6.72 (broadened peak, 1H); 5.94 (s, 2H); 4.1 (m, 4H); 2.4 (m, 2H).

N-[6-(Azetidin-1-yl)-pyridin-3-yl]-1-(3-trifluoromethoxybenzyl)-5-trifluoromethyl-1H-pyrrolo[2,3-b]pyridine-2-carboxamide trifluoroacetate (1:1) (compound No. 50 in Table 2)

LCMS: [MH]$^+$=536
$^1$H NMR (DMSO D$_6$), δ (ppm): 10.71 (s, 1H); 8.83 (s, 1H); 8.78 (s, 1H); 8.38 (s, 1H); 8 (broadened peak, 1H); 7.6 (s, 1H); 7.4 (t, 1H); 7.25 (d, 1H); 7.16 (s, 1H); 7.11 (d, 1H); 6.73 (broadened peak, 1H); 6 (s, 2H); 4.12 (m, 4H); 2.41 (m, 2H).

N-[6-(Azetidin-1-yl)-pyridin-3-yl]-1-(4-methoxybenzyl)-5-trifluoromethyl-1H-pyrrolo[2,3-b]pyridine-2-carboxamide trifluoroacetate (1:1) (compound No. 51 in Table 2)

LCMS: [MH]$^+$=482
$^1$H NMR (DMSO D$_6$), δ (ppm): 10.6 (s, 1H); 8.82 (s, 1H); 8.71 (s, 1H); 8.39 (s, 1H); 8.01 (broadened peak, 1H); 7.51 (s, 1H); 7.11 (d, 2H); 6.82 (d, 1H); 6.71 (broadened peak, 1H); 5.9 (s, 2H); 4.12 (m, 4H); 3.67 (s, 3H); 2.41 (m, 2H).

N-[6-(Azetidin-1-yl)-pyridin-3-yl]-1-(4-methoxybenzyl)-5-fluoro-1H-pyrrolo[2,3-b]pyridine-2-carboxamide trifluoroacetate (1:1) (compound No. 62 in Table 2)

LCMS: [MH]$^+$=432
$^1$H NMR (DMSO D$_6$), δ (ppm): 10.55 (s, 1H); 8.49 (s, 1H); 8.39 (s, 1H); 8.14 (dxd, 1H); 8.01 (broadened peak, 1H); 7.35 (s, 1H); 7.1 (d, 2H); 6.8 (d, 2H); 6.72 (broadened peak, 1H); 5.82 (s, 2H); 4.12 (m, 4H); 3.68 (s, 3H); 2.4 (m, 2H).

N-[6-(Azetidin-1-yl)-pyridin-3-yl]-1-(3-trifluoromethylbenzyl)-6-trifluoromethyl-1H-pyrrolo[2,3-b]pyridine-2-carboxamide trifluoroacetate (1:1) (compound No. 67 in Table 2)

LCMS: [MH]$^+$=520
$^1$H NMR (DMSO D$_6$), δ (ppm): 10.7 (s, 1H); 8.53 (d, 1H); 8.39 (s, 1H); 7.98 (broadened peak, 1H); 7.77 (d, 1H); 7.71 (s, 1H); 7.61 (d, 1H); 7.55 (s, 1H); 7.49 (m, 2H); 6.71 (broadened peak, 1H); 5.98 (s, 2H); 4.12 (m, 4H); 2.39 (m, 2H).

N-[6-(Azetidin-1-yl)-pyridin-3-yl]-1-(4-methylbenzyl)-6-trifluoromethyl-1H-pyrrolo[2,3-b]pyridine-2-carboxamide trifluoroacetate (1:1) (compound No. 68 in Table 2)

LCMS: [MH]$^+$=466
$^1$H NMR (DMSO D$_6$), δ (ppm): 10.68 (s, 1H); 8.51 (d, 1H); 8.39 (s, 1H); 7.98 (broadened peak, 1H); 7.71 (d, 1H); 7.5 (s, 1H); 7.05 (m, 4H); 6.75 (broadened peak, 1H); 5.87 (s, 2H); 4.12 (m, 4H); 2.39 (m, 2H); 2.2 (s, 3H).

N-[6-(Azetidin-1-yl)-pyridin-3-yl]-1-(3-chlorobenzyl)-6-trifluoromethyl-1H-pyrrolo[2,3-b]pyridine-2-carboxamide trifluoroacetate (1:1) (compound No. 71 in Table 2)

LCMS: [MH]$^+$=486
$^1$H NMR (DMSO D$_6$), δ (ppm): 10.7 (s, 1H); 8.54 (d, 1H); 8.36 (s, 1H); 7.98 (broadened peak, 1H); 7.73 (d, 1H); 7.55 (s, 1H); 7.29 (m, 3H); 7.09 (m, 1H); 6.72 (broadened peak, 1H); 5.91 (s, 2H); 4.1 (m, 4H); 2.4 (m, 2H).

N-[6-(Azetidin-1-yl)-pyridin-3-yl]-1-benzyl-1H-pyrrolo[2,3-b]pyridine-2-carboxamide trifluoroacetate (1:1) (compound No. 75 in Table 2)

LCMS: [MH]$^+$=384
$^1$H NMR (DMSO D$_6$), δ (ppm): 10.5 (s, 1H); 8.49 (d, 1H); 8.38 (s, 1H); 8.22 (d, 1H); 8.01 (broadened peak, 1H); 7.41 (s, 1H); 7.22 (m, 4H); 7.09 (m, 2H); 6.72 (broadened peak, 1H); 5.93 (s, 2H); 4.12 (m, 4H); 2.39 (m, 2H).

N-[6-(Azetidin-1-yl)-pyridin-3-yl]-1-(3-trifluoromethylbenzyl)-1H-pyrrolo[2,3-b]pyridine-2-carboxamide trifluoroacetate (1:1) (compound No. 78 in Table 2)

LCMS: [MH]$^+$=452
$^1$H NMR (DMSO D$_6$), δ (ppm): 10.6 (s, 1H); 8.49 (d, 1H); 8.39 (s, 1H); 8.27 (d, 1H); 8.02 (broadened peak, 1H); 7.59 (d, 1H); 7.53 (s, 1H); 7.48 (m, 2H); 7.39 (d, 1H); 7.29 (m, 1H); 6.77 (broadened peak, 1H); 6 (s, 2H); 4.12 (m, 4H); 2.41 (m, 2H).

N-[6-(Azetidin-1-yl)-pyridin-3-yl]-1-(3-methoxybenzyl)-1H-pyrrolo[2,3-b]pyridine-2-carboxamide trifluoroacetate (1:1) (compound No. 81 in Table 2)

LCMS: [MH]$^+$=414
$^1$H NMR (DMSO D$_6$), δ (ppm): 10.5 (s, 1H); 8.47 (d, 1H); 8.39 (s, 1H); 8.21 (d, 1H); 7.98 (broadened peak, 1H); 7.39 (s, 1H); 7.27 (dxd, 1H); 7.13 (m, 1H); 6.78 (m, 1H); 6.7 (broadened peak, 1H); 6.62 (m, 2H); 5.91 (s, 2H); 4.09 (m, 4H); 3.62 (s, 3H); 2.4 (m, 2H).

N-[6-(Azetidin-1-yl)-pyridin-3-yl]-1-(4-methoxybenzyl)-1H-pyrrolo[2,3-b]pyridine-2-carboxamide trifluoroacetate (1:1) (compound No. 84 in Table 2)

LCMS: [MH]$^+$=414
$^1$H NMR (DMSO D$_6$), δ (ppm): 10.31 (s, 1H); 8.47 (d, 1H); 8.38 (s, 1H); 8.19 (d, 1H); 7.91 (broadened peak, 1H); 7.32 (s, 1H); 7.23 (dxd, 1H); 7.1 (m, 2H); 6.78 (m, 2H); 6.57 (broadened peak, 1H); 5.85 (s, 2H); 4.01 (m, 4H); 3.67 (s, 3H); 2.35 (m, 2H).

N-[6-(3-Hydroxyazetidin-1-yl)pyridin-3-yl]-5-fluoro-1-(3-trifluoromethoxybenzyl)-1H-pyrrolo[2,3-b]pyridine-2-carboxamide trifluoroacetate (1:1) (compound No. 115 in Table 2)

LCMS: [MH]$^+$=502
$^1$H NMR (DMSO D$_6$), δ (ppm): 10.51 (s, 1H); 8.48 (s, 1H); 8.35 (s, 1H); 8.19 (d, 1H); 7.92 (broadened peak, 1H); 7.41 (m, 2H); 7.21 (d, 1H); 7.12 (m, 1H); 6.63 (m, 1H); 5.91 (s, 2H); 4.6 (m, 1H); 4.23 (m, 2H); 3.78 (m, 2H).

N-[6-(3-Hydroxyazetidin-1-yl)-pyridin-3-yl]-5-fluoro-1-(4-methoxybenzyl)-1H-pyrrolo[2,3-b]pyridine-2-carboxamide trifluoroacetate (1:1) (compound No. 116 in Table 2)

LCMS: [MH]$^+$=448
$^1$H NMR (DMSO D$_6$), δ (ppm): 10.4 (s, 1H); 8.47 (s, 1H); 8.36 (s, 1H); 8.11 (dxd, 1H); 7.89 (broadened peak, 1H); 7.31 (s, 1H); 7.1 (d, 2H); 6.8 (d, 2H); 6.51 (m, 1H); 5.81 (s, 2H); 4.58 (m, 1H); 4.2 (m, 2H); 3.7 (m, 2H); 3.67 (s, 3H).

N-[6-(3-Hydroxyazetidin-1-yl)-pyridin-3-yl]-5-fluoro-1-(3-chloro-5-trifluoromethyl benzyl)-1H-pyrrolo[2,3-b]pyridine-2-carboxamide trifluoroacetate (1:1) (compound No. 117 in Table 2)

LCMS: [MH]$^+$=520
$^1$H NMR (DMSO D$_6$), δ (ppm): 10.55 (s, 1H); 8.49 (s, 1H); 8.34 (s, 1H); 8.2 (d, 1H); 7.9 (broadened peak, 1H); 7.73 (s, 1H); 7.51 (s, 1H); 7.45 (m, 2H); 6.61 (m, 1H); 5.91 (s, 2H); 4.6 (m, 1H); 4.25 (m, 2H); 3.78 (m, 2H).

N-[6-(3-Hydroxyazetidin-1-yl)-pyridin-3-yl]-1-(3-chlorobenzyl)-1H-pyrrolo[2,3-b]pyridine-2-carboxamide trifluoroacetate (1:1) (compound No. 125 in Table 2)

LCMS: [MH]$^+$=434
$^1$H NMR (DMSO D$_6$), δ (ppm): 10.41 (s, 1H); 8.47 (d, 1H); 8.35 (s, 1H); 8.22 (d, 1H); 7.92 (broadened peak, 1H); 7.41 (s, 1H); 7.29 (m, 3H); 7.12 (s, 1H); 7.05 (d, 1H); 6.62 (m, 1H); 5.91 (s, 2H); 4.61 (m, 1H); 4.25 (m, 2H); 3.78 (m, 2H).

N-[6-(Azetidin-1-yl)-pyridin-3-yl]-1-benzyl-5-trifluoromethyl-1H-pyrrolo[3,2-b]pyridine-2-carboxamide trifluoroacetate (1:1) (compound No. 129 in Table 3)

LCMS: [MH]$^+$=452
$^1$H NMR (DMSO D$_6$), δ (ppm): 10.72 (s, 1H); 8.4 (s, 1H); 8.32 (d, 1H); 8.01 (broadened peak, 1H); 7.78 (d, 1H); 7.61 (s, 1H); 7.26 (m, 3H); 7.11 (m, 2H); 6.72 (broadened peak, 1H); 5.95 (s, 2H); 4.12 (m, 4H); 2.41 (m, 2H).

N-[6-(Azetidin-1-yl)-pyridin-3-yl]-1-(4-fluorobenzyl)-5-trifluoromethyl-1H-pyrrolo[3,2-b]pyridine-2-carboxamide trifluoroacetate (1:1) (compound No. 131 in Table 3)

LCMS: [MH]$^+$=470
$^1$H NMR (DMSO D$_6$), δ (ppm): 10.71 (s, 1H); 8.37 (m, 2H); 8 (broadened peak, 1H); 7.8 (d, 1H); 7.61 (s, 1H); 7.15 (m, 4H); 6.72 (broadened peak, 1H); 5.91 (s, 2H); 4.12 (m, 4H); 2.41 (m, 2H).

N-[6-(Azetidin-1-yl)-pyridin-3-yl]-1-(3-methylbenzyl)-5-trifluoromethyl-1H-pyrrolo[3,2-b]pyridine-2-carboxamide trifluoroacetate (1:1) (compound No. 134 in Table 3)

LCMS: [MH]$^+$=466
$^1$H NMR (DMSO D$_6$), δ (ppm): 10.75 (s, 1H); 8.39 (s, 1H); 8.31 (d, 1H); 8 (broadened peak, 1H); 7.78 (d, 1H); 7.59 (s, 1H); 7.15 (m, 1H); 7.04 (d, 1H); 6.96 (s, 1H); 6.84 (d, 1H); 6.72 (broadened peak, 1H); 5.9 (s, 2H); 4.12 (m, 4H); 2.4 (m, 2H); 2.2 (s, 3H).

N-[6-(Azetidin-1-yl)-pyridin-3-yl]-1-(3-methoxybenzyl)-5-trifluoromethyl-1H-pyrrolo[3,2-b]pyridine-2-carboxamide trifluoroacetate (1:1) (compound No. 135 in Table 3)

LCMS: [MH]$^+$=482
$^1$H NMR (DMSO D$_6$), δ (ppm): 10.75 (s, 1H); 8.4 (s, 1H); 8.31 (d, 1H); 8 (broadened peak, 1H); 7.78 (d, 1H); 7.6 (s, 1H); 7.19 (m, 1H); 6.8 (dxd, 1H); 6.72 (m, 2H); 6.61 (d, 1H); 5.91 (s, 2H); 4.12 (m, 4H); 3.65 (s, 3H); 2.41 (m, 2H).

N-[6-(Azetidin-1-yl)-pyridin-3-yl]-1-(4-methoxybenzyl)-5-trifluoromethyl-1H-pyrrolo[3,2-b]pyridine-2-carboxamide trifluoroacetate (1:1) (compound No. 138 in Table 3)

LCMS: [MH]$^+$=482
$^1$H NMR (DMSO D$_6$), δ (ppm): 10.7 (s, 1H); 8.4 (s, 1H); 8.35 (d, 1H); 8.02 (broadened peak, 1H); 7.78 (d, 1H); 7.58 (s, 1H); 7.11 (d, 2H); 6.84 (d, 2H); 6.75 (broadened peak, 1H); 5.87 (s, 2H); 4.12 (m, 4H); 3.69 (s, 3H); 2.39 (m, 2H).

N-[6-(3-Hydroxyazetidin-1-yl)-pyridin-3-yl]-1-(3-trifluoromethyl benzyl)-1H-pyrrolo[2,3-c]pyridine-2-carboxamide trifluoroacetate (1:1) (compound No. 164 in Table 4)

LCMS: [MH]$^+$=468
$^1$H NMR (DMSO D$_6$), δ (ppm): 10.8 (s, 1H); 9.51 (s, 1H); 8.92 (s, 1H); 8.88 (s, 1H); 8.44 (d, 1H); 8.32 (m, 2H); 7.85 (broadened peak, 1H); 7.63 (m, 2H); 7.53 (m, 1H); 7.39 (d, 1H); 6.51 (broadened peak, 1H); 6.09 (s, 2H); 4.58 (m, 1H); 4.2 (m, 2H); 3.71 (m, 2H).

N-[6-(3-Hydroxyazetidin-1-yl)-pyridin-3-yl]-1-(4-methyl benzyl)-1H-pyrrolo[2,3-c]pyridine-2-carboxamide trifluoroacetate (1:1) (compound No. 165 in Table 4)

LCMS: [MH]$^+$=414
$^1$H NMR (DMSO D$_6$), δ (ppm): 10.75 (s, 1H); 8.93 (s, 1H); 8.9 (s, 1H); 8.35 (m, 3H); 7.88 (broadened peak, 1H); 7.59 (s, 1H); 7.09 (m, 4H); 6.51 (broadened peak, 1H); 5.95 (s, 2H); 4.59 (m, 1H); 4.2 (m, 2H); 3.72 (m, 2H); 2.22 (s, 3H).

The following Tables 2, 3 and 4 illustrate the chemical structures and the physical properties of some compounds of general formula (I) according to the invention.

In these tables:
- the column "MP (° C.) or [MH]$^+$" shows, respectively, either the melting points of the products in degrees Celsius (° C.), or their mass peak in LC-MS;
- in the column "Salt/base", "-" represents a compound in the form of free base, whereas "HCl" represents a compound in the form of hydrochloride and "TFA" represents a compound in the form of trifluoroacetate; the ratio in parentheses is the (acid:base) ratio;
- "CH$_3$" corresponds to a methyl group, "Et" corresponds to an ethyl group, "CF$_3$" corresponds to a trifluoromethyl group, <<NC$_4$H$_8$" to a pyrrolidin-1-yl group.

TABLE 2

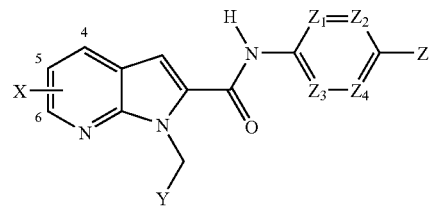

| No. | X | Y | Z$_1$, Z$_2$, Z$_3$, Z$_4$ | Z | salt | MP (° C.) or [MH]$^+$ |
|---|---|---|---|---|---|---|
| 1 | 5-CF$_3$ | 3-fluorophenyl | CH, CH, CH, N | NHCH$_3$ | — | 252-254 |
| 2 | 5-CF$_3$ | 3-fluorophenyl | CH, C(CH$_3$), CH, N | N(CH$_3$)$_2$ | HCl 1:1 | 252-257 |
| 3 | 5-CF$_3$ | 3-fluorophenyl | C(CH$_3$), CH, CH, N | N(CH$_3$)$_2$ | HCl 1:1 | 242-247 |
| 4 | 5-CF$_3$ | 3-fluorophenyl | CH, C(CH$_3$), CH, N | N(CH$_3$)$_2$ | HCl 1:1 | 213-218 |
| 5 | 5-F | 3-fluorophenyl | CH, CH, CH, N | NC$_4$H$_8$ | — | 239-240 |
|  |  |  |  |  | HCl 2:3 | 241-242 |
| 6 | 5-CF$_3$ | 3-fluorophenyl | CH, CH, CH, N | NC$_4$H$_8$ | — | 234-236 |
| 7 | 5-CF$_3$ | 3-fluorophenyl | N, CH, CH, N | NC$_4$H$_8$ | — | 182-183 |
| 8 | 5-CF$_3$ | 3-fluorophenyl | CH, CH, N, N | (CH$_3$)$_2$ | — | 224-226 |
| 9 | 5-CF$_3$ | pyridin-4-yl | CH, CH, CH, N | NC$_4$H$_8$ | — | 244-245 |
| 10 | 5-CF$_3$ | 3-fluorophenyl | CH, CH, CH, N | NHCH(CH$_3$)$_2$ | — | 210-212 |
| 11 | 5-CF$_3$ | 3-fluorophenyl | CH, CH, CH, N | 3-hydroxy-pyrrolidinyl | — | 233-235 |
| 12 | 5-CF$_3$ | 3-fluorophenyl | CH, CH, CH, N | 3,3-difluoro-pyrrolidinyl | — | 211-213 |
| 13 | 5-CF$_3$ | 3-fluorophenyl | CH, CH, CH, N | N(CH$_3$)$_2$ | — | 233-235 |
| 14 | 5-CF$_3$ | 3-fluorophenyl | CH, CH, CH, N | cis-2,5-dimethyl-pyrrolidinyl | — | [MH]$^+$ = 512 |
| 15 | 5-CF$_3$ | 3-fluorophenyl | CH, CH, CH, N | azetidinyl | — | 243-244 |
|  |  |  |  |  | HCl 1:1 | 230-235 |
| 17 | 5-CF$_3$ | 3-fluorophenyl | CH, CH, CH, N | (S)-prolinyl | — | 235-237 |
| 18 | 5-CF$_3$ | 3-fluorophenyl | CH, CH, CH, N | (S)-prolinyl ter-butyl ester | — | 106-108 |
| 19 | 5-CF$_3$ | 3-fluorophenyl | CH, CH, CH, N | 3,3-difluoro azetidinyl | — | 222-224 |
| 20 | 5-CF$_3$ | 3-fluorophenyl | CH, CH, CH, N | 3-hydroxy azetidinyl | — | 221-223 |

TABLE 2-continued

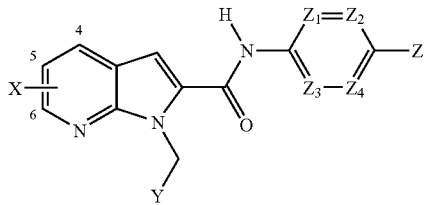

| No. | X | Y | $Z_1, Z_2, Z_3, Z_4$ | Z | salt | MP (° C.) or [MH]+ |
|---|---|---|---|---|---|---|
| 21 | 5-$CF_3$ | 3-fluorophenyl | C($CH_3$), CH, CH, N | N($CH_3$)$_2$ | — | 222-223 |
| 22 | 6-$CF_3$ | 3-fluorophenyl | C($CH_3$), CH, CH, N | N$C_4H_8$ | — | 202-203 |
| 23 | 5-$CF_3$ | 3-fluorophenyl | CH, CH, CH, N | 3-methoxy pyrrolidinyl | — | 154-156 |
| 24 | 5-$CF_3$ | pyridin-4-yl | C($CH_3$), CH, CH, N | N($CH_3$)$_2$ | — | 241-242 |
| 25 | 5-$CF_3$ | 3-fluorophenyl | C($CH_3$),CH, CH, N | N$C_4H_8$ | — | 225-226 |
| 26 | 6-$CF_3$ | pyridin-4-yl | C($CH_3$),CH, CH, N | N$C_4H_8$ | — | 240-241 |
| 27 | 5-$CF_3$ | pyridin-4-yl | C($CH_3$),CH, CH, N | N$C_4H_8$ | — | 251-252 |
| 28 | 5-$CF_3$ | pyridin-4-yl | C($CH_3$), CH, CH, N | NH$CH_3$ | — | 230-231 |
| 29 | 5-$CF_3$ | pyridin-4-yl | C(O$CH_3$), CH, CH, N | N$C_4H_8$ | — | 222-224 |
| 30 | 5-$CF_3$ | pyridin-4-yl | CH, CH, CH, N | azetidinyl | — | 233-235 |
| 31 | 5-$CF_3$ | 3-fluorophenyl | CH, CH, CH, N | NHC(O)$CH_3$ | — | 282-284 |
| 32 | 5-$CF_3$ | 3-fluorophenyl | CH, CH, CH, N | $NH_2$ | — | 230-232 |
| 33 | 6-$CF_3$ | 3-fluorophenyl | CH, CH, CH, N | N$C_4H_8$ | — | 204-205 |
| 34 | 5-$CF_3$ | 3-fluorophenyl | C($CF_3$), CH, CH, N | N$C_4H_8$ | — | 207-208 |
| 35 | 5-$CF_3$ | 3-fluorophenyl | CH, C(F), CH, N | N($CH_3$)$_2$ | — | 199-200 |
| 36 | 5-$CF_3$ | 3-fluorophenyl | CH, N, CH, N | N($CH_3$)$_2$ | — | 236-238 |
| 37 | 5-$CF_3$ | 3-fluorophenyl | CH, CH, CH, N | 3-azabicyclo [3,2,0]heptyl | — | 172-174 |
| 38 | 5-$CF_3$ | 3-fluorophenyl | CH, CH, CH, N | 3-azabicyclo [3,1,0]hexyl | — | 212-214 |
| 39 | 5-F | 3-fluorophenyl | CH, CH, CH, N | 3-azabicyclo [3,1,0]hexyl | — | 222-224 |
| 40 | 5-$CF_3$ | 3-fluorophenyl | CH, CH, CH, N | NH($CH_2$)$_2$$CO_2$H | — | 196-199 |
| 41 | 5-$CF_3$ | 3-fluorophenyl | CH, CH, CH, N | NH($CH_2$)$_3$OH | — | 207-210 |
| 42 | 5-$CF_3$ | phenyl | CH, CH, CH, N | azetidinyl | TFA 1:1 | [MH]+ 452 |
| 43 | 5-$CF_3$ | 2-fluorophenyl | CH, CH, CH, N | azetidinyl | TFA 1:1 | [MH]+ 470 |
| 44 | 5-$CF_3$ | 4-fluorophenyl | CH, CH, CH, N | azetidinyl | TFA 1:1 | [MH]+ 470 |
| 45 | 5-$CF_3$ | 3-trifluoro methylphenyl | CH, CH, CH, N | azetidinyl | TFA 1:1 | [MH]+ 520 |
| 46 | 5-$CF_3$ | 4-methylphenyl | CH, CH, CH, N | azetidinyl | TFA 1:1 | [MH]+ 466 |
| 47 | 5-$CF_3$ | 3-methylphenyl | CH, CH, CH, N | azetidinyl | TFA 1:1 | [MH]+ 466 |
| 48 | 5-$CF_3$ | 3-methoxy phenyl | CH, CH, CH, N | azetidinyl | TFA 1:1 | [MH]+ 482 |
| 49 | 5-$CF_3$ | 3-chlorophenyl | CH, CH, CH, N | azetidinyl | TFA 1:1 | [MH]+ 486 |
| 50 | 5-$CF_3$ | 3-trifluoro methoxyphenyl | CH, CH, CH, N | azetidinyl | TFA 1:1 | [MH]+ 536 |
| 51 | 5-$CF_3$ | 4-methoxyphenyl | CH, CH, CH, N | azetidinyl | TFA 1:1 | [MH]+ 482 |
| 52 | 5-$CF_3$ | 3-chloro-5-trifluoro methylphenyl | CH, CH, CH, N | azetidinyl | TFA 1:1 | [MH]+ 554 |
| 53 | 5-F | phenyl | CH, CH, CH, N | azetidinyl | TFA 1:1 | [MH]+ 402 |
| 54 | 5-F | 2-fluorophenyl | CH, CH, CH, N | azetidinyl | TFA 1:1 | [MH]+ 420 |
| 55 | 5-F | 4-fluorophenyl | CH, CH, CH, N | azetidinyl | TFA 1:1 | [MH]+ 420 |
| 56 | 5-F | 3-trifluoro methylphenyl | CH, CH, CH, N | azetidinyl | TFA 1:1 | [MH]+ 470 |

TABLE 2-continued

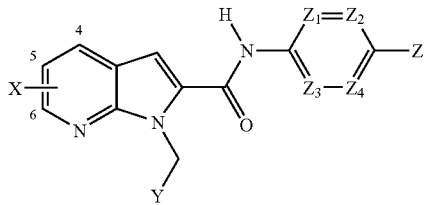

| No. | X | Y | $Z_1, Z_2, Z_3, Z_4$ | Z | salt | MP (° C.) or [MH]+ |
|---|---|---|---|---|---|---|
| 57 | 5-F | 4-methylphenyl | CH, CH, CH, N | azetidinyl | TFA 1:1 | [MH]+ 416 |
| 58 | 5-F | 3-methylphenyl | CH, CH, CH, N | azetidinyl | TFA 1:1 | [MH]+ 416 |
| 59 | 5-F | 3-methoxy phenyl | CH, CH, CH, N | azetidinyl | TFA 1:1 | [MH]+ 432 |
| 60 | 5-F | 3-chlorophenyl | CH, CH, CH, N | azetidinyl | TFA 1:1 | [MH]+ 436 |
| 61 | 5-F | 3-trifluoro methoxyphenyl | CH, CH, CH, N | azetidinyl | TFA 1:1 | [MH]+ 486 |
| 62 | 5-F | 4-methoxy phenyl | CH, CH, CH, N | azetidinyl | TFA 1:1 | [MH]+ 432 |
| 63 | 5-F | 3-chloro-5-trifluoro methylphenyl | CH, CH, CH, N | azetidinyl | TFA 1:1 | [MH]+ 504 |
| 64 | 6-CF$_3$ | phenyl | CH, CH, CH, N | azetidinyl | TFA 1:1 | [MH]+ 452 |
| 65 | 6-CF$_3$ | 2-fluorophenyl | CH, CH, CH, N | azetidinyl | TFA 1:1 | [MH]+ 470 |
| 66 | 6-CF$_3$ | 4-fluorophenyl | CH, CH, CH, N | azetidinyl | TFA 1:1 | [MH]+ 470 |
| 67 | 6-CF$_3$ | 3-trifluoro methylphenyl | CH, CH, CH, N | azetidinyl | TFA 1:1 | [MH]+ 520 |
| 68 | 6-CF$_3$ | 4-methylphenyl | CH, CH, CH, N | azetidinyl | TFA 1:1 | [MH]+ 466 |
| 69 | 6-CF$_3$ | 3-methylphenyl | CH, CH, CH, N | azetidinyl | TFA 1:1 | [MH]+ 466 |
| 70 | 6-CF$_3$ | 3-methoxy phenyl | CH, CH, CH, N | azetidinyl | TFA 1:1 | [MH]+ 482 |
| 71 | 6-CF$_3$ | 3-chlorophenyl | CH, CH, CH, N | azetidinyl | TFA 1:1 | [MH]+ 486 |
| 72 | 6-CF$_3$ | 3-trifluoro methyoxyphenyl | CH, CH, CH, N | azetidinyl | TFA 1:1 | [MH]+ 536 |
| 73 | 6-CF$_3$ | 4-methoxy phenyl | CH, CH, CH, N | azetidinyl | TFA 1:1 | [MH]+ 482 |
| 74 | 6-CF$_3$ | 3-chloro-5-trifluoro methylphenyl | CH, CH, CH, N | azetidinyl | TFA 1:1 | [MH]+ 554 |
| 75 | H | phenyl | CH, CH, CH, N | azetidinyl | TFA 1:1 | [MH]+ 384 |
| 76 | H | 2-fluorophenyl | CH, CH, CH, N | azetidinyl | TFA 1:1 | [MH]+ 402 |
| 77 | H | 4-fluorophenyl | CH, CH, CH, N | azetidinyl | TFA 1:1 | [MH]+ 402 |
| 78 | H | 3-trifluoro methylphenyl | CH, CH, CH, N | azetidinyl | TFA 1:1 | [MH]+ 452 |
| 79 | H | 4-methylphenyl | CH, CH, CH, N | azetidinyl | 1:1 | [MH]+ 398 |
| 80 | H | 3-methylphenyl | CH, CH, CH, N | azetidinyl | TFA 1:1 | [MH]+ 398 |
| 81 | H | 3-methoxy phenyl | CH, CH, CH, N | azetidinyl | TFA 1:1 | [MH]+ 414 |
| 82 | H | 3-chlorophenyl | CH, CH, CH, N | azetidinyl | TFA | [MH]+ 418 |
| 83 | H | 3-trifluoro methoxyphenyl | CH, CH, CH, N | azetidinyl | TFA 1:1 | [MH]+ 468 |
| 84 | H | 4-methoxy phenyl | CH, CH, CH, N | azetidinyl | TFA 1:1 | [MH]+ 414 |
| 85 | H | 3-chloro-5-trifluoro methylphenyl | CH, CH, CH, N | azetidinyl | TFA 1:1 | [MH]+ 486 |
| 86 | 5-CF$_3$ | 2-fluorophenyl | CH, CH, CH, N | 3-hydroxy azetidinyl | TFA 1:1 | [MH]+ 486 |
| 87 | 5-CF$_3$ | 4-fluorophenyl | CH, CH, CH, N | 3-hydroxy azetidinyl | TFA 1:1 | [MH]+ 486 |

TABLE 2-continued

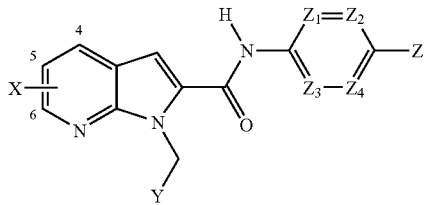

| No. | X | Y | $Z_1, Z_2, Z_3, Z_4$ | Z | salt | MP (° C.) or [MH]$^+$ |
|---|---|---|---|---|---|---|
| 88 | 5-CF$_3$ | 3-trifluoro methylphenyl | CH, CH, CH, N | 3-hydroxy azetidinyl | TFA 1:1 | [MH]$^+$ 536 |
| 89 | 5-CF$_3$ | 4-methylphenyl | CH, CH, CH, N | 3-hydroxy azetidinyl | TFA 1:1 | [MH]$^+$ 482 |
| 90 | 5-CF$_3$ | 3-methylphenyl | CH, CH, CH, N | 3-hydroxy azetidinyl | TFA 1:1 | [MH]$^+$ 482 |
| 91 | 5-CF$_3$ | 3-methoxy phenyl | CH, CH, CH, N | 3-hydroxy azetidinyl | TFA 1:1 | [MH]$^+$ 498 |
| 92 | 5-CF$_3$ | 3-chlorophenyl | CH, CH, CH, N | 3-hydroxy azetidinyl | TFA 1:1 | [MH]$^+$ 502 |
| 93 | 5-CF$_3$ | 3-trifluoro methoxyphenyl | CH, CH, CH, N | 3-hydroxy azetidinyl | TFA 1:1 | [MH]$^+$ 552 |
| 94 | 5-CF$_3$ | 4-methoxy phenyl | CH, CH, CH, N | 3-hydroxy azetidinyl | TFA 1:1 | [MH]$^+$ 498 |
| 95 | 5-CF$_3$ | 3-chloro-5-trifluoro methylphenyl | CH, CH, CH, N | 3-hydroxy azetidinyl | TFA 1:1 | [MH]$^+$ 570 |
| 96 | 6-CF$_3$ | phenyl | CH, CH, CH, N | 3-hydroxy azetidinyl | TFA 1:1 | [MH]$^+$ 468 |
| 97 | 6-CF$_3$ | 2-fluorophenyl | CH, CH, CH, N | 3-hydroxy azetidinyl | TFA 1:1 | [MH]$^+$ 486 |
| 98 | 6-CF$_3$ | 4-fluorophenyl | CH, CH, CH, N | 3-hydroxy azetidinyl | TFA 1:1 | [MH]$^+$ 486 |
| 99 | 6-CF$_3$ | 3-trifluoro methylphenyl | CH, CH, CH, N | 3-hydroxy azetidinyl | TFA 1:1 | [MH]$^+$ 536 |
| 100 | 6-CF$_3$ | 4-methylphenyl | CH, CH, CH, N | 3-hydroxy azetidinyl | TFA 1:1 | [MH]$^+$ 482 |
| 101 | 6-CF$_3$ | 3-methylphenyl | CH, CH, CH, N | 3-hydroxy azetidinyl | TFA 1:1 | [MH]$^+$ 482 |
| 102 | 6-CF$_3$ | 3-methoxyphenyl | CH, CH, CH, N | 3-hydroxy azetidinyl | TFA 1:1 | [MH]$^+$ 498 |
| 103 | 6-CF$_3$ | 3-chlorophenyl | CH, CH, CH, N | 3-hydroxy azetidinyl | TFA 1:1 | [MH]$^+$ 502 |
| 104 | 6-CF$_3$ | 3-trifluoro methoxyphenyl | CH, CH, CH, N | 3-hydroxy azetidinyl | TFA 1:1 | [MH]$^+$ 552 |
| 105 | 6-CF$_3$ | 4-methoxyphenyl | CH, CH, CH, N | 3-hydroxy azetidinyl | TFA 1:1 | [MH]$^+$ 498 |
| 106 | 6-CF$_3$ | 3-chloro-5-trifluoro methylphenyl | CH, CH, CH, N | 3-hydroxy azetidinyl | TFA 1:1 | [MH]$^+$ 570 |
| 107 | 5-F | phenyl | CH, CH, CH, N | 3-hydroxy azetidinyl | TFA 1:1 | [MH]$^+$ 418 |
| 108 | 5-F | 2-fluorophenyl | CH, CH, CH, N | 3-hydroxy azetidinyl | TFA 1:1 | [MH]$^+$ 436 |
| 109 | 5-F | 4-fluorophenyl | CH, CH, CH, N | 3-hydroxy azetidinyl | TFA 1:1 | [MH]$^+$ 436 |
| 110 | 5-F | 3-trifluoro methylphenyl | CH, CH, CH, N | 3-hydroxy azetidinyl | TFA 1:1 | [MH]$^+$ 486 |
| 111 | 5-F | 4-methylphenyl | CH, CH, CH, N | 3-hydroxy azetidinyl | TFA 1:1 | [MH]$^+$ 432 |
| 112 | 5-F | 3-methylphenyl | CH, CH, CH, N | 3-hydroxy azetidinyl | TFA 1:1 | [MH]$^+$ 432 |
| 113 | 5-F | 3-methoxy phenyl | CH, CH, CH, N | 3-hydroxy azetidinyl | TFA 1:1 | [MH]$^+$ 448 |
| 114 | 5-F | 3-chlorophenyl | CH, CH, CH, N | 3-hydroxy azetidinyl | TFA 1:1 | [MH]$^+$ 452 |
| 115 | 5-F | 3-trifluoro methoxyphenyl | CH, CH, CH, N | 3-hydroxy azetidinyl | TFA 1:1 | [MH]$^+$ 502 |
| 116 | 5-F | 4-methoxy phenyl | CH, CH, CH, N | 3-hydroxy azetidinyl | TFA 1:1 | [MH]$^+$ 448 |
| 117 | 5-F | 3-chloro-5-trifluoro methylphenyl | CH, CH, CH, N | 3-hydroxy azetidinyl | TFA 1:1 | [MH]$^+$ 520 |
| 118 | H | phenyl | CH, CH, CH, N | 3-hydroxy azetidinyl | TFA 1:1 | [MH]$^+$ 400 |

TABLE 2-continued

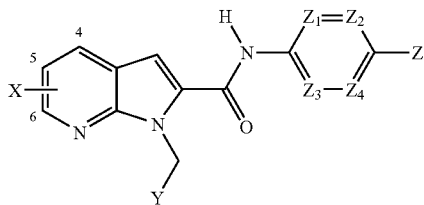

| No. | X | Y | $Z_1, Z_2, Z_3, Z_4$ | Z | salt | MP (° C.) or [MH]+ |
|---|---|---|---|---|---|---|
| 119 | H | 2-fluorophenyl | CH, CH, CH, N | 3-hydroxy azetidinyl | TFA 1:1 | [MH]+ 418 |
| 120 | H | 4-fluorophenyl | CH, CH, CH, N | 3-hydroxy azetidinyl | TFA 1:1 | [MH]+ 418 |
| 121 | H | 3-trifluoro methylphenyl | CH, CH, CH, N | 3-hydroxy azetidinyl | TFA 1:1 | [MH]+ 468 |
| 122 | H | 4-methylphenyl | CH, CH, CH, N | 3-hydroxy azetidinyl | TFA 1:1 | [MH]+ 414 |
| 123 | H | 3-methylphenyl | CH, CH, CH, N | 3-hydroxy azetidinyl | TFA 1:1 | [MH]+ 414 |
| 124 | H | 3-methoxy phenyl | CH, CH, CH, N | 3-hydroxy azetidinyl | TFA 1:1 | [MH]+ 430 |
| 125 | H | 3-chlorophenyl | CH, CH, CH, N | 3-hydroxy azetidinyl | TFA 1:1 | [MH]+ 434 |
| 126 | H | 3-trifluoro methoxyphenyl | CH, CH, CH, N | 3-hydroxy azetidinyl | TFA 1:1 | [MH]+ 484 |
| 127 | H | 4-methoxy phenyl | CH, CH, CH, N | 3-hydroxy azetidinyl | TFA 1:1 | [MH]+ 430 |
| 128 | H | 3-chloro-5-trifluoro methylphenyl | CH, CH, CH, N | 3-hydroxy azetidinyl | TFA 1:1 | [MH]+ 502 |
| 171 | 5-CF$_3$ | 3-fluorophenyl | CH, CH, CH, N | NH(CH$_2$)$_2$CO$_2$Et | — | [MH]+ 530 |
| 172 | 5-CF$_3$ | 3-fluorophenyl | CH, CH, CH, N | 3-(methoxy) azetidinyl | — | 185-187 |
| 173 | 5-CF$_3$ | 3-fluorophenyl | CH, CH, CH, N | 3-(cyclopropyl methyloxy) azetidinyl | — | 201-203 |

TABLE 3

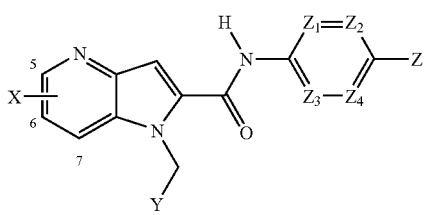

| No. | X | Y | $Z_1, Z_2, Z_3, Z_4$ | Z | salt | MP (° C.) |
|---|---|---|---|---|---|---|
| 16 | 5-CF$_3$ | 3-fluorophenyl | CH, CH, CH, N | NC$_4$H$_8$ | — | 219-220 |
| 129 | 5-CF$_3$ | phenyl | CH, CH, CH, N | azetidinyl | TFA 1:1 | [MH]+ 452 |
| 130 | 5-CF$_3$ | 2-fluorophenyl | CH, CH, CH, N | azetidinyl | TFA 1:1 | [MH]+ 470 |
| 131 | 5-CF$_3$ | 4-fluorophenyl | CH, CH, CH, N | azetidinyl | TFA 1:1 | [MH]+ 470 |
| 132 | 5-CF$_3$ | 3-trifluoro methylphenyl | CH, CH, CH, N | azetidinyl | TFA 1:1 | [MH]+ 520 |
| 133 | 5-CF$_3$ | 4-methylphenyl | CH, CH, CH, N | azetidinyl | TFA 1:1 | [MH]+ 466 |
| 134 | 5-CF$_3$ | 3-methylphenyl | CH, CH, CH, N | azetidinyl | TFA 1:1 | [MH]+ 466 |
| 135 | 5-CF$_3$ | 3-methoxyphenyl | CH, CH, CH, N | azetidinyl | TFA 1:1 | [MH]+ 482 |
| 136 | 5-CF$_3$ | 3-chlorophenyl | CH, CH, CH, N | azetidinyl | TFA 1:1 | [MH]+ 486 |

TABLE 3-continued

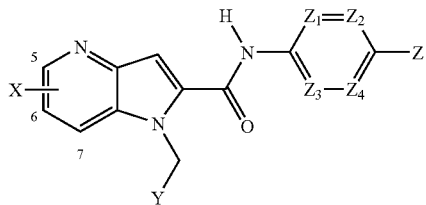

| No. | X | Y | $Z_1, Z_2, Z_3, Z_4$ | Z | salt | MP (° C.) |
|---|---|---|---|---|---|---|
| 137 | 5-$CF_3$ | 3-trifluoro methoxyphenyl | CH, CH, CH, N | azetidinyl | TFA 1:1 | $[MH]^+$ 536 |
| 138 | 5-$CF_3$ | 4-methoxyphenyl | CH, CH, CH, N | azetidinyl | TFA 1:1 | $[MH]^+$ 482 |
| 139 | 5-$CF_3$ | 3-chloro-5-trifluoro methylphenyl | CH, CH, CH, N | azetidinyl | TFA 1:1 | $[MH]^+$ 554 |
| 140 | 5-$CF_3$ | phenyl | CH, CH, CH, N | 3-hydroxy azetidinyl | TFA 1:1 | $[MH]^+$ 468 |
| 141 | 5-$CF_3$ | 2-fluorophenyl | CH, CH, CH, N | 3-hydroxy azetidinyl | TFA 1:1 | $[MH]^+$ 468 |
| 142 | 5-$CF_3$ | 4-fluorophenyl | CH, CH, CH, N | 3-hydroxy azetidinyl | TFA 1:1 | $[MH]^+$ 468 |
| 143 | 5-$CF_3$ | 3-trifluoro methylphenyl | CH, CH, CH, N | 3-hydroxy azetidinyl | TFA 1:1 | $[MH]^+$ 536 |
| 144 | 5-$CF_3$ | 4-methylphenyl | CH, CH, CH, N | 3-hydroxy azetidinyl | TFA 1:1 | $[MH]^+$ 482 |
| 145 | 5-$CF_3$ | 3-methylphenyl | CH, CH, CH, N | 3-hydroxy azetidinyl | TFA 1:1 | $[MH]^+$ 482 |
| 146 | 5-$CF_3$ | 3-methoxyphenyl | CH, CH, CH, N | 3-hydroxy azetidinyl | TFA 1:1 | $[MH]^+$ 498 |
| 147 | 5-$CF_3$ | 3-chlorophenyl | CH, CH, CH, N | 3-hydroxy azetidinyl | TFA 1:1 | $[MH]^+$ 502 |
| 148 | 5-$CF_3$ | 3-trifluoro methoxyphenyl | CH, CH, CH, N | 3-hydroxy azetidinyl | TFA 1:1 | $[MH]^+$ 552 |
| 149 | 5-$CF_3$ | 4-methoxyphenyl | CH, CH, CH, N | 3-hydroxy azetidinyl | TFA 1:1 | $[MH]^+$ 498 |
| 150 | 5-$CF_3$ | 3-chloro-5-trifluoro methylphenyl | CH, CH, CH, N | 3-hydroxy azetidinyl | TFA 1:1 | $[MH]^+$ 554 |

TABLE 4

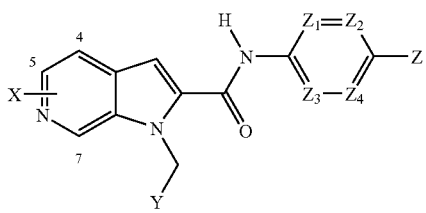

| No. | X | Y | $Z_1, Z_2, Z_3, Z_4$ | Z | salt | MP (° C.) |
|---|---|---|---|---|---|---|
| 151 | H | phenyl | CH, CH, CH, N | azetidinyl | TFA 1:1 | $[MH]^+$ 384 |
| 152 | H | 2-fluorophenyl | CH, CH, CH, N | azetidinyl | TFA 1:1 | $[MH]^+$ 402 |
| 153 | H | 4-fluorophenyl | CH, CH, CH, N | azetidinyl | TFA 1:1 | $[MH]^+$ 402 |
| 154 | H | 3-trifluoro methylphenyl | CH, CH, CH, N | azetidinyl | TFA 1:1 | $[MH]^+$ 452 |
| 155 | H | 4-methylphenyl | CH, CH, CH, N | azetidinyl | TFA 1:1 | $[MH]^+$ 398 |
| 156 | H | 3-methylphenyl | CH, CH, CH, N | azetidinyl | TFA 1:1 | $[MH]^+$ 398 |
| 157 | H | 3-methoxy phenyl | CH, CH, CH, N | azetidinyl | TFA 1:1 | $[MH]^+$ 414 |
| 158 | H | 3-chlorophenyl | CH, CH, CH, N | azetidinyl | TFA 1:1 | $[MH]^+$ 418 |

TABLE 4-continued

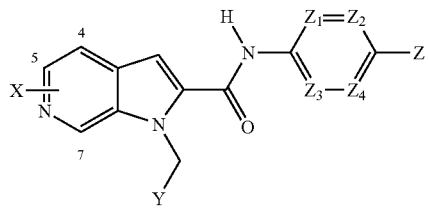

| No. | X | Y | $Z_1, Z_2, Z_3, Z_4$ | Z | salt | MP (° C.) |
|---|---|---|---|---|---|---|
| 159 | H | 3-trifluoro methoxyphenyl | CH, CH, CH, N | azetidinyl | TFA 1:1 | [MH]$^+$ 468 |
| 160 | H | 3-chloro-5-trifluoro methylphenyl | CH, CH, CH, N | azetidinyl | TFA 1:1 | [MH]$^+$ 486 |
| 161 | H | phenyl | CH, CH, CH, N | 3-hydroxy azetidinyl | TFA 1:1 | [MH]$^+$ 400 |
| 162 | H | 2-fluorophenyl | CH, CH, CH, N | 3-hydroxy azetidinyl | TFA 1:1 | [MH]$^+$ 418 |
| 163 | H | 4-fluorophenyl | CH, CH, CH, N | 3-hydroxy azetidinyl | TFA 1:1 | [MH]$^+$ 418 |
| 164 | H | 3-trifluoro methylphenyl | CH, CH, CH, N | 3-hydroxy azetidinyl | TFA 1:1 | [MH]$^+$ 468 |
| 165 | H | 4-methylphenyl | CH, CH, CH, N | 3-hydroxy azetidinyl | TFA 1:1 | [MH]$^+$ 414 |
| 166 | H | 3-methylphenyl | CH, CH, CH, N | 3-hydroxy azetidinyl | TFA 1:1 | [MH]$^+$ 414 |
| 167 | H | 3-methoxy phenyl | CH, CH, CH, N | 3-hydroxy azetidinyl | TFA 1:1 | [MH]$^+$ 430 |
| 168 | H | 3-chlorophenyl | CH, CH, CH, N | 3-hydroxy azetidinyl | TFA 1:1 | [MH]$^+$ 434 |
| 169 | H | 3-trifluoro methoxyphenyl | CH, CH, CH, N | 3-hydroxy azetidinyl | TFA 1:1 | [MH]$^+$ 484 |
| 170 | H | 3-chloro-5-trifluoro methylphenyl | CH, CH, CH, N | 3-hydroxy azetidinyl | TFA 1:1 | [MH]$^+$ 502 |

The compounds of the invention underwent pharmacological testing in vitro and in vivo and this demonstrated that they are interesting as substances with therapeutic effects.

The compounds of the invention also display characteristics of solubility in water, which favors good activity in vivo.

Test of Inhibition of the Current Induced by Capsaicin on the Rat DRG

Primary Culture of Rat Dorsal Root Ganglion (DRG) Cells:

The neurons of the DRG express the TRPV1 receptor naturally.

Primary cultures of DRG of neonate rats are prepared from 1-day-old rats. Briefly, after dissection, the ganglia are trypsinized and the cells are dissociated mechanically by careful trituration. The cells are resuspended in Eagle's basic culture medium containing 10% of fetal calf serum, 25 mM KCl, 2 mM glutamine, 100 µg/ml gentamicin and 50 ng/ml of NGF, then deposited on glass slides covered with laminin (0.25×10$^6$ cells per slide), which are then placed in Corning 12-well plates. The cells are incubated at 37° C. in a humidified atmosphere containing 5% $CO_2$ and 95% air. Cytosine β-D-arabinoside (1 µM) is added 48 h after culture set-up, to prevent the development of non-neuronal cells. The slides are transferred to the test chambers for patch-clamp investigations after 7-10 days in culture.

Electrophysiology:

The measuring chambers (volume 800 µl) containing the cellular preparation are placed on the stage of an inverted microscope (Olympus IMT2) fitted with Hoffman optics (Modulation Contrast, New York) and are observed at magnification of 400×. The chambers are continually perfused by gravity (2.5 ml/min) by means of a solution distributor accepting 8 inlets and whose single outlet, comprising a polyethylene tube (inside diameter 500 µm) is positioned at less than 3 mm from the cell under investigation. The "whole-cell" configuration of the patch-clamp technique was used. Pipettes of borosilicate glass (resistance 5-10 MOhms) are brought up to the cell by means of a piezoelectric 3D micromanipulator (Burleigh, PC1000). The total currents (membrane potential fixed at −60 mV) were recorded with an Axopatch 1 D amplifier (Axon Instruments, Foster City, Calif.), connected to a PC controlled by Pclamp8 software (Axon Instrument). The current traces are recorded on paper and simultaneously digitized (sampling frequency 15 to 25 Hz) and saved to the hard disk of the PC.

The application of a micromolar solution of capsaicin induces a cationic input current on the DRG cells (voltage fixed at −70 mV). In order to minimize the desensitization of the receptors, a minimum interval of one minute is observed between two applications of capsaicin. After a control period (stabilization of the capsaicin response alone), the test compounds are applied alone at a specified concentration (concentration of 10 nM or of 0.1 nM) for a duration of 4 to 5 minutes, during which several capsaicin+compound tests are performed (for obtaining maximum inhibition). The results are expressed as percentage inhibition of the capsaicin control response.

The percentage inhibition of the capsaicin response (1 microM) is between 20% and 100% for the most active compounds of the invention tested at a concentration from 10 nM to 0.1 nM (see example in Table 5).

The compounds of the invention are therefore effective antagonists in vitro of the type TRPV1 receptors.

TABLE 5

| Compound No. | Percentage inhibition in patch DRG |
| --- | --- |
| 4 | 98% (1 nM) |
| 6 | 71% (1 nM) |
| 15 | 100% (10 nM) |

Mouse Cornea Irritation Test

The irritant nature of capsaicin is easily appreciated at the level of the cornea since this organ is one of the most innervated with the C-fibres. In this context, according to preliminary experiments, the application of a very small amount of capsaicin (2 µl at a concentration of 160 µM) to the surface of the cornea of an animal leads to a certain number of stereotypical behaviors associated with irritation, which are easily listed. These include: blinking, rubbing of the instilled eye by the ipsilateral forepaw, rubbing of the face with both forepaws, scratching of the ipsilateral face by the hindpaw. The duration of these behaviors does not exceed 2 minutes of observation, and the animal then resumes its normal activity. Moreover, its appearance is also normal. The mouse does not retreat to a corner with its hair standing on end, and does not develop any observable sign of suffering. It can be concluded that the duration of action of capsaicin at these doses is less than 2 minutes.

Summary of the Methodology:

The principle of the series of tests is to determine whether the compounds of the invention can influence the behavioral response induced by a specified amount of capsaicin. The capsaicin is initially diluted to 25 mM in DMSO and diluted, for final use, in physiological serum with Tween 80 at 10%. It appears, from control studies, that in these conditions the solvent has no effect.

In practice, the test product, prepared at 25 mM in DMSO and diluted for final use in physiological serum with 10% of Tween 80 at the strongest concentration of 500 µM, is administered by local application to the surface of the cornea at a volume of 2 µl, 10 minutes before application of the capsaicin. The animal receives an ocular instillation of 2 µl of a 160 µM capsaicin solution prepared as stated above. For an observation period of 2 minutes following instillation, the number of times the instilled eye is rubbed by the ipsilateral forepaw is counted for each animal.

For a given group, the percentage protection is calculated as follows:

$P=100-((\text{average number of scratchings of the group treated with the compound/average number of scratchings of the group treated with the solvent})\times 100)$ This percentage protection is averaged for each group of animals (n=number of animals tested with the compound of the invention).

The percentage protection evaluated, in this model, for the most active compounds of the invention, used at a concentration of 500 µM, is between 20% and 100% (see example in Table 6):

TABLE 6

| Compound No. | % P 500 µM |
| --- | --- |
| 1 | 51% |
| 3 | 34% |

TABLE 6-continued

| Compound No. | % P 500 µM |
| --- | --- |
| 6 | 30% |
| 9 | 43% |
| 12 | 83% |

The results of these tests show that the most active compounds of the invention block the effects induced by stimulation of the TRPV1 receptors.

The compounds of the invention can therefore be used for the preparation of medicinal products, notably for the preparation of a medicinal product intended for preventing or treating pathologies involving type TRPV1 receptors.

Thus, according to another of its aspects, the invention relates to medicinal products that contain a compound of formula (I), or a pharmaceutically acceptable salt, or a hydrate or a solvate of said compound.

These medicinal products find application in therapeutics, notably in the prevention and/or treatment of pain and of inflammation, of chronic pain, neuropathic pain (traumatic, diabetic, metabolic, infectious, toxic, induced by anticancer treatment or iatrogenic), (osteo-) arthritic pain, rheumatic pain, fibromyalgia, back pain, pain associated with cancer, facial neuralgia, headaches, migraine, dental pain, burns, sunstroke, bites or stings, postherpetic neuralgia, muscular pain, nerve compression (central and/or peripheral), injuries of the spinal cord and/or brain, ischaemia (of the spinal cord and/or brain), neurodegeneration, hemorrhagic vascular accidents (of the spinal cord and/or brain), pain following stroke.

The compounds of the invention can be used for the preparation of a medicinal product intended for the prevention and/or treatment of urological disorders such as overactive bladder, hyperreflexia of the bladder, bladder instability, incontinence, urinary urgency, urinary incontinence, cystitis, nephritic colic, pelvic hypersensitivity and pelvic pain.

The compounds of the invention can be used for the preparation of a medicinal product intended for the prevention and/or treatment of gynecological disorders such as vulvodynia, pains associated with salpingitis, or with dysmenorrhea.

These products can also be used for the preparation of a medicinal product intended for the prevention and/or treatment of gastrointestinal disorders such as gastro-oesophageal reflux disease, gastric ulcer, duodenal ulcer, functional dyspepsia, colitis, IBS, Crohn's disease, pancreatitis, oesophagitis, hepatic colic.

The compounds of the invention can also be used for the preparation of a medicinal product intended for preventing and/or treating metabolic disorders such as diabetes.

In addition, the products of the present invention can be used in the prevention and/or treatment of respiratory disorders such as asthma, cough, COPD, bronchoconstriction and inflammatory disorders. These products can also be used for preventing and/or treating psoriasis, pruritus, irritation of the skin, eyes or mucosa, herpes simplex, herpes zoster.

The compounds of the invention can also be used for the preparation of a medicinal product intended for the treatment of depression.

According to another of its aspects, the present invention relates to pharmaceutical compositions comprising, as active principle, a compound according to the invention. Said pharmaceutical compositions contain an effective dose of at least one compound according to the invention, or a pharmaceutically acceptable salt, a hydrate or solvate of said compound, as well as at least one pharmaceutically acceptable excipient.

Said excipients are selected according to the pharmaceutical form and the desired method of administration, from the usual excipients that are known by a person skilled in the art.

In the pharmaceutical compositions of the present invention for oral, sublingual, subcutaneous, intramuscular, intravenous, topical, local, endotracheal, intranasal, transdermal or rectal administration, the active principle of formula (I) above, or its salt, solvate or hydrate if necessary, can be administered as a unit dosage form, mixed with conventional pharmaceutical excipients, to animals and to humans for the prophylaxis or the treatment of the disorders or diseases mentioned above.

The appropriate unit dosage forms include the forms by the oral route such as tablets, soft or hard capsules, powders, granules and oral solutions or suspensions, sublingual, buccal, endotracheal, intraocular, intranasal dosage forms, by inhalation, topical, transdermal, subcutaneous, intramuscular or intravenous dosage forms, rectal dosage forms and implants. For topical application, the compounds according to the invention can be used in creams, gels, ointments or lotions.

As an example, a unit dosage form of a compound according to the invention in tablet form can comprise the following constituents:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropyl methylcellulose | 2.25 mg |
| Magnesium stearate | 3.0 mg |

Said unit forms are dosed to permit a daily administration of 0.001 to 30 mg of active principle per kg of body weight, depending on the galenical form.

There may be special cases when higher or lower dosages are appropriate; said dosages are still within the scope of the invention. According to the usual practice, the dosage appropriate to each patient is determined by the doctor according to the method of administration, and said patient's weight and response.

The present invention, according to another of its aspects, also relates to a method of treatment of the aforementioned pathologies that comprises the administration, to a patient, of an effective dose of a compound according to the invention, or one of its pharmaceutically acceptable salts or hydrates or solvates.

What is claimed is:
1. A compound of the formula (I):

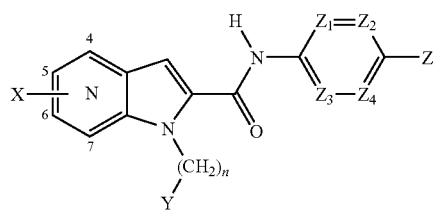

wherein:
the pyrrolopyridine nucleus is pyrrolo[2,3-b]pyridine group; and wherein
the pyrrolopyridine nucleus being optionally substituted at carbon positions 4, 5, or 6 with one or more substituents X, which may be identical to or different from one another, selected from hydrogen, halogen, $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, —S(O)—$C_1$-$C_6$-alkyl, —S(O)$_2$—$C_1$-$C_6$-alkyl, SF$_5$, C(O)NR$_1$R$_2$, SO$_2$NR$_1$R$_2$, nitro, NR$_1$R$_2$, OCONR$_1$R$_2$, NR$_3$COR$_4$, NR$_3$CONR$_1$R$_2$, NR$_3$SO$_2$R$_5$, NR$_3$SO$_2$NR$_1$R$_2$, aryl -$C_1$-$C_6$-alkylene, heteroaryl-$C_1$-$C_6$-alkylene, aryl and heteroaryl; wherein the aryl and the heteroaryl being optionally substituted with one or more substituents selected from halogen, $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro and cyano;

n is equal to 0, 1, 2 or 3;

Y represents aryl or heteroaryl;
the aryl or the heteroaryl being optionally substituted with one or more groups selected from a halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, cyano, $C_1$-$C_6$-thioalkyl, thiol, —S(O)—$C_1$-$C_6$-alkyl, —S(O)$_2$—$C_1$-$C_6$-alkyl, C(O)NR$_1$R$_2$, SO$_2$NR$_1$R$_2$, SF$_5$, nitro, OCONR$_1$R$_2$, NR$_3$COR$_4$, NR$_3$CONR$_1$R$_2$, NR$_1$R$_2$, NR$_3$SO$_2$NR$_1$R$_2$, NR$_3$COR$_4$, NR$_3$SO$_2$R$_5$, aryl-$C_1$-$C_6$-alkylene and aryl; wherein the aryl and the aryl-$C_1$-$C_6$-alkylene being optionally substituted with one or more substituents selected from halogen, $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro and cyano;

$Z_1$, $Z_2$, $Z_3$, $Z_4$ represent, independently of one another, nitrogen or C(R$_6$), wherein at least one corresponding to nitrogen and at least one corresponding to C(R$_6$); and wherein one of the nitrogen atoms present in the ring, defined as position-1 nitrogen, being optionally substituted with R$_7$ when the carbon atom in position 2 or 4 relative to this reference nitrogen is substituted with an oxo or thio group;

Z represents either a cyclic amine attached by the nitrogen atom, of formula:

in which
A represents a $C_1$-$C_7$-alkylene group optionally substituted with one or two groups R$_8$;
B represents a $C_1$-$C_7$-alkylene group optionally substituted with one or two groups R$_9$;
L represents a bond, sulfur, oxygen or nitrogen atom; the nitrogen atom being optionally substituted with a group R$_{10}$ or R$_{11}$;
the carbon atoms of the cyclic amine Z being optionally substituted with one or more groups R$_{12}$ which may be identical to or different from one another;
or an acyl amine, attached by the nitrogen atom, of formula NRaRb in which Ra and Rb represent, independently of one another, hydrogen, $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, hydroxyl, $C_1$-$C_6$-alkoxyl, $C_3$-$C_7$-cycloalkyl-$C_1$-$C_6$- alkylene-O—, $C_1$-$C_6$-fluoroalkoxyl, $C_1$-$C_6$-alkyl-C(O)—, HO—C(O)—$C_1$-$C_6$-alkylene, $C_1$-$C_6$-alkyl-O—C(O)—$C_1$-$C_6$-alkylene, aryl or heteroaryl group, and Ra and Rb can optionally be substituted with one or more groups Rc which may be identical to or different from one another;

Rc represents a halogen atom, a $C_1$-$C_6$-alkyl, $C_3$-$C_7$-cycloalkyl, $C_3$-$C_7$-cycloalkyl -$C_1$-$C_6$-alkylene, $C_1$-$C_6$-fluoroalkyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, cyano, C(O)NR$_1$R$_2$, NR$_1$R$_2$, SO$_2$NR$_1$R$_2$, NR$_3$COR$_4$, NR$_3$SO$_2$R$_5$, OC(O)NR$_1$R$_2$, NR$_3$COOR$_5$, NR$_3$CONR$_1$R$_2$, NR$_3$SO$_2$NR$_1$R$_2$, hydroxyl, thiol, oxo, thio, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl -$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of one another, hydrogen, $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group; or $R_1$ and $R_2$ taken together with the nitrogen atom to which they are attached form a cyclic ring selected from the group consisting of azetidinyl, pyrrolidinyl, piperidinyl, azepinyl, morpholinyl, thiomorpholinyl, piperazinyl and homopiperazinyl; said ring being optionally substituted with a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_3$ and $R_4$ represent, independently of one another, hydrogen, $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

or $R_3$ and $R_4$ together form a ($C_2$-$C_5$)alkylene group;

or $R_1$ and $R_3$ together form a ($C_2$-$C_5$)alkylene group;

$R_5$ represents a $C_1$-$C_6$-alkyl, $C_3$-$C_7$-cycloalkyl, $C_3$-$C_7$-cycloalkyl-$C_1$-$C_6$-alkylene, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

or $R_3$ and $R_5$ together form a ($C_2$-$C_5$)alkylene group;

$R_6$ represents a hydrogen or halogen atom or a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, hydroxyl, thiol, oxo, thio, aryl, aryl-$C_1$-$C_6$-alkylene, heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_7$ represents a hydrogen atom, a $C_1$-$C_6$-alkyl, $C_3$-$C_7$-cycloalkyl, $C_3$-$C_7$-cycloalkyl -$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, aryl, aryl-$C_1$-$C_6$-alkylene or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_1$-$C_6$-fluoroalkoxyl, nitro or cyano group;

$R_8$, $R_9$ and $R_{10}$ are defined such that:

two groups $R_8$ can together form a linkage or a $C_1$-$C_6$-alkylene group;

two groups $R_9$ can together form a linkage or a $C_1$-$C_6$-alkylene group;

$R_8$ and $R_9$ can together form a linkage or a $C_1$-$C_6$-alkylene group;

$R_8$ and $R_{10}$ can together form a linkage or a $C_1$-$C_6$-alkylene group;

$R_9$ and $R_{10}$ can together form a linkage or a $C_1$-$C_6$-alkylene group;

$R_{11}$ represents a hydrogen atom, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, hydroxyl, $C_1$-$C_6$-alkyl-CO—, COOR$_5$, C(O)NR$_1$R$_2$, aryl-$C_1$-$C_6$-alkylene, aryl or heteroaryl group, the aryl and the heteroaryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group;

$R_{12}$ represents a fluorine atom, a $C_1$-$C_6$-alkyl group optionally substituted with an $R_{13}$, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-cycloalk-1,1-diyl, $C_3$-$C_7$-heterocycloalk-1,1-diyl group optionally substituted on a nitrogen atom with an $R_{11}$, $C_1$-$C_6$-alkoxyl, $C_3$-$C_7$-cycloalkoxyl, $C_3$-$C_7$-cycloalkyl-$C_1$-$C_6$-alkylene-O—, $C_1$-$C_6$-fluoroalkoxyl, CO$_2$H, C(O)O—$C_1$-$C_6$-alkyl, C(O)NR$_1$R$_2$, NR$_1$R$_2$, NR$_3$COR$_4$, OC(O)NR$_1$R$_2$, NR$_3$COOR$_5$, NR$_3$CONR$_1$R$_2$, hydroxyl, thiol, oxo, thio, aryl-$C_1$-$C_6$-alkylene, aryl group, the aryl being optionally substituted with one or more substituents selected from a halogen, a $C_1$-$C_6$-alkyl, $C_3$-$C_7$-cycloalkyl, $C_3$-$C_7$-cycloalkyl-$C_1$-$C_6$-alkylene, $C_1$-$C_6$-fluoroalkyl, $C_1$-$C_6$-alkoxyl, $C_3$-$C_7$-cycloalkoxyl, $C_1$-$C_6$-fluoroalkoxyl, nitro or cyano group; and $R_{13}$ represents a $C_1$-$C_6$-alkoxy, $C_3$-$C_7$-cycloalkoxyl, $C_3$-$C_7$-cycloalkyl-$C_1$-$C_6$-alkylene-O—, C(O)NR$_1$R$_2$, NR$_1$R$_2$, NR$_3$COR$_4$, OC(O)NR$_1$R$_2$, NR$_3$COOR$_5$, hydroxyl group;

or an N-oxide thereof or a salt thereof.

2. The compound of formula (I) according to claim 1, wherein the substituent or substituents X, which may be identical to or different from one another, are selected from hydrogen, halogen or $C_1$-$C_6$-fluoroalkyl.

3. The compound of formula (I) according to claim 1, wherein n is equal to 1.

4. The compound of formula (I) according to claim 1, wherein Y represents an aryl or a heteroaryl, the aryl or the heteroaryl being optionally substituted with one or more groups selected from halogen, $C_1$-$C_6$-alkyl, $C_1$-$C_6$-fluoroalkyl, $C_1$-$C_6$-alkoxyl or $C_1$-$C_6$-fluoroalkoxyl.

5. The compound of formula (I) according to claim 1, wherein:
$Z_1$, $Z_2$, $Z_3$, $Z_4$ represent, independently of one another, nitrogen or $C(R_6)$, at least one corresponding to nitrogen and at least one corresponding to $C(R_6)$;
$R_6$ represents hydrogen, halogen, $C_1$-$C_6$-alkyl, $C_1$-$C_6$-fluoroalkyl or $C_1$-$C_6$-alkoxyl.

6. The compound of formula (I) according to claim 1, wherein:
Z represents either a cyclic amine attached by the nitrogen atom, of formula:

in which
A represents a $C_1$-$C_7$-alkylene group optionally substituted with one or two groups $R_8$;
B represents a $C_1$-$C_7$-alkylene group optionally substituted with one or two groups $R_9$;
L represents a linkage;
the carbon atoms of the cyclic amine Z being optionally substituted with one or more groups $R_{12}$ which may be identical to or different from one another;
$R_{12}$ represents a fluorine atom, a $C_1$-$C_6$-alkyl, $C_1$-$C_6$-alkoxyl, $C_3$-$C_7$-cycloalkyl-$C_1$-$C_6$-alkylene-O—, $CO_2H$, $C(O)O$—$C_1$-$C_6$-alkyl or hydroxyl group;
$R_8$ and $R_9$ are defined such that:
two groups $R_8$ can together form a linkage or a $C_1$-$C_6$-alkylene group;
two groups $R_9$ can together form a linkage or a $C_1$-$C_6$-alkylene group;
$R_8$ and $R_9$ can together form a linkage or a $C_1$-$C_6$-alkylene group;
or an acyl amine, attached by the nitrogen atom, of formula NRaRb in which Ra and Rb represent, independently of one another, a hydrogen atom or a $C_1$-$C_6$-alkyl, $C_1$-$C_6$-alkyl-C(O)—, HO—C(O)—$C_1$-$C_6$-alkylene or $C_1$-$C_6$-alkyl-O—C(O)—$C_1$-$C_6$-alkylene, and Ra and Rb can optionally be substituted with a group Rc where Rc represents a hydroxyl.

7. The compound of formula (I) according to claim 6, wherein:
Z represents either a cyclic amine attached by the nitrogen atom, of formula:

in which
A represents a $C_1$-$C_7$-alkylene group optionally substituted with a group $R_8$;
B represents a $C_1$-$C_7$-alkylene group optionally substituted with a group $R_9$;
L represents a linkage;
the carbon atoms of the cyclic amine Z being optionally substituted with one or more groups $R_{12}$ which may be identical to or different from one another;
$R_{12}$ represents a fluorine atom, a $C_1$-$C_6$-alkyl, $C_1$-$C_6$-alkoxyl, $C_3$-$C_7$-cycloalkyl-$C_1$-$C_6$-alkylene-O—, $CO_2H$, $C(O)O$—$C_1$-$C_6$-alkyl or hydroxyl group;
$R_8$ and $R_9$ are defined such that:
$R_8$ and $R_9$ can together form a linkage;
or an acyl amine, attached by the nitrogen atom, of formula NRaRb in which Ra and Rb represent, independently of one another, a hydrogen atom or a $C_1$-$C_6$-alkyl, $C_1$-$C_6$-alkyl-C(O)—, HO—C(O)—$C_1$-$C_6$-alkylene or $C_1$-$C_6$-alkyl-O—C(O)—$C_1$-$C_6$-alkylene group, and Ra and Rb can optionally be substituted with a group Rc where Rc represents a hydroxyl.

8. The compound of formula (I) according to claim 7, wherein:
Z represents either a cyclic amine attached by the nitrogen atom and selected from the pyrrolidinyl, azetidinyl, azabicyclo[3.2.0]heptyl or azabicyclo[3.1.0]hexyl groups, the carbon atoms of the cyclic amine being optionally substituted with one or more groups $R_{12}$ which may be identical to or different from one another;
$R_{12}$ represents a fluorine atom, a $C_1$-$C_6$-alkyl, $C_1$-$C_6$-alkoxyl, $C_3$-$C_7$-cycloalkyl-$C_1$-$C_6$-alkylene-O—, $CO_2H$, $C(O)O$—$C_1$-$C_6$-alkyl or hydroxyl group;
or an acyl amine, attached by the nitrogen atom, of formula NRaRb in which Ra and Rb represent, independently of one another, a hydrogen atom or a $C_1$-$C_6$-alkyl, $C_1$-$C_6$-alkyl-C(O)—, HO—C(O)—$C_1$-$C_6$-alkylene or $C_1$-$C_6$-alkyl-O—C(O)—$C_1$-$C_6$-alkylene group, and Ra and Rb can optionally be substituted with a group Rc where Rc represents a hydroxyl.

9. The compound of formula (I) according to claim 1, wherein:
the pyrrolopyridine nucleus is a pyrrolo[2,3-b]pyridine group;
the substituent or substituents X, which may be identical to or different from one another, are selected from a hydrogen or halogen atom or a $C_1$-$C_6$-fluoroalkyl group;
n is equal to 1;
Y represents an aryl or a heteroaryl, the aryl or the heteroaryl being optionally substituted with one or more groups selected from a halogen atom or a $C_1$-$C_6$-alkyl, $C_1$-$C_6$-fluoroalkyl, $C_1$-$C_6$-alkoxyl or $C_1$-$C_6$-fluoroalkoxyl group;
$Z_1$, $Z_2$, $Z_3$, $Z_4$ represent, independently of one another, a nitrogen atom or a group $C(R_6)$, at least one corresponding to a nitrogen atom and at least one corresponding to a group $C(R_6)$;
$R_6$ represents a hydrogen or halogen atom or a $C_1$-$C_6$-alkyl, $C_1$-$C_6$-fluoroalkyl or $C_1$-$C_6$-alkoxyl group;
Z represents either a cyclic amine attached by the nitrogen atom and selected from the pyrrolidinyl, azetidinyl, azabicyclo[3.2.0]heptyl or azabicyclo[3.1.0]hexyl groups, the carbon atoms of the cyclic amine being optionally substituted with one or more groups $R_{12}$ which may be identical to or different from one another;
$R_{12}$ represents a fluorine atom, a $C_1$-$C_6$-alkyl, $C_1$-$C_6$-alkoxyl, $C_3$-$C_7$-cycloalkyl-$C_1$-$C_6$-alkylene-O—, $CO_2H$, $C(O)O$—$C_1$-$C_6$-alkyl or hydroxyl group;
or an acyl amine, attached by the nitrogen atom, of formula NRaRb in which Ra and Rb represent, independently of one another, a hydrogen atom or a $C_1$-$C_6$-alkyl, $C_1$-$C_6$-alkyl-C(O)—, HO—C(O)—$C_1$-$C_6$-alkylene or $C_1$-$C_6$-alkyl-O—C(O)—$C_1$-$C_6$-alkylene group, and Ra and Rb can optionally be substituted with a group Rc where Rc represents a hydroxyl.

10. A method of preparation of a compound of formula (I) according to claim 1 comprising:

reacting a compound of formula (IV) in a solvent:

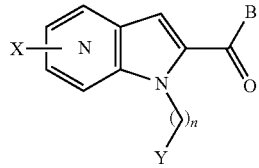

(IV)

in which the pyrrolopyridine nucleus is a pyrrolo [2,3-b] group;

X, Y and n are as defined in claim 1 and B represents a chlorine atom, with an amine of general formula (V):

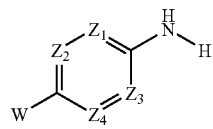

in which W=Z and Z, $Z_1$, $Z_2$, $Z_3$ and $Z_4$ are as defined in claim 1.

11. A method of preparation of a compound of formula (I) according to claim 1 comprising:

reacting a compound of general formula (IV):

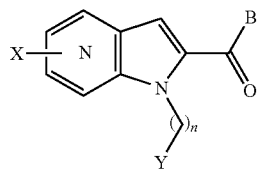

(IV)

in which the pyrrolopyridine nucleus is a pyrrolo [2,3-b] group;

X, Y and n are as defined in claim 1 and B represents a hydroxyl group, with an amine of general formula (V):

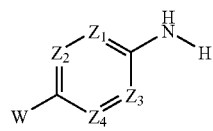

in which W=Z and Z, $Z_1$, $Z_2$, $Z_3$ and $Z_4$ are as defined in claim 1, in the presence of a coupling agent, and optionally a base, in a solvent.

12. A method of preparation of a compound of formula (I) according to claim 1 comprising:

reacting a compound of general formula (VI):

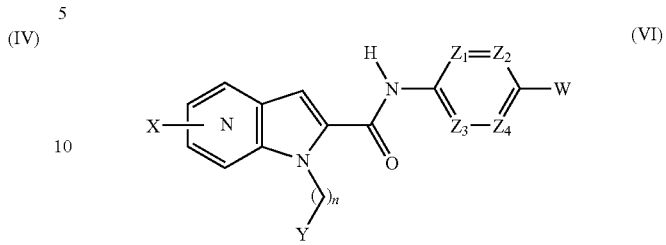

(VI)

in which the pyrrolopyridine nucleus is a pyrrolo [2,3-b] group;

X, Y, n, $Z_1$, $Z_2$, $Z_3$ and $Z_4$ are as defined in claim 1 and W represents a halogen atom, with an amine of formula Z—H, in which Z is as defined in claim 1.

13. A pharmaceutical composition comprising a compound of formula (I) according to claim 1 or a pharmaceutically acceptable salt thereof in combination with at least one pharmaceutically acceptable excipient.

14. A pharmaceutical composition comprising a compound of formula (I) according to claim 2 or a pharmaceutically acceptable salt thereof in combination with at least one pharmaceutically acceptable excipient.

15. A pharmaceutical composition comprising a compound of formula (I) according to claim 3 or a pharmaceutically acceptable salt thereof in combination with at least one pharmaceutically acceptable excipient.

16. A pharmaceutical composition comprising a compound of formula (I) according to claim 4 or a pharmaceutically acceptable salt thereof in combination with at least one pharmaceutically acceptable excipient.

17. A pharmaceutical composition comprising a compound of formula (I) according to claim 5 or a pharmaceutically acceptable salt thereof in combination with at least one pharmaceutically acceptable excipient.

18. A pharmaceutical composition comprising a compound of formula (I) according to claim 6 or a pharmaceutically acceptable salt thereof in combination with at least one pharmaceutically acceptable excipient.

19. A pharmaceutical composition comprising a compound of formula (I) according to claim 7 or a pharmaceutically acceptable salt thereof in combination with at least one pharmaceutically acceptable excipient.

20. A pharmaceutical composition comprising a compound of formula (I) according to claim 8 or a pharmaceutically acceptable salt thereof in combination with at least one pharmaceutically acceptable excipient.

21. A pharmaceutical composition comprising a compound of formula (I) according to claim 9 or a pharmaceutically acceptable salt thereof in combination with at least one pharmaceutically acceptable excipient.

\* \* \* \* \*